United States Patent
Messersmith et al.

(10) Patent No.: US 11,992,532 B2
(45) Date of Patent: May 28, 2024

(54) HYDROGELS AND METHODS OF USING THE SAME

(71) Applicants: THE REGENTS OF THE UNIVERSITY OF CALIFORNIA, Oakland, CA (US); LANKENAU INSTITUTE FOR MEDICAL RESEARCH, Wynnewood, PA (US)

(72) Inventors: Phillip B. Messersmith, Berkeley, CA (US); Jing Cheng, Berkeley, CA (US); Ellen Heber-Katz, Wynnewood, PA (US)

(73) Assignees: The Regents of the University of California, Oakland, CA (US); Lankenau Institute for Medical Research, Wynnewood, PA (US)

( * ) Notice: Subject to any disclaimer, the term of this patent is extended or adjusted under 35 U.S.C. 154(b) by 55 days.

(21) Appl. No.: 17/437,579

(22) PCT Filed: Mar. 11, 2020

(86) PCT No.: PCT/US2020/022196
§ 371 (c)(1),
(2) Date: Sep. 9, 2021

(87) PCT Pub. No.: WO2020/209969
PCT Pub. Date: Oct. 15, 2020

(65) Prior Publication Data
US 2022/0143211 A1 May 12, 2022

Related U.S. Application Data

(60) Provisional application No. 62/816,431, filed on Mar. 11, 2019.

(51) Int. Cl.
*A61K 47/69* (2017.01)
*A61K 47/60* (2017.01)

(52) U.S. Cl.
CPC .......... *A61K 47/6903* (2017.08); *A61K 47/60* (2017.08)

(58) Field of Classification Search
CPC ............................ A61K 47/6903; A61K 47/60
See application file for complete search history.

(56) References Cited

U.S. PATENT DOCUMENTS

| | | | |
|---|---|---|---|
| 6,200,974 B1 | 3/2001 | Edwards et al. | |
| 2015/0196512 A1 | 7/2015 | Nicolls et al. | |
| 2015/0320877 A1 | 11/2015 | Messersmith et al. | |
| 2017/0273971 A1 | 9/2017 | Messersmith et al. | |

FOREIGN PATENT DOCUMENTS

| | | |
|---|---|---|
| WO | WO-99/21860 A1 | 5/1999 |
| WO | WO-2011/031870 A1 | 3/2011 |
| WO | WO-2017/027810 A2 | 2/2017 |

OTHER PUBLICATIONS

Aida, T. et al. (Feb. 17, 2012). "Functional Supramolecular Polymers," Science 335(6070):813-817.
Appel, E.A. et al. (Feb. 19, 2015). "Self-assembled hydrogels utilizing polymer-nanoparticle interactions," Nat Commun 6:6295.
Bedelbaeva, K. et al. (Mar. 30, 2010) "Lack of p21 expression links cell cycle control and appendage regeneration in mice," PNAS USA 107(13):5845-5850.
Boekhoven, J. et al. (Mar. 19, 2014, e-published Feb. 4, 2014). "25th Anniversary Article: Supramolecular Materials for Regenerative Medicine," Advanced Materials 26(11):1642-1659.
Cheetham, A.G. et al. (Oct. 30, 2017). "Self-assembling prodrugs," Chemical Society Reviews 46(21):6638-6663.
Cheng, J. et al. (May 28, 2019, e-published May 14, 2019). "Supramolecular Polymer Hydrogels for Drug-Induced Tissue Regeneration," ACS Nano 13(5):5493-5501.
Chu, C.R. et al. (Feb. 2010). "Animal Models for Cartilage Regeneration and Repair," Tissue Engineering Part B—Reviews 16(1):105-115.
Clark, L.D. et al. (Jul. 1998). "A new murine model for mammalian wound repair and regeneration," Clinical Immunology and Immunopathology 88(1):35-45.
Goor O.J.G.M et al. (Oct. 30, 2017) "From supramolecular polymers to multi-component biomaterials," Chemical Society Reviews 46(21):6621-6637.
Hill P. et al. (Jan. 2008). "Inhibition of hypoxia inducible factor hydroxylases protects against renal ischemia-reperfusion injury," Journal of the American Society of Nephrology 19(1):39-46.
International Search Report mailed on Nov. 23, 2020, for PCT Application No. PCT/US2020/022196, filed Mar. 11, 2020, 4 pages.
Latona, J. et al. (2017). "Enhanced Liver Regeneration After Partial Hepatectomy in Mice Treated with a Prolyl Hydroxylase Inhibitor," Abstract A155, Am J Transplant. 2017; 17 (suppl 3). Located at <https://atcmeetingabstracts.com/abstract/enhanced-liver-regeneration-after-partial-hepatectomy-in-mice-treated-with-a-prolyl-hydroxylase-inhibitor/>.
Lee, H. et al. (Aug. 2008, e-published May 2, 2008). "Molecular dynamics studies of polyethylene oxide and polyethylene glycol: Hydrodynamic radius and shape anisotropy," Biophysical Journal95(4): 1590-1599.
Leferovich, J.M. et al. (Aug. 14, 2001, e-published Aug. 7, 2001). "Heart regeneration in adult MRL mice," PNAS USA 98(17):9830-9835.
McBrearty, B.A. et al. (Sep. 29, 1998). "Genetic analysis of a mammalian wound-healing trait," PNAS USA 95(20): 11792-11797.
Naviaux, R.K. et al. (Mar. 2009, e-published Jan. 7, 2009). "Retained features of embryonic metabolism in the adult MRL mouse," Molecular Genetics and Metabolism 96(3):133-144.

(Continued)

Primary Examiner — James W Rogers
(74) Attorney, Agent, or Firm — Irina E. Britva; Mintz, Levin, Cohn, Ferris, Glovsky and Popeo, P.C.

(57) ABSTRACT

Disclosed herein are PEG-DPCA conjugates having multiple hydrophobic DPCA groups at one or both terminal ends of a PEG compound and compositions thereof and methods of using thereof for tissue regeneration and/or cellular repair (e.g., wound healing).

10 Claims, 40 Drawing Sheets

(56) References Cited

OTHER PUBLICATIONS

Partial Supplementary European Search Report mailed on Mar. 20, 2023, EP Application No. 20787658.2, 14 pages.
Van Ommen, J.R. et al. (Mar. 2012, e-published Feb. 10, 2012). "Fluidization of nanopowders: a review," Journal of Nanoparticle Research 14(3):737.
Wong Po Foo, C.T.S. et al. (Dec. 29, 2009, e-published Dec. 10, 2009). "Two-component protein-engineered physical hydrogels for cell encapsulation," *PNAS USA* 106(52): 22067-22072.
Written Opinion mailed on Nov. 23, 2020, for PCT Application No. PCT/US2020/022196, filed Mar. 11, 2020, 6 pages.
Yan, C. et al. (Oct. 21, 20100. "Injectable solid hydrogel: mechanism of shear-thinning and immediate recovery of injectable β-hairpin peptide hydrogels," *Soft Matter* 6(20):5143-5156.
Zhang, Y et al. (Jun. 3, 2015). "Drug-induced regeneration in adult mice," *Science Translational Medicine* 7(290):290ra92.

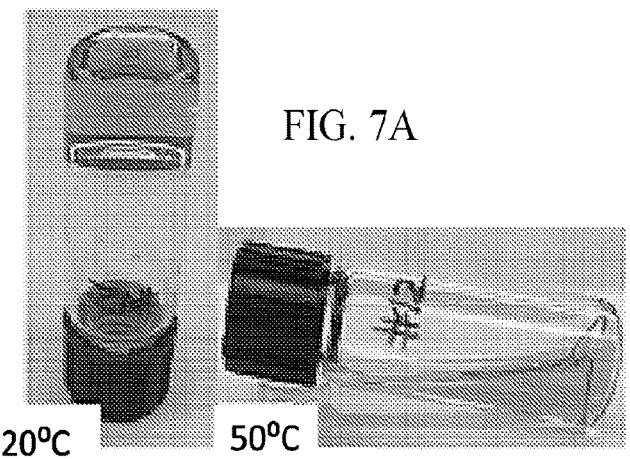
FIG. 7A
FIG. 7B
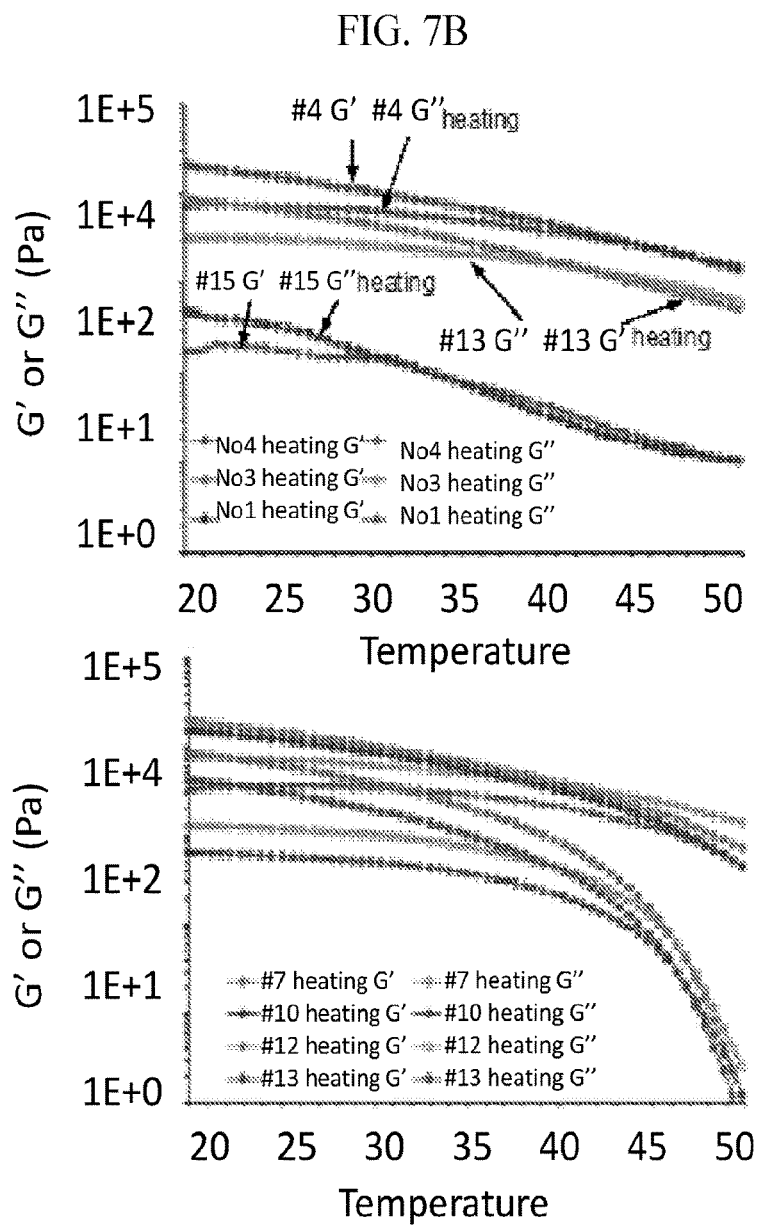

CO (1/1 EH)

RIGHT

LEFT

BEFORE

CO (1/1 EH)

RIGHT

LEFT

AFTER

B4 (0.5/0.1 EH)

RIGHT-side view    front view

BEFORE

Before drug Right:   1.25mm crown width
                     0.8mm depth of bone loss between yellow arrows

AFTER

After drug Right:    1.2mm crown width
                     0.4mm depth of bone loss between yellow arrows

BEFORE DRUG

AFTER DRUG

PULP

Plus Jing gel Drug

PULP

FIG. 30A
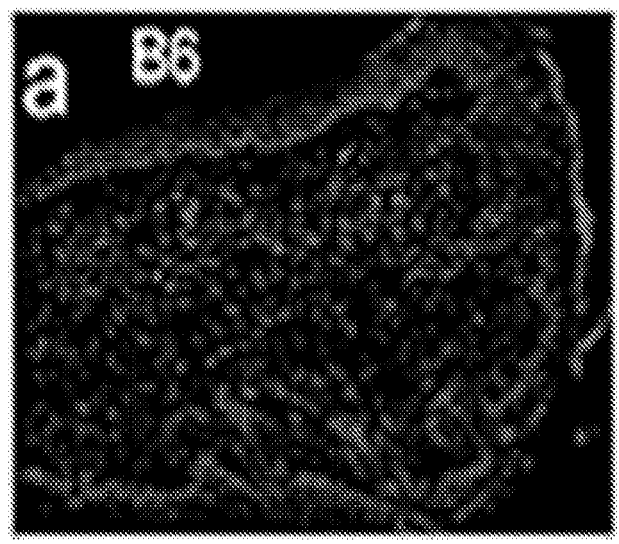
FIG. 30AA
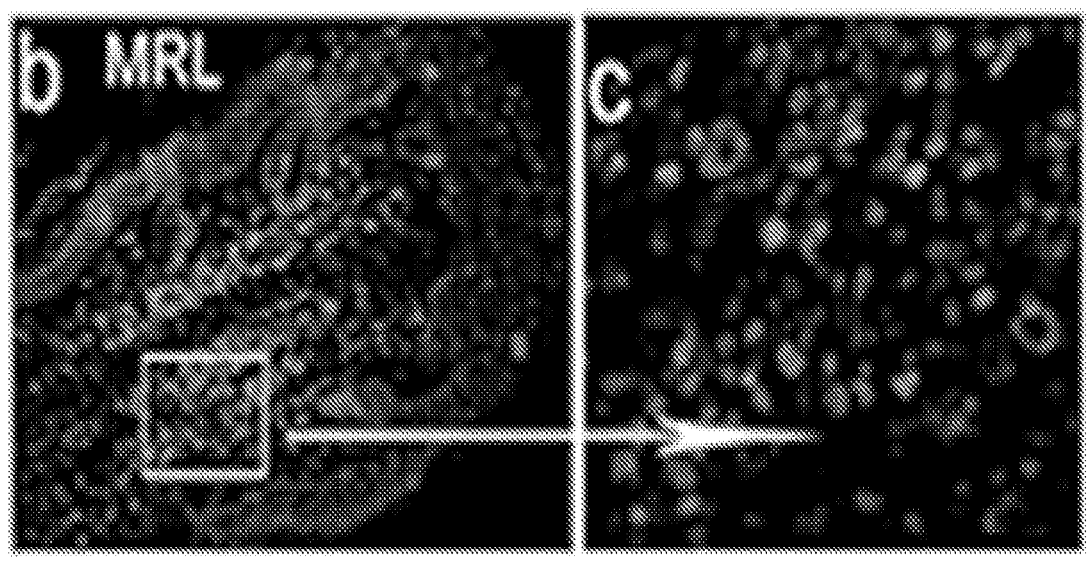
FIG. 30AB          FIG. 30AC

FIG. 30B
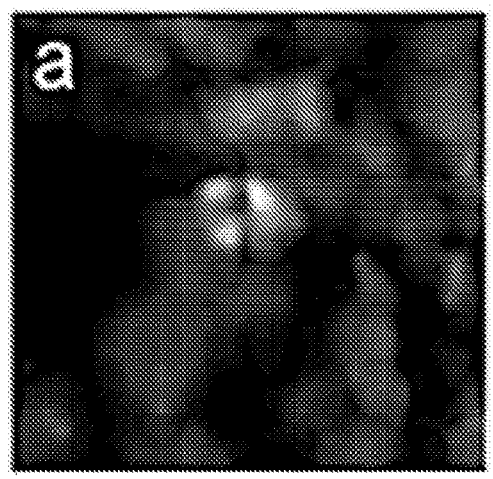
FIG. 30BA
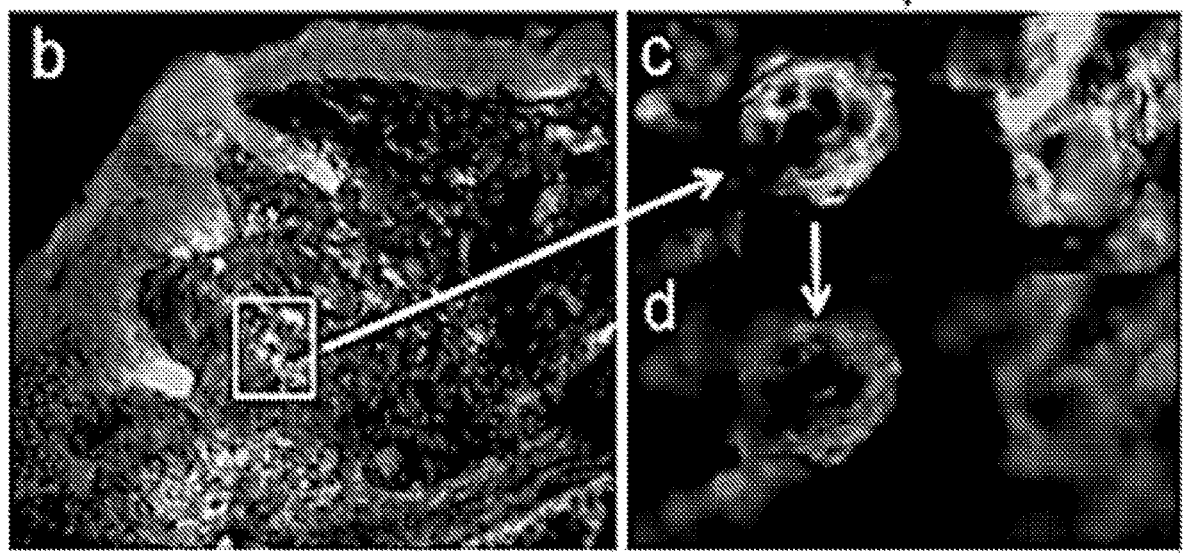
FIG. 30BB　　　　　　　　FIG. 30BC

HYDROGELS AND METHODS OF USING THE SAME

CROSS-REFERENCE TO RELATED APPLICATIONS

This application is the national stage filing under U.S.C. 371 of International Application No. PCT/US20/22196, filed on Mar. 11, 2020, which claims priority to U.S. Application No. 62/816,431 filed Mar. 11, 2019, the disclosures of which are incorporated by reference herein in their entireties and for all purposes.

ACKNOWLEDGEMENT OF GOVERNMENT SUPPORT

This invention was made with Government support under Grant Numbers DE021104 and DE021215, awarded by the National Institutes of Health. The Government has certain rights in the invention.

FIELD

The present invention generally relates to hydrogels comprising polyether compounds having dihydrophenonthrolin-4-one-3-carboxylic acid (DPCA) groups.

BACKGROUND

Supramolecular polymers self-assemble into filaments, micelles, and other nanostructures through weak noncovalent interactions between subunits. Such systems possess attractive properties for use in a variety of practical settings such as energy, sustainability, and healthcare. In regenerative medicine, a typical approach involves implanting a supramolecular material containing cell and growth factor binding motifs directly into a diseased or traumatized tissue defect whereupon it interacts with and/or recruits components of the biological system to induce tissue healing.

Both the foregoing general description and the following detailed description are exemplary and explanatory only and are intended to provide further explanation of the invention as claimed. The accompanying drawings are included to provide a further understanding of the invention and are incorporated in and constitute part of this specification, illustrate several embodiments of the invention, and together with the description explain the principles of the invention.

SUMMARY

In an aspect, provided herein is a conjugate comprising a biomacromolecule and a first DPCA group, wherein the biomacromolecule comprises a first terminal end and a second terminal end and wherein the first DPCA group is covalently joined directly or indirectly to the first terminal end or the second terminal end.

In embodiments, the conjugate further comprising a second DPCA group covalently joined directly or indirectly to the first terminal end or the second terminal end. In embodiments, the DPCA is covalently joined to the biomacromolecule by a linker. In embodiments, the linker is capable of in vivo cleavage. In embodiments, the cleavage is hydrolytic cleavage.

In embodiments, the linker comprises a group selected from the group consisting of ester, anhydride, peptide, thioester, hydrazine, disulfide, azo, Schiff bases and acetal.

In embodiments, the linker has the formula -$L^1$-$L^2$-$L^3$-, wherein:

$L^1$ and $L^3$ are independently a bond, —O—, —S—, —NH—, —C(O)NH—, —C(O)—, —S(O)$_{n1}$NH—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene, wherein n1 is an integer from 1 to 3; and $L^2$ is —C(O)O—, —C(O)—O—C(O)—, a peptide linker, —C(O)S—, —NH—NH—, —S—S—, —N=N—, —C(N(R$^1$))—, —C(OR$^2$)(OR$^3$)—, wherein R$^1$, R$^2$, and R$^3$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In embodiments, the conjugate has the formula: (X-$L^3$-$L^2$-$L^1$)$_{n2}$-A-($L^1$-$L^2$-$L^3$-X)$_{n3}$, wherein: X is a DPCA group; n2 and n3 are independently integers from 1 to 10; and A is said biomacromolecule. In embodiments, n2 and n3 are independently integers from 1 to 3.

In embodiments, the conjugate has the formula: (X-$L^3$-$L^2$-$L^1$)$_{n2}$-A, wherein: X is a DPCA group; n2 is an integer from 1 to 10; and A is said biomacromolecule. In embodiments, n2 is an integer from 1 to 3.

In embodiments, the biomacromolecule is selected from the group consisting of PEG, PEG-PPO block copolymer, dextran, alginate, hyaluronic acid, cyclodextrins, cellulose, hydroxypropylcellulose, chitosan, gelatin, PGA/PLA/PCL and copolymers thereof, PGA/PLA/PCL block copolymers with PEG, poly(acrylic acid), poly(methacrylic acid), poly(vinyl alcohol), poly(hydroxyethyl methacrylate), and poly(N-isopropyl acrylamide) (PNIPAAm). In embodiments, the biomacromolecule is PEG. In embodiments, the PEG is a linear PEG, branched PEG, multiarm PEG, or star PEG.

In embodiments, the PEG has an average molecular weight of about 250-20,000 Da, about 300-10,000 Da, about 400-9,000 Da, or about 500-8,000 Da. In embodiments, the PEG has an average molecular weight of about 300-10,000 Da. In embodiments, the PEG has an average molecular weight of about 400-9,000 Da. In embodiments, the PEG has an average molecular weight of about 500-8,000 Da.

In embodiments, the conjugate comprises at least 2 DPCA groups.

In embodiments, the conjugate has structural Formula I or structural Formula II as follows:

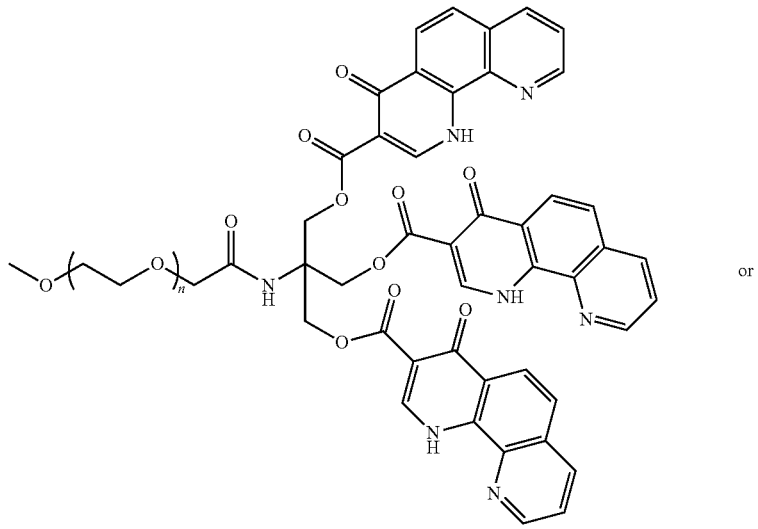

(I)

or

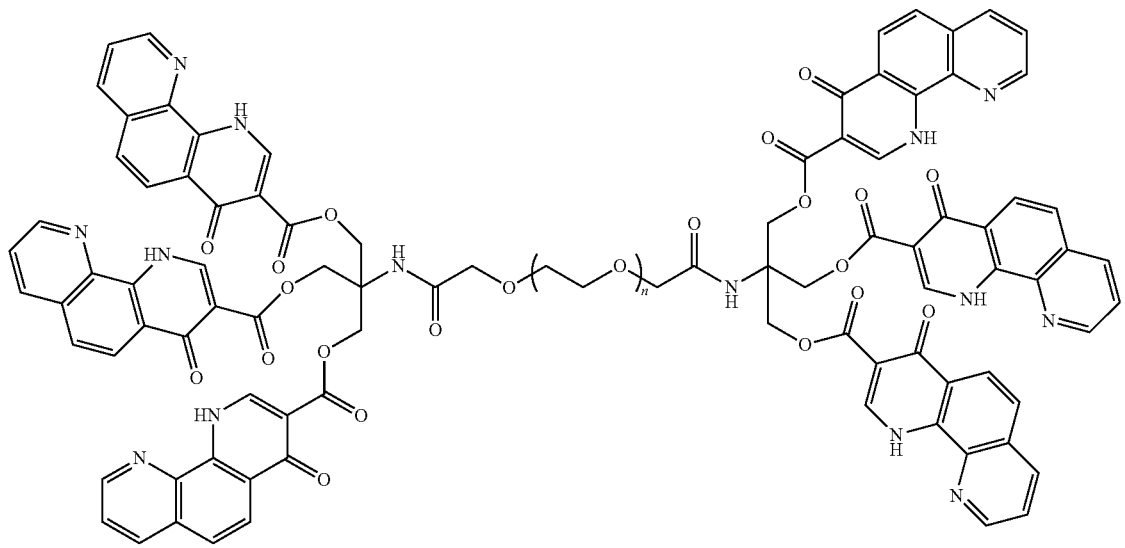

(II)

wherein n>1.

In an aspect, provided herein is a composition comprising at least one conjugate described herein.

In an aspect, provided herein is a composition comprising two or more conjugates described herein.

In embodiments, one of the conjugates comprises P7D3. In embodiments, one of the conjugates comprises P80D6. In embodiments, one of the conjugates comprising P7D3 or P80D6.

In embodiments, the composition is selected from the group consisting of: the composition having the PEG-DPCA conjugate having structural Formula I and the PEG-DPCA conjugate having structural Formula II at a ratio of about 100 to 0 by weight; the composition having the PEG-DPCA conjugate having structural Formula I and the PEG-DPCA conjugate having structural Formula II at a ratio of about 88 to 12 by weight; the composition having the PEG-DPCA conjugate having structural Formula I and the PEG-DPCA conjugate having structural Formula II at a ratio of about 76 to 24 by weight; the composition having the PEG-DPCA conjugate having structural Formula I and the PEG-DPCA conjugate having structural Formula II at a ratio of about 66 to 34 by weight; the composition having the PEG-DPCA conjugate having structural Formula I and the PEG-DPCA conjugate having structural Formula II at a ratio of about 59 to 41 by weight; the composition having the PEG-DPCA conjugate having structural Formula I and the PEG-DPCA conjugate having structural Formula II at a ratio of about 48 to 52 by weight; the composition having the PEG-DPCA conjugate having structural Formula I and the PEG-DPCA conjugate having structural Formula II at a ratio of about 39 to 61 by weight; the composition having the PEG-DPCA conjugate having structural Formula I and the PEG-DPCA conjugate having structural Formula II at a ratio of about 32 to 68 by weight; the composition having the PEG-DPCA conjugate having structural Formula I and the PEG-DPCA conjugate having structural Formula II at a ratio of about 20 to 80 by weight; the composition having the PEG-DPCA conjugate having structural Formula I and the PEG-DPCA conjugate having structural Formula II at a ratio of about 15 to 85 by weight; the composition having the PEG-DPCA conjugate having structural Formula I and the PEG-DPCA conjugate having structural Formula II at a ratio of about 11 to 89 by weight; the composition having the PEG-DPCA conjugate having structural Formula I and the PEG-DPCA conjugate having structural Formula II at a ratio of about 10 to 90 by weight; the composition having the PEG-DPCA conjugate having structural Formula I and the PEG-DPCA conjugate having structural Formula II at a ratio of about 8 to 92 by weight; the composition having the PEG-DPCA conjugate having structural Formula I and the PEG-DPCA conjugate having structural Formula II at a ratio of about 5 to 95 by weight; the composition having the PEG-DPCA conjugate having structural Formula I and the PEG-DPCA conjugate having structural Formula II at a ratio of about 3 to 97 by weight; the composition having the PEG-DPCA conjugate having structural Formula I and the PEG-DPCA conjugate having structural Formula II at a ratio of about 1 to 99 by weight; the composition having the PEG-DPCA conjugate having structural Formula I and the PEG-DPCA conjugate having structural Formula II at a ratio of about 0 to 100 by weight.

In embodiments, the PEG-DPCA conjugate having structural Formula I is P7D3. In embodiments, the PEG-DPCA conjugate having structural Formula II is P80D6.

In embodiments, the mol percentage ratio between structural Formula I and structural Formula II is selected from the group consisting of about 100:0, 97.5:2.5, 95:5, 92.5:7.5, 90:10, 85:15, 80:20, 75:25, 62:38, 53:47, 45:55, 41:59, 35:65, 25:75, 15:85, 5:95, and 0:100. In embodiments, the mol percentage ratio between structural Formula I and structural Formula II is 100:0. In embodiments, the mol percentage ratio between structural Formula I and structural Formula II is 97.5:2.5. In embodiments, the mol percentage ratio between structural Formula I and structural Formula II is 95:5. In embodiments, the mol percentage ratio between structural Formula I and structural Formula II is 92.5:7.5. In embodiments, the mol percentage ratio between structural Formula I and structural Formula II is 90:10. In embodiments, the mol percentage ratio between structural Formula I and structural Formula II is 85:15. In embodiments, the mol percentage ratio between structural Formula I and structural Formula II is 80:20. In embodiments, the mol percentage ratio between structural Formula I and structural Formula II is 75:25. In embodiments, the mol percentage ratio between structural Formula I and structural Formula II is 62:38. In embodiments, the mol percentage ratio between structural Formula I and structural Formula II is 53:47. In embodiments, the mol percentage ratio between structural Formula I and structural Formula II is 45:55. In embodiments, the mol percentage ratio between structural Formula I and structural Formula II is 41:59. In embodiments, the mol percentage ratio between structural Formula I and structural Formula II is 35:65. In embodiments, the mol percentage ratio between structural Formula I and structural Formula II is 25:75. In embodiments, the mol percentage ratio between structural Formula I and structural Formula II is 15:85. In embodiments, the mol percentage ratio between structural Formula I and structural Formula II is 5:95. In embodiments, the mol percentage ratio between structural Formula I and structural Formula II is 0:100.

In an aspect, provided herein is a method of upregulating or increasing release of hypoxia-inducible factor $1\alpha$ (HIF-$1\alpha$) in a subject, which comprises administering to the subject one or more conjugates described herein.

In an aspect, provided herein is a method of inducing, improving, enhancing, or increasing epimorphic tissue regeneration and/or cellular repair, which comprises contacting a cell or tissue with one or more conjugates described herein. In embodiments, the cell or tissue is ex-vivo. In embodiments, the cell or tissue is in vivo (e.g., part of a living animal, such as a mammal or human). In embodiments, the cell or tissue is derived from skin, bone or cartilage.

In an aspect, provided herein is a method of inducing, improving, enhancing, or increasing epimorphic tissue regeneration and/or cellular repair in a subject, which comprises administering to the subject one or more conjugates described herein. In embodiments, the one or more conjugates or the composition is administered topically to the subject. In embodiments, the one or more conjugates or the composition is administered systemically to the subject. In embodiments, the one or more conjugates or composition is applied to a site distal to the site identified for epimorphic regeneration or cellular repair. In embodiments, the site of epimorphic tissue regeneration and/or cellular repair comprises skin, hair, eye, ear, nervous system, bone, limb, organ or vascular tissue.

In an aspect, provided herein is a method of reducing or reversing one or more symptoms of aging, comprising administering to a subject one or more conjugates described herein, wherein the administration improves the rate or the quality of epimorphic regeneration. In embodiments, the rate or the quality of epimorphic regeneration is improved for skin, bone, or hair.

In an aspect, provided herein is a method of reducing or reversing one or more symptoms of aging, comprising administering to a subject one or more conjugates described herein, wherein the administration reduces or slows the rate of tissue or cell degeneration or death. In embodiments, the tissue or cell comprises skin, hair, bone or cartilage.

In an aspect, provided herein is a method of inducing epimorphic tissue regeneration, comprising administering to a subject one or more conjugates described herein, wherein the administration results in the healing of a skin wound, a skin ulcer, the growth of bone, the growth of cartilage, the growth of hair and any combination thereof.

In an aspect, provided herein is a method of inducing nerve growth, comprising administering to a subject one or more conjugates described herein, wherein the administration results in the growth of nerve cells.

In an aspect, provided herein is a method of treating osteoporosis, comprising administering to a subject one or more conjugates described herein.

In an aspect, provided herein is a method of improving density and quality of the bone, comprising administering to a subject one or more conjugates described herein, and wherein the administration results in the improvement of the quality or density of bone of the subject as compared to the bone prior to treatment.

In an aspect, provided herein is a method of treating fibrosis, comprising administering to a subject one or more conjugates described herein. In embodiments, the fibrosis is kidney fibrosis or liver fibrosis.

In an aspect, provided herein is a method of treating tissue injury, comprising administering to a subject one or more conjugates described herein, wherein the administration improves the health of the tissue as compared to the tissue prior to treatment. In embodiments, the tissue is kidney tissue or liver tissue.

In an aspect, provided herein is a method of inducing vasculogenesis, comprising administering to a subject one or more conjugates described herein, wherein the administration induced the formation of or maturation of mature blood vessels in the subject.

In an aspect, provided herein is a PEG-DPCA conjugate comprising two or more DPCA groups at one terminal end of a PEG compound or at each terminal end of the PEG compound.

In embodiments, the PEG-DPCA conjugate having the formula $X_a$-PEG(A)-$X_b$, wherein X is DPCA, and a and b represent the number of DPCA groups at each terminal end of the PEG compound. In embodiments (A) represents the structure of the PEG compound. In embodiments, the sum of a and b is equal to or greater than 2. In embodiments, when a is 0, b is 1 or greater than 1. In embodiments, when a is 1, b is 2 or greater than 2. In embodiments, when a is 3 or more than 3, b is 0, 1, 2, 3, 4, 5, 6, or more than 6. In embodiments, when a is 0, b is 2 or greater than 2. In embodiments, when a is 1, b is 1 or greater than 1.

In embodiments, the PEG compound is selected from the group consisting of linear PEG, branched PEG, multiarm PEG, star PEG. In embodiments, the PEG compound has an average molecular weight of about 250-20,000 Da, about 300-10,000 Da, about 400-9,000 Da, or about 500-8,000 Da. In embodiments, the PEG compound has an average molecular weight of about about 250-20,000 Da. In embodiments, the PEG compound has an average molecular weight of about about 300-10,000 Da. In embodiments, the PEG compound has an average molecular weight of about about 400-9,000 Da. In embodiments, the PEG compound has an average molecular weight of about about 500-8,000 Da.

In embodiments, the PEG-DPCA conjugate has structural Formula I or structural Formula II:

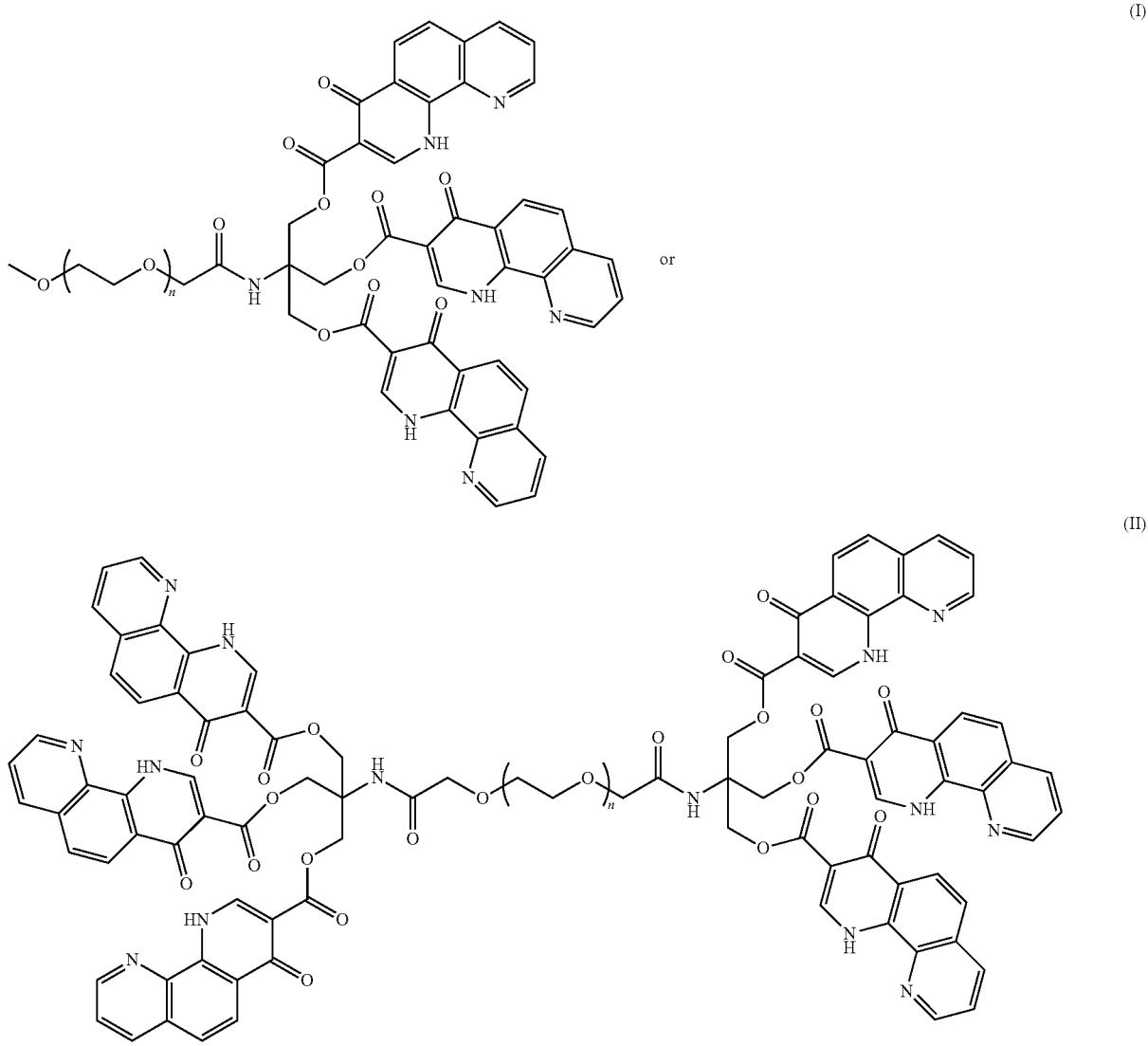

wherein n>1.

In an aspect, provided herein is a composition comprising at least one PEG-DPCA conjugate described herein. In another aspect, provided is a composition comprising two or more PEG-DPCA conjugates described herein.

In embodiments, the composition comprises at least about 1 mg/mL, at least about 3 mg/mL, at least about 5 mg/mL, at least about 8 mg/mL, at least about 10 mg/mL, at least about 11 mg/mL, at least about 15 mg/mL, at least about 20 mg/mL, at least about 32 mg/mL, at least about 39 mg/mL, at least about 48 mg/mL, at least about 59 mg/mL, at least about 66 mg/mL, at least about 76 mg/mL, at least about 88 mg/mL, or at least about 100 mg/mL of the PEG-DPCA conjugate. In embodiments, the composition comprises at least about 1 mg/mL of the PEG-DPCA conjugate. In embodiments, the composition comprises at least about 3 mg/mL of the PEG-DPCA conjugate. In embodiments, the composition comprises at least about 5 mg/mL of the PEG-DPCA conjugate. In embodiments, the composition comprises at least about 8 mg/mL of the PEG-DPCA conjugate. In embodiments, the composition comprises at least about 10 mg/mL of the PEG-DPCA conjugate. In embodiments, the composition comprises at least about 11 mg/mL of the PEG-DPCA conjugate. In embodiments, the composition comprises at least about 15 mg/mL of the PEG-DPCA conjugate. In embodiments, the composition comprises at least about 20 mg/mL of the PEG-DPCA conjugate. In embodiments, the composition comprises at least about 32 mg/mL of the PEG-DPCA conjugate. In embodiments, the composition comprises at least about 39 mg/mL of the PEG-DPCA conjugate. In embodiments, the composition comprises at least about 48 mg/mL of the PEG-DPCA conjugate. In embodiments, the composition comprises at least about 59 mg/mL of the PEG-DPCA conjugate. In embodiments, the composition comprises at least about 66 mg/mL of the PEG-DPCA conjugate. In embodiments, the composition comprises at least about 76 mg/mL of the PEG-DPCA conjugate. In embodiments, the composition comprises at least about 88 mg/mL of the PEG-DPCA conjugate. In embodiments, the composition comprises at least about 100 mg/mL of the PEG-DPCA conjugate.

In embodiments, the composition comprises at least about 12 mg/mL, at least about 24 mg/mL, at least about 34 mg/mL, at least about 41 mg/mL, at least about 52 mg/mL, at least about 62 mg/mL, at least about 68 mg/mL, at least about 80 mg/mL, at least about 85 mg/mL, at least about 89 mg/mL, at least about 90 mg/mL, at least about 92 mg/mL, at least about 95 mg/mL, at least about 97 mg/mL, at least about 99 mg/mL, or at least about 100 mg/mL of the PEG-DPCA conjugate. In embodiments, the composition comprises at least about 12 mg/mL of the PEG-DPCA conjugate. In embodiments, the composition comprises at least about 24 mg/mL of the PEG-DPCA conjugate. In embodiments, the composition comprises at least about 34 mg/mL of the PEG-DPCA conjugate. In embodiments, the composition comprises at least about 41 mg/mL of the PEG-DPCA conjugate. In embodiments, the composition comprises at least about 52 mg/mL of the PEG-DPCA conjugate. In embodiments, the composition comprises at least about 62 mg/mL of the PEG-DPCA conjugate. In embodiments, the composition comprises at least about 68 mg/mL of the PEG-DPCA conjugate. In embodiments, the composition comprises at least about 80 mg/mL of the PEG-DPCA conjugate. In embodiments, the composition comprises at least about 85 mg/mL of the PEG-DPCA conjugate. In embodiments, the composition comprises at least about 89 mg/mL of the PEG-DPCA conjugate. In embodiments, the composition comprises at least about 90 mg/mL of the PEG-DPCA conjugate. In embodiments, the composition comprises at least about 92 mg/mL of the PEG-DPCA conjugate. In embodiments, the composition comprises at least about 95 mg/mL of the PEG-DPCA conjugate. In embodiments, the composition comprises at least about 97 mg/mL of the PEG-DPCA conjugate. In embodiments, the composition comprises at least about 99 mg/mL of the PEG-DPCA conjugate. In embodiments, the composition comprises at least about 100 mg/mL of the PEG-DPCA conjugate.

In embodiments, the conjugate comprises P7D3. In embodiments, the conjugate comprises P80D6.

In embodiments, the composition is selected from the group consisting of: the composition having the PEG-DPCA conjugate having structural Formula I and the PEG-DPCA conjugate having structural Formula II at a ratio of about 100 to 0 by weight; the composition having the PEG-DPCA conjugate having structural Formula I and the PEG-DPCA conjugate having structural Formula II at a ratio of about 88 to 12 by weight; the composition having the PEG-DPCA conjugate having structural Formula I and the PEG-DPCA conjugate having structural Formula II at a ratio of about 76 to 24 by weight; the composition having the PEG-DPCA conjugate having structural Formula I and the PEG-DPCA conjugate having structural Formula II at a ratio of about 66 to 34 by weight; the composition having the PEG-DPCA conjugate having structural Formula I and the PEG-DPCA conjugate having structural Formula II at a ratio of about 59 to 41 by weight; the composition having the PEG-DPCA conjugate having structural Formula I and the PEG-DPCA conjugate having structural Formula II at a ratio of about 48 to 52 by weight; the composition having the PEG-DPCA conjugate having structural Formula I and the PEG-DPCA conjugate having structural Formula II at a ratio of about 39 to 61 by weight; the composition having the PEG-DPCA conjugate having structural Formula I and the PEG-DPCA conjugate having structural Formula II at a ratio of about 32 to 68 by weight; the composition having the PEG-DPCA conjugate having structural Formula I and the PEG-DPCA conjugate having structural Formula II at a ratio of about 20 to 80 by weight; the composition having the PEG-DPCA conjugate having structural Formula I and the PEG-DPCA conjugate having structural Formula II at a ratio of about 15 to 85 by weight; the composition having the PEG-DPCA conjugate having structural Formula I and the PEG-DPCA conjugate having structural Formula II at a ratio of about 11 to 89 by weight; the composition having the PEG-DPCA conjugate having structural Formula I and the PEG-DPCA conjugate having structural Formula II at a ratio of about 10 to 90 by weight; the composition having the PEG-DPCA conjugate having structural Formula I and the PEG-DPCA conjugate having structural Formula II at a ratio of about 8 to 92 by weight; the composition having the PEG-DPCA conjugate having structural Formula I and the PEG-DPCA conjugate having structural Formula II at a ratio of about 5 to 95 by weight; the composition having the PEG-DPCA conjugate having structural Formula I and the PEG-DPCA conjugate having structural Formula II at a ratio of about 3 to 97 by weight; the composition having the PEG-DPCA conjugate having structural Formula I and the PEG-DPCA conjugate having structural Formula II at a ratio of about 1 to 99 by weight; the composition having the PEG-DPCA conjugate having structural Formula I and the PEG-DPCA conjugate having structural Formula II at a ratio of about 0 to 100 by weight.

In embodiments, the PEG-DPCA conjugate having structural Formula I is P7D3. In embodiments, the PEG-DPCA conjugate having structural Formula II is P80D6.

In an aspect, provided herein is a method of upregulating or increasing release of hypoxia-inducible factor 1α (HIF-1α) in a subject, which comprises administering to the subject one or more PEG-DPCA conjugates described herein.

In an aspect, provided herein is a method of inducing, improving, enhancing, or increasing epimorphic tissue regeneration and/or cellular repair, which comprises contacting a cell or tissue with one or more PEG-DPCA conjugates described herein. In embodiments, the cell or tissue is ex-vivo. In embodiments, the cell or tissue is in vivo (e.g., part of a living animal, such as a mammal or human). In embodiments, the cell or tissue is derived from skin, bone or cartilage.

In an aspect, provided herein is a method of inducing, improving, enhancing, or increasing epimorphic tissue regeneration and/or cellular repair in a subject, which comprises administering to the subject one or more PEG-DPCA conjugates described herein. In embodiments, the one or more conjugates or the composition is administered topically to the subject. In embodiments, the one or more conjugates or the composition is administered systemically to the subject. In embodiments, the one or more PEG-DPCA conjugates or composition thereof is applied to a site distal to the site identified for epimorphic regeneration or cellular repair. In embodiments, the site of epimorphic tissue regeneration and/or cellular repair comprises skin, hair, eye, ear, nervous system, bone, limb, organ or vascular tissue.

In an aspect, provided herein is a method of reducing or reversing one or more symptoms of aging, comprising administering to a subject one or more PEG-DPCA conjugates described herein, wherein the administration improves the rate or the quality of epimorphic regeneration. In embodiments, the rate or the quality of epimorphic regeneration is improved for skin, bone, or hair.

In an aspect, provided herein is a method of reducing or reversing one or more symptoms of aging, comprising administering to a subject one or more PEG-DPCA conjugates described herein, wherein the administration reduces or slows the rate of tissue or cell degeneration or death.

In embodiments, the tissue or cell comprises skin, hair, bone or cartilage.

In an aspect, provided herein is a method of inducing epimorphic tissue regeneration, comprising administering to a subject one or more PEG-DPCA conjugates described herein, wherein the administration results in the healing of a skin wound, a skin ulcer, the growth of bone, the growth of cartilage, the growth of hair and any combination thereof.

In an aspect, provided herein is a method of inducing nerve growth, comprising administering to a subject one or more PEG-DPCA conjugates described herein, wherein the administration results in the growth of nerve cells.

In an aspect, provided herein is a method of treating osteoporosis, comprising administering to a subject one or more PEG-DPCA conjugates described herein.

In an aspect, provided herein is a method of improving density and quality of the bone, comprising administering to a subject one or more PEG-DPCA conjugates described herein, and wherein the administration results in the improvement of the quality or density of bone of the subject as compared to the bone prior to treatment.

In an aspect, provided herein is a method of treating fibrosis, comprising administering to a subject one or more PEG-DPCA conjugates described herein. In embodiments, the fibrosis is kidney fibrosis or liver fibrosis.

In an aspect, provided herein is a method of treating tissue injury, comprising administering to a subject one or more PEG-DPCA conjugates described herein, wherein the administration improves the health of the tissue as compared to the tissue prior to treatment. In embodiments, the tissue is kidney tissue or liver tissue.

In an aspect, provided herein is a method of inducing vasculogenesis, comprising administering to a subject one or more PEG-DPCA conjugates described herein, wherein the administration induced the formation of or maturation of mature blood vessels in the subject.

DESCRIPTION OF THE DRAWINGS

This invention is further understood by reference to the drawings.

FIG. 5A: Frequency sweep at $\gamma=1\%$, 37° C.; FIG. 5B: Strain sweep at $\omega=6.28$ rad/s and 37° C.; FIG. 5C: Step-strain behavior $\gamma=1\%$ or $\gamma=200\%$, $\omega=6.28$ rad/s, 37° C.; FIG. 5D: Temperature sweep, $\gamma=1\%$, $\omega=6.28$ rad/s, heating rate 6° C./min.

In FIG. 6D, Mixtures #18 and #19 have the same ratio as Mixture #7, except that P80D6 was replaced by PEG8000 (#18) or P7D3 was replaced by PEG750 (#19).

FIGS. 7A and 7B: Thermorheological characterization of selected gels. Shown in FIG. 7A are photographs of gel #12 at 20° C. (left) and 50° C. (right). Shown in FIG. 7B are plots of the storage (G') and loss (G") moduli for oscillatory rheological characterization of selected gels analyzed at shear amplitude of $\gamma=1\%$ and frequency of $\omega=6.28$ rad/s).

FIG. 8A: The effect of composition on rheological and thermal sol-gel transition temperature ($T_{sol-gel}$). The left y-axis shows G' and G" obtained at $\omega=6.28$ rad/s, $\gamma=1\%$, T=37° C. The right y-axis shows $T_{sol-gel}$, identified in temperature sweep experiments ($\omega=6.28$ rad/s, $\gamma=1\%$) as being the temperature at which G'=G". Mixtures behaved as liquids at temperatures above $T_{sol-gel}$, and as gels below $T_{sol-gel}$. The unfilled diamonds indicate that no gelation was observed above 10° C. The vertical dashed lines indicate the compositions of Gel #3 and Gel #12. All analyses were performed at 100 mg/mL. FIG. 8B: Schematic illustration of assemblies of PEG-DPCA conjugates. Self-assembly of P7D3 and P80D6 is driven by hydrophobic interactions among DPCA groups, forming nanostructures with DPCA-rich cores and PEG corona. Shown on the left is depicted a mixture rich in P7D3 consisting of primarily P7D3 nanofibers with limited bridging of nanofibers by P80D6. In mixtures containing excess P80D6 (right), the two polymers co-aggregate to form wider and shorter nanofibers bridged extensively by P80D6, resulting in a viscoelastic gel that exhibits shear-thinning and self-healing properties.

FIG. 9A: Count rate and average particle size of P80D6 solutions at 250 and 50° C. FIG. 9B: Particle size distribution by number of P80D6 solution at 250 and 50° C. The decrease of count rate and increase of particle size at 50° C. indicated swelling and dissociation of the aggregates while heating.

FIG. 10A: EM images of P7D3 nanofibers obtained by TEM (3 mg/ml), cryo-TEM (1 mg/ml) and SEM (lyophilized powder). FIG. 10B: SAXS patterns show a cylindrical form factor, as indicated by the −1 slope at low q of the aqueous sample, and a scattering peak of the powder sample suggesting a feature size of 5-8 nm.

FIG. 13A: SAXS patterns at room temperature. FIG. 13B: Modified Guinier analysis of the samples, with slope −1 at low q range indicating the presence of cylindrical structures.

FIG. 18A: Histological sections of the subcutaneous injection site for Gel #12 and a PEG control on Day 49. FIG. 18B: Ear hole closure versus time for control and Gel #12 treated group. The grey arrows indicate time points at which 50 μL of gel was administered. (n=12 ears, p<0.005 vs control for all time points)

FIG. 19A: Ear tissue was harvested on Days 1, 3, 5, or 7 for HIF-1α immunostaining (grey). FIG. 19B: Ear hole closure versus time for control and Gel #10 treated group. The grey arrows indicate time points at which gel was administered. n=10 ears, p<0.005 vs control for all time points. FIG. 19C: Example photographs of ear holes taken on Day 35 for control group and Day 34 for Gel #10 treated group. FIGS. 19D and 19E: Histological tissue sections of Alcian blue-stained ear tissue taken on Day 34 from control mice (FIG. 19D) and Gel #10 treated mice (FIG. 19E). The grey arrow indicates the location of new hair follicles and the black arrow indicates foci of early cartilage formation.

FIG. 21A: before treatment. FIG. 21B: after treatment.

FIG. 22A: before treatment. FIG. 22B: after treatment.

FIG. 25A shows the wound on day 0. FIG. 25B shows the wound healing on day 3 after treatment. FIG. 25C shows the wound closure on day 9 after treatment.

FIG. 26A shows the difference between the skin condition of chronic skin ulcer after treatment on day 0 and day 16 in aged mice. FIG. 26B shows the difference between the skin condition of chronic skin ulcer after treatment on day 0 and day 25 in aged mice.

FIG. 27A shows nerve growth in regenerating MRL and SW (G2) mouse ear treated with PEG-DPCA hydrogel. FIG. 27B shows lack of nerve growth in non-regenerating B6 and SW-60 mouse ear treated with PEG only.

FIGS. 30A-30C. Enhanced neovascularization and vasculogenesis in regenerating ear holes after treatment with PEG-DPCA hydrogel.

FIG. 30A shows that the regenerator MRL mouse ear after injury shows an influx of CD31+ cells; the non-regenerator B6 mouse ear does not. FIG. 30AA. The B6 mouse ear shows no influx of CD31+cells. FIG. 30AB. The MRL mouse ear shows significant influx of CD31+ cells (white dots). FIG. 30AC. The area of FIG. 30 AB (white box) is enlarged to show that the labeled cells are small arterioles (white circles).

FIG. 30B. MRL bone marrow-derived cells were labeled with a fluorescent dye, injected into x-irradiated MRL recipients, and can be seen as white cells or dots. FIG. 30BA. MRL ear tissue shows labeled (white) arterioles by day 7. FIG. 30BB. MRL ear tissue shows extensively labeled (white) tissue by day 15. FIG. 30BC. The area of FIG. 30BB (white box) is enlarged to show that large vessels are labeled with the bone marrow dye (white). FIG. 30BD. In the ear, the same large vessels are co-labeled with CD31 and show that the bone marrow derived cells, which make up the vessels, are also labeled with CD31 proving that the new blood vessels come from the bone marrow.

FIG. 30C. Ear tissue after injury is examined from non regenerator Swiss Webster (SW) mice. FIG. 30CA. The non regenerator Swiss Webster ear after injury with no further treatment shows no CD31+ infiltrating cells (no white dots). FIG. 30CB. The non regenerator Swiss Webster ear after injury treated with PEG-DPCA shows significant numbers of CD31+ infiltrating cells (white dots).

DETAILED DESCRIPTION

Definitions

Figure 1:
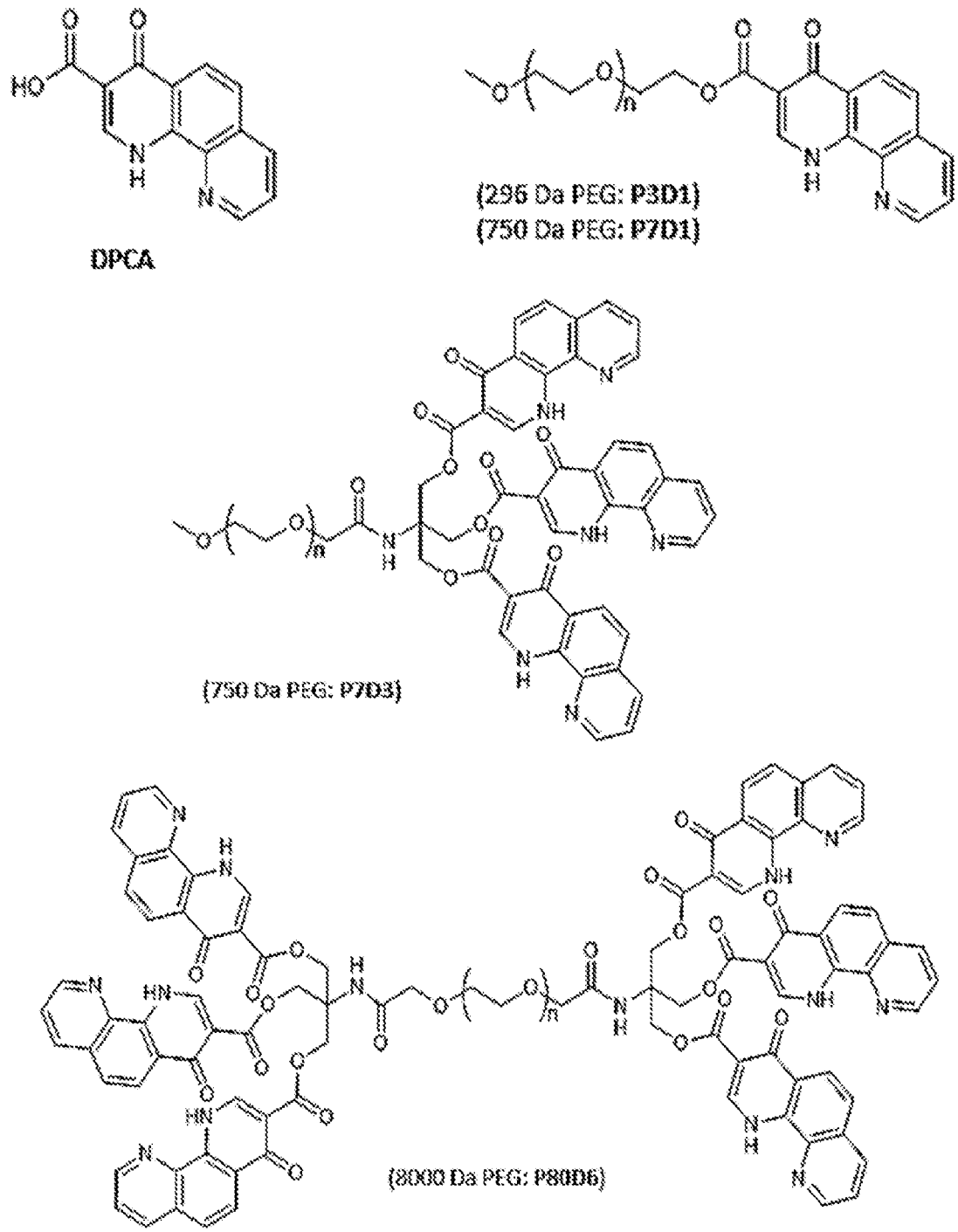
FIG. 1: Chemical structures of DPCA and PEG-DPCA conjugates studied.

The abbreviations used herein have their conventional meaning within the chemical and biological arts. The chemical structures and formulae set forth herein are constructed according to the standard rules of chemical valency known in the chemical arts.

Where substituent groups are specified by their conventional chemical formulae, written from left to right, they equally encompass the chemically identical substituents that would result from writing the structure from right to left, e.g., -ch$_2$o- is equivalent to -och$_2$-.

The term "alkyl," by itself or as part of another substituent, means, unless otherwise stated, a straight (i.e., unbranched) or branched carbon chain (or carbon), or combination thereof, which may be fully saturated, mono- or polyunsaturated and can include mono-, di- and multivalent radicals. The alkyl may include a designated number of carbons (e.g., $c_1$-$c_{10}$ means one to ten carbons). Alkyl is an uncyclized chain. Examples of saturated hydrocarbon radicals include, but are not limited to, groups such as methyl, ethyl, n-propyl, isopropyl, n-butyl, t-butyl, isobutyl, sec-butyl, methyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. An alkoxy is an alkyl attached to the remainder of the molecule via an oxygen linker (-o-). An alkyl moiety may be an alkenyl moiety. An alkyl moiety may be an alkynyl moiety. An alkyl moiety may be fully saturated. An alkenyl may include more than one double bond and/or one or more triple bonds in addition to the one or more double bonds. An alkynyl may include more than one triple bond and/or one or more double bonds in addition to the one or more triple bonds.

The term "alkylene," by itself or as part of another substituent, means, unless otherwise stated, a divalent radical derived from an alkyl, as exemplified, but not limited by, -ch$_2$ch$_2$ch$_2$ch$_2$-. Typically, an alkyl (or alkylene) group will have from 1 to 24 carbon atoms, with those groups having 10 or fewer carbon atoms being preferred herein. A "lower alkyl" or "lower alkylene" is a shorter chain alkyl or alkylene group, generally having eight or fewer carbon atoms. The term "alkenylene," by itself or as part of another substituent, means, unless otherwise stated, a divalent radical derived from an alkene.

The term "heteroalkyl," by itself or in combination with another term, means, unless otherwise stated, a stable straight or branched chain, or combinations thereof, including at least one carbon atom and at least one heteroatom (e.g., o, n, p, si, and s), and wherein the nitrogen and sulfur atoms may optionally be oxidized, and the nitrogen heteroatom may optionally be quaternized. The heteroatom(s) (e.g., o, n, s, si, or p) may be placed at any interior position of the heteroalkyl group or at the position at which the alkyl group is attached to the remainder of the molecule. Heteroalkyl is an uncyclized chain. Examples include, but are not limited to: —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—S—CH$_2$, —S(O)—CH$_3$, —CH$_2$—CH$_2$—S(O)$_2$—CH$_3$, —CH=CH—O—CH$_3$, —Si(CH$_3$)$_3$, —CH$_2$—CH=N—OCH$_3$, —CH=CH—N(CH$_3$)—CH$_3$, —O—CH$_3$, —O—CH$_2$—CH$_3$, and —CN. Up to two or three heteroatoms may be consecutive, such as, for example, CH$_2$—NH—OCH$_3$ and —CH$_2$—O—Si(CH$_3$)$_3$. A heteroalkyl moiety may include one heteroatom (e.g., o, n, s, si, or p). A heteroalkyl moiety may include two optionally different heteroatoms (e.g., o, n, s, si, or p). A heteroalkyl moiety may include three optionally different heteroatoms (e.g., o, n, s, si, or p). A heteroalkyl moiety may include four optionally different heteroatoms (e.g., o, n, s, si, or p). A heteroalkyl moiety may include five optionally different heteroatoms (e.g., o, n, s, si, or p). A heteroalkyl moiety may include up to 8 optionally different heteroatoms (e.g., o, n, s, si, or p).

The term "heteroalkenyl," by itself or in combination with another term, means, unless otherwise stated, a heteroalkyl including at least one double bond. A heteroalkenyl may optionally include more than one double bond and/or one or more triple bonds in additional to the one or more double bonds. The term "heteroalkynyl," by itself or in combination with another term, means, unless otherwise stated, a heteroalkyl including at least one triple bond. A heteroalkynyl may optionally include more than one triple bond and/or one or more double bonds in additional to the one or more triple bonds.

Similarly, the term "heteroalkylene," by itself or as part of another substituent, means, unless otherwise stated, a divalent radical derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—. As described above, heteroalkyl groups, as used herein, include those groups that are attached to the remainder of the molecule through a heteroatom, such as —C(O)R', —C(O)NR', —NR'R", —OR', —SR', and/or —SO$_2$R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The terms "cycloalkyl" and "heterocycloalkyl," by themselves or in combination with other terms, mean, unless otherwise stated, cyclic versions of "alkyl" and "heteroalkyl," respectively. Cycloalkyl and heterocycloalkyl are not aromatic. Additionally, for heterocycloalkyl, a heteroatom can occupy the position at which the heterocycle is attached to the remainder of the molecule. Examples of cycloalkyl include, but are not limited to, cyclopropyl, cyclobutyl, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent, means a divalent radical derived from a cycloalkyl and heterocycloalkyl, respectively.

In embodiments, the term "cycloalkyl" means a monocyclic, bicyclic, or a multicyclic cycloalkyl ring system. In embodiments, monocyclic ring systems are cyclic hydrocarbon groups containing from 3 to 8 carbon atoms, where such groups can be saturated or unsaturated, but not aromatic. In embodiments, cycloalkyl groups are fully saturated. Examples of monocyclic cycloalkyls include cyclopropyl, cyclobutyl, cyclopentyl, cyclopentenyl, cyclohexyl, cyclohexenyl, cycloheptyl, and cyclooctyl. Bicyclic cycloalkyl ring systems are bridged monocyclic rings or fused bicyclic rings. In embodiments, bridged monocyclic rings contain a monocyclic cycloalkyl ring where two non adjacent carbon atoms of the monocyclic ring are linked by an alkylene bridge of between one and three additional carbon atoms (i.e., a bridging group of the form (ch$_2$)$_w$, where w is 1, 2, or 3). Representative examples of bicyclic ring systems include, but are not limited to, bicyclo[3.1.1]heptane, bicyclo[2.2.1]heptane, bicyclo[2.2.2]octane, bicyclo[3.2.2] nonane, bicyclo[3.3.1]nonane, and bicyclo[4.2.1]nonane. In embodiments, fused bicyclic cycloalkyl ring systems contain a monocyclic cycloalkyl ring fused to either a phenyl, a monocyclic cycloalkyl, a monocyclic cycloalkenyl, a monocyclic heterocyclyl, or a monocyclic heteroaryl. In embodiments, the bridged or fused bicyclic cycloalkyl is attached to the parent molecular moiety through any carbon atom contained within the monocyclic cycloalkyl ring. In embodiments, cycloalkyl groups are optionally substituted with one or two groups which are independently oxo or thia. In embodiments, the fused bicyclic cycloalkyl is a 5 or 6 membered monocyclic cycloalkyl ring fused to either a phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the fused bicyclic cycloalkyl is optionally substituted by one or two groups which are independently oxo or thia. In embodiments, multicyclic cycloalkyl ring systems are a monocyclic cycloalkyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two other ring systems independently selected from the group consisting of a phenyl, a bicyclic aryl, a monocyclic or bicyclic heteroaryl, a monocyclic or bicyclic cycloalkyl, a monocyclic or bicyclic cycloalkenyl, and a monocyclic or bicyclic heterocyclyl. In embodiments, the multicyclic cycloalkyl is attached to the parent molecular moiety through any carbon atom contained within the base ring. In embodiments, multicyclic cycloalkyl ring systems are a monocyclic cycloalkyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two other ring systems independently selected from the group consisting of a phenyl, a monocyclic heteroaryl, a monocyclic cycloalkyl, a monocyclic cycloalkenyl, and a monocyclic heterocyclyl. Examples of multicyclic cycloalkyl groups include, but are not limited to tetradecahydrophenanthrenyl, perhydrophenothiazin-1-yl, and perhydrophenoxazin-1-yl.

In embodiments, a cycloalkyl is a cycloalkenyl. The term "cycloalkenyl" is used in accordance with its plain ordinary meaning. In embodiments, a cycloalkenyl is a monocyclic, bicyclic, or a multicyclic cycloalkenyl ring system. In embodiments, monocyclic cycloalkenyl ring systems are cyclic hydrocarbon groups containing from 3 to 8 carbon atoms, where such groups are unsaturated (i.e., containing at least one annular carbon carbon double bond), but not aromatic. Examples of monocyclic cycloalkenyl ring systems include cyclopentenyl and cyclohexenyl. In embodiments, bicyclic cycloalkenyl rings are bridged monocyclic rings or a fused bicyclic rings. In embodiments, bridged monocyclic rings contain a monocyclic cycloalkenyl ring where two non adjacent carbon atoms of the monocyclic ring are linked by an alkylene bridge of between one and three additional carbon atoms (i.e., a bridging group of the form $(ch_2)_w$, where w is 1, 2, or 3). Representative examples of bicyclic cycloalkenyls include, but are not limited to, norbornenyl and bicyclo[2.2.2]oct 2 enyl. In embodiments, fused bicyclic cycloalkenyl ring systems contain a monocyclic cycloalkenyl ring fused to either a phenyl, a monocyclic cycloalkyl, a monocyclic cycloalkenyl, a monocyclic heterocyclyl, or a monocyclic heteroaryl. In embodiments, the bridged or fused bicyclic cycloalkenyl is attached to the parent molecular moiety through any carbon atom contained within the monocyclic cycloalkenyl ring. In embodiments, cycloalkenyl groups are optionally substituted with one or two groups which are independently oxo or thia. In embodiments, multicyclic cycloalkenyl rings contain a monocyclic cycloalkenyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two ring systems independently selected from the group consisting of a phenyl, a bicyclic aryl, a monocyclic or bicyclic heteroaryl, a monocyclic or bicyclic cycloalkyl, a monocyclic or bicyclic cycloalkenyl, and a monocyclic or bicyclic heterocyclyl. In embodiments, the multicyclic cycloalkenyl is attached to the parent molecular moiety through any carbon atom contained within the base ring. In embodiments, multicyclic cycloalkenyl rings contain a monocyclic cycloalkenyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two ring systems independently selected from the group consisting of a phenyl, a monocyclic heteroaryl, a monocyclic cycloalkyl, a monocyclic cycloalkenyl, and a monocyclic heterocyclyl.

In embodiments, a heterocycloalkyl is a heterocyclyl. The term "heterocyclyl" as used herein, means a monocyclic, bicyclic, or multicyclic heterocycle. The heterocyclyl monocyclic heterocycle is a 3, 4, 5, 6 or 7 membered ring containing at least one heteroatom independently selected from the group consisting of O, N, and S where the ring is saturated or unsaturated, but not aromatic. The 3 or 4 membered ring contains 1 heteroatom selected from the group consisting of O, N and S. The 5 membered ring can contain zero or one double bond and one, two or three heteroatoms selected from the group consisting of O, N and S. The 6 or 7 membered ring contains zero, one or two double bonds and one, two or three heteroatoms selected from the group consisting of O, N and S. The heterocyclyl monocyclic heterocycle is connected to the parent molecular moiety through any carbon atom or any nitrogen atom contained within the heterocyclyl monocyclic heterocycle. Representative examples of heterocyclyl monocyclic heterocycles include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, piperazinyl, piperidinyl, pyranyl, pyrazolinyl, pyrazolidinyl, pyrrolinyl, pyrrolidinyl, tetrahydrofuranyl, tetrahydrothienyl, thiadiazolinyl, thiadiazolidinyl, thiazolinyl, thiazolidinyl, thiomorpholinyl, 1,1-dioxidothiomorpholinyl (thiomorpholine sulfone), thiopyranyl, and trithianyl. The heterocyclyl bicyclic heterocycle is a monocyclic heterocycle fused to either a phenyl, a monocyclic cycloalkyl, a monocyclic cycloalkenyl, a monocyclic heterocycle, or a monocyclic heteroaryl. The heterocyclyl bicyclic heterocycle is connected to the parent molecular moiety through any carbon atom or any nitrogen atom contained within the monocyclic heterocycle portion of the bicyclic ring system. Representative examples of bicyclic heterocyclyls include, but are not limited to, 2,3-dihydrobenzofuran-2-yl, 2,3-dihydrobenzofuran-3-yl, indolin-1-yl, indolin-2-yl, indolin-3-yl, 2,3-dihydrobenzothien-2-yl, decahydroquinolinyl, decahydroisoquinolinyl, octahydro-1h-indolyl, and octahydrobenzofuranyl. In embodiments, heterocyclyl groups are optionally substituted with one or two groups which are independently oxo or thia. In certain embodiments, the bicyclic heterocyclyl is a 5 or 6 membered monocyclic heterocyclyl ring fused to a phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the bicyclic heterocyclyl is optionally substituted by one or two groups which are independently oxo or thia. Multicyclic heterocyclyl ring systems are a monocyclic heterocyclyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two other ring systems independently selected from the group consisting of a phenyl, a bicyclic aryl, a monocyclic or bicyclic heteroaryl, a monocyclic or bicyclic cycloalkyl, a monocyclic or bicyclic cycloalkenyl, and a monocyclic or bicyclic heterocyclyl. The multicyclic heterocyclyl is attached to the parent molecular moiety through any carbon atom or nitrogen atom contained within the base ring. In embodiments, multicyclic heterocyclyl ring systems are a monocyclic heterocyclyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two other ring systems independently selected from the group consisting of a phenyl, a monocyclic heteroaryl, a monocyclic cycloalkyl, a monocyclic cycloalkenyl, and a monocyclic heterocyclyl. Examples of multicyclic heterocyclyl groups include, but are not limited to 10h-phenothiazin-10-yl, 9,10-dihydroacridin-9-yl, 9,10-dihydroacridin-10-yl, 10h-phenoxazin-10-yl, 10,11-dihydro-5h-dibenzo[b,f]azepin-5-yl, 1,2,3,4-tetrahydropyrido[4,3-g]isoquinolin-2-yl, 12h-benzo[b]phenoxazin-12-yl, and dodecahydro-1h-carbazol-9-yl.

The terms "halo" or "halogen," by themselves or as part of another substituent, mean, unless otherwise stated, a fluorine, chlorine, bromine, or iodine atom. Additionally, terms such as "haloalkyl" are meant to include monohaloalkyl and polyhaloalkyl. For example, the term "halo($c_1$-$c_4$) alkyl" includes, but is not limited to, fluoromethyl, difluoromethyl, trifluoromethyl, 2,2,2-trifluoroethyl, 4-chlorobutyl, 3-bromopropyl, and the like.

The term "acyl" means, unless otherwise stated, -c(o)r where r is a substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

The term "aryl" means, unless otherwise stated, a polyunsaturated, aromatic, hydrocarbon substituent, which can be a single ring or multiple rings (preferably from 1 to 3 rings) that are fused together (i.e., a fused ring aryl) or linked covalently. A fused ring aryl refers to multiple rings fused together wherein at least one of the fused rings is an aryl ring. The term "heteroaryl" refers to aryl groups (or rings) that contain at least one heteroatom such as O, N and S, wherein the nitrogen and sulfur atoms are optionally oxidized, and the nitrogen atom(s) are optionally quaternized. Thus, the term "heteroaryl" includes fused ring heteroaryl groups (i.e., multiple rings fused together wherein at least one of the fused rings is a heteroaromatic ring). A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, naphthyl, pyrrolyl, pyrazolyl, pyridazinyl, triazinyl, pyrimidinyl, imidazolyl, pyrazinyl, purinyl, oxazolyl, isoxazolyl, thiazolyl, furyl, thienyl, pyridyl, pyrimidyl, benzothiazolyl, benzoxazoyl benzimidazolyl, benzofuran, isobenzofuranyl, indolyl, isoindolyl, benzothiophenyl, isoquinolyl, quinoxalinyl, quinolyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. An "arylene" and a "heteroarylene," alone or as part of another substituent, mean a divalent radical derived from an aryl and heteroaryl, respectively. A heteroaryl group substituent may be -o- bonded to a ring heteroatom nitrogen.

A fused ring heterocyloalkyl-aryl is an aryl fused to a heterocycloalkyl. A fused ring heterocycloalkyl-heteroaryl is a heteroaryl fused to a heterocycloalkyl. A fused ring heterocycloalkyl-cycloalkyl is a heterocycloalkyl fused to a cycloalkyl. A fused ring heterocycloalkyl-heterocycloalkyl is a heterocycloalkyl fused to another heterocycloalkyl. Fused ring heterocycloalkyl-aryl, fused ring heterocycloalkyl-heteroaryl, fused ring heterocycloalkyl-cycloalkyl, or fused ring heterocycloalkyl-heterocycloalkyl may each independently be unsubstituted or substituted with one or more of the substitutents described herein.

Spirocyclic rings are two or more rings wherein adjacent rings are attached through a single atom. The individual rings within spirocyclic rings may be identical or different. Individual rings in spirocyclic rings may be substituted or unsubstituted and may have different substituents from other individual rings within a set of spirocyclic rings. Possible substituents for individual rings within spirocyclic rings are the possible substituents for the same ring when not part of spirocyclic rings (e.g. substituents for cycloalkyl or heterocycloalkyl rings). Spirocyclic rings may be substituted or unsubstituted cycloalkyl, substituted or unsubstituted cycloalkylene, substituted or unsubstituted heterocycloalkyl or substituted or unsubstituted heterocycloalkylene and individual rings within a spirocyclic ring group may be any of the immediately previous list, including having all rings of one type (e.g. all rings being substituted heterocycloalkylene wherein each ring may be the same or different substituted heterocycloalkylene). When referring to a spirocyclic ring system, heterocyclic spirocyclic rings means a spirocyclic rings wherein at least one ring is a heterocyclic ring and wherein each ring may be a different ring. When referring to a spirocyclic ring system, substituted spirocyclic rings means that at least one ring is substituted and each substituent may optionally be different.

The symbol "⌇" denotes the point of attachment of a chemical moiety to the remainder of a molecule or chemical formula.

The term "oxo," as used herein, means an oxygen that is double bonded to a carbon atom.

The term "alkylsulfonyl," as used herein, means a moiety having the formula —S(O$_2$)-r', where R' is a substituted or unsubstituted alkyl group as defined above. R' may have a specified number of carbons (e.g., "C$_1$-C$_4$ alkylsulfonyl").

The term "alkylarylene" as an arylene moiety covalently bonded to an alkylene moiety (also referred to herein as an alkylene linker). In embodiments, the alkylarylene group has the formula:

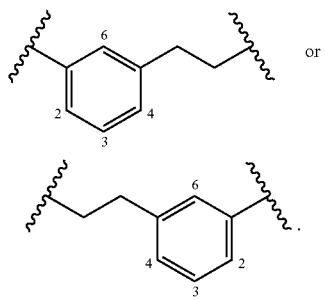

an alkylarylene moiety may be substituted (e.g. with a substituent group) on the alkylene moiety or the arylene linker (e.g. at carbons 2, 3, 4, or 6) with halogen, oxo, —N$_3$, —CF$_3$, —CCL$_3$, —CBR$_3$, —CI$_3$, —CN, —CHO, —OH, —NH$_2$, —COOH, —CONH$_2$, —NO$_2$, —SH, —SO$_2$CH$_3$—SO$_3$H, —OSO$_3$H, —SO$_2$NH$_2$, —NHNH$_2$, —ONH$_2$, —NHC(O)NHNH$_2$, substituted or unsubstituted C$_1$-C$_5$ alkyl or substituted or unsubstituted 2 to 5 membered heteroalkyl). In embodiments, the alkylarylene is unsubstituted.

Each of the above terms (e.g., "alkyl," "heteroalkyl," "cycloalkyl," "heterocycloalkyl," "aryl," and "heteroaryl") includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, —OR', =O, =NR', =N—OR', —NR'R", —SR', —HALOGEN, —SIR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —NR'NR"R'", —ONR'R", —NR'C(O)NR"NR'"R"", —CN, —NO$_2$, —NR'SO$_2$R", —NR'C(O)R", —NR'C(O)—OR", —NR'OR", in a number ranging from zero to (2m'+1), where m' is the total number of carbon atoms in such radical. R, R', R", R'", AND R"" each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted heteroaryl, substituted or unsubstituted alkyl, alkoxy, or thioalkoxy groups, or arylalkyl groups. When a compound described herein includes more than one R group, for example, each of the R groups is independently selected as are each R', R", R'", and R"" group when more than one of these groups is present. When R' and R" are attached to the same nitrogen atom, they can be combined with the nitrogen atom to form a 4-, 5-, 6-, or 7-membered ring. For example, —NR'R" includes, but is not limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ AND —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are varied and are selected from, for example: —OR', —NR'R", —SR', -halogen, —SIR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —NR'NR"R'", —ONR'R", —NR'C(O)NR'NR'"R"", —CN, —NO$_2$, —R', —N$_3$, —CH(PH)$_2$, fluoro(C$_1$-C$_4$)alkoxy, and fluoro(C$_1$-C$_4$)alkyl, —NR'SO$_2$R", —NR'C(O)R", —NR'C(O)—OR", —NR'OR", in a number ranging from zero to the total number of open valences on the aromatic ring system; and where R', R", R'", and R"" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. When a compound described herein includes more than one R group, for example, each of the R groups is independently selected as are each R', R", R'", and R"" groups when more than one of these groups is present.

Substituents for rings (e.g. cycloalkyl, heterocycloalkyl, aryl, heteroaryl, cycloalkylene, heterocycloalkylene, arylene, or heteroarylene) may be depicted as substituents on the ring rather than on a specific atom of a ring (commonly referred to as a floating substituent). In such a case, the substituent may be attached to any of the ring atoms (obeying the rules of chemical valency) and in the case of fused rings or spirocyclic rings, a substituent depicted as associated with one member of the fused rings or spirocyclic rings (a floating substituent on a single ring), may be a substituent on any of the fused rings or spirocyclic rings (a floating substituent on multiple rings). When a substituent is attached to a ring, but not a specific atom (a floating substituent), and a subscript for the substituent is an integer greater than one, the multiple substituents may be on the same atom, same ring, different atoms, different fused rings, different spirocyclic rings, and each substituent may optionally be different. Where a point of attachment of a ring to the remainder of a molecule is not limited to a single atom (a floating substituent), the attachment point may be any atom of the ring and in the case of a fused ring or spirocyclic ring, any atom of any of the fused rings or spirocyclic rings while obeying the rules of chemical valency. Where a ring, fused rings, or spirocyclic rings contain one or more ring heteroatoms and the ring, fused rings, or spirocyclic rings are shown with one more floating substituents (including, but not limited to, points of attachment to the remainder of the molecule), the floating substituents may be bonded to the heteroatoms. Where the ring heteroatoms are shown bound to one or more hydrogens (e.g. a ring nitrogen with two bonds to ring atoms and a third bond to a hydrogen) in the structure or formula with the floating substituent, when the heteroatom is bonded to the floating substituent, the substituent will be understood to replace the hydrogen, while obeying the rules of chemical valency.

Two or more substituents may optionally be joined to form aryl, heteroaryl, cycloalkyl, or heterocycloalkyl groups. Such so-called ring-forming substituents are typically, though not necessarily, found attached to a cyclic base structure. In one embodiment, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

Two of the substituents on adjacent atoms of the aryl or heteroaryl ring may optionally form a ring of the formula -t-C(O)—(CRR')$_Q$-u-, wherein t and u are independently —NR—, —O—, —CRR'—, or a single bond, and q is an integer of from 0 to 3. Alternatively, two of the substituents on adjacent atoms of the aryl or heteroaryl ring may optionally be replaced with a substituent of the formula -a-(CH$_2$)$_r$-b-, wherein a and b are independently —CRR'—, —O—, —NR—, —S—, —S(O)—, —S(O)$_2$—, —S(O)$_2$NR'—, or a single bond, and R is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$-x'—(C"R"R''')$_d$—, where s and d are independently integers of from 0 to 3, and x' is —O—, —NR'—, —S—, —S(O)—, —S(O)$_2$—, OR—S(O)$_2$NR'—. The substituents R, R', R", and R''' are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

As used herein, the terms "heteroatom" or "ring heteroatom" are meant to include oxygen (O), nitrogen (N), sulfur (S), phosphorus (P), and silicon (Si).

A "substituent group," as used herein, means a group selected from the following moieties:
  (a) oxo,
  halogen, —CCL$_3$, —CBR$_3$, —CF$_3$, —CI$_3$, —CH$_2$CL, —CH$_2$BR, —CH$_2$F, —CH$_2$I, —CHCL$_2$, —CHBR$_2$, —CHF$_2$, —CHI$_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCL$_3$, —OCF$_3$, —OCBR$_3$, —OCI$_3$, —OCHCL$_2$, —OCHBR$_2$, —OCHI$_2$, —OCHF$_2$, —N$_3$, unsubstituted alkyl (e.g., C$_1$-C$_8$ alkyl, C$_1$-C$_6$ alkyl, or C$_1$-C$_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., C$_3$-C$_5$ cycloalkyl, C$_3$-C$_6$ cycloalkyl, or C$_5$-C$_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., C$_6$-C$_{10}$ aryl, C$_{10}$ aryl, or phenyl), or unsubstituted heteroaryl (e.g., 5 to 10 membered heteroaryl, 5 to 9 membered heteroaryl, or 5 to 6 membered heteroaryl), and
   (b) alkyl (e.g., C$_1$-C$_8$ alkyl, C$_1$-C$_6$ alkyl, or C$_1$-C$_4$ alkyl), heteroalkyl (e.g., 2 to 8 membered heteroalkyl, 2 to 6 membered heteroalkyl, or 2 to 4 membered heteroalkyl), cycloalkyl (e.g., C$_3$-C$_8$ cycloalkyl, C$_3$-C$_6$ cycloalkyl, or C$_5$-C$_6$ cycloalkyl), heterocycloalkyl (e.g., 3 to 8 membered heterocycloalkyl, 3 to 6 membered heterocycloalkyl, or 5 to 6 membered heterocycloalkyl), aryl (e.g., C$_6$-C$_{10}$ aryl, C$_{10}$ aryl, or phenyl), heteroaryl (e.g., 5 to 10 membered heteroaryl, 5 to 9 membered heteroaryl, or 5 to 6 membered heteroaryl), substituted with at least one substituent selected from:
   (i) oxo,
   halogen, —CCL$_3$, —CBR$_3$, —CF$_3$, —CI$_3$, —CH$_2$CL, —CH$_2$BR, —CH$_2$F, —CH$_2$I, —CHCL$_2$, —CHBR$_2$, —CHF$_2$, —CHI$_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCL$_3$, —OCF$_3$, —OCBR$_3$, —OCI$_3$, —OCHCL$_2$, —OCHBR$_2$, —OCHI$_2$, —OCHF$_2$, —N$_3$, unsubstituted alkyl (e.g., C$_1$-C$_8$ alkyl, C$_1$-C$_6$ alkyl, or C$_1$-C$_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., C$_3$-C$_8$ cycloalkyl, C$_3$-C$_6$ cycloalkyl, or C$_5$-C$_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., C$_6$-C$_{10}$ aryl, C$_{10}$ aryl, or phenyl), or unsubstituted heteroaryl (e.g., 5 to 10 membered heteroaryl, 5 to 9 membered heteroaryl, or 5 to 6 membered heteroaryl), and
   (ii) alkyl (e.g., C$_1$-C$_8$ alkyl, C$_1$-C$_6$ alkyl, or C$_1$-C$_4$ alkyl), heteroalkyl (e.g., 2 to 8 membered heteroalkyl, 2 to 6 membered heteroalkyl, or 2 to 4 membered heteroalkyl), cycloalkyl (e.g., C$_3$-C$_8$ cycloalkyl, C$_3$-C$_6$ cycloalkyl, or C$_5$-C$_6$ cycloalkyl), heterocycloalkyl (e.g., 3 to 8 membered heterocycloalkyl, 3 to 6 membered heterocycloalkyl, or 5 to 6 membered heterocycloalkyl), aryl (e.g., C$_6$-C$_{10}$ aryl, C$_{10}$ aryl, or phenyl), heteroaryl (e.g., 5 to 10 membered heteroaryl, 5 to 9 membered heteroaryl, or 5 to 6 membered heteroaryl), substituted with at least one substituent selected from:
   (a) oxo, halogen, —CCL$_3$, —CBR$_3$, —CF$_3$, —CI$_3$, —CH$_2$CL, —CH$_2$BR, —CH$_2$F, —CH$_2$I, —CHCL$_2$, —CHBR$_2$, —CHF$_2$, —CHI$_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCL$_3$, —OCF$_3$, —OCBR$_3$, —OCI$_3$, —OCHCL$_2$, —OCHBR$_2$, —OCHI$_2$, —OCHF$_2$, —N$_3$, unsubstituted alkyl (e.g., C$_1$-C$_8$ alkyl, C$_1$-C$_6$ alkyl, or C$_1$-C$_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., C$_3$-C$_8$ cycloalkyl, C$_3$-C$_6$ cycloalkyl, or C$_5$-C$_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., C$_6$-C$_{10}$ aryl, C$_{10}$ aryl, or phenyl), or unsubstituted heteroaryl (e.g., 5 to 10 membered heteroaryl, 5 to 9 membered heteroaryl, or 5 to 6 membered heteroaryl), and
   (b) alkyl (e.g., C$_1$-C$_8$ alkyl, C$_1$-C$_6$ alkyl, or C$_1$-C$_4$ alkyl), heteroalkyl (e.g., 2 to 8 membered heteroalkyl, 2 to 6 membered heteroalkyl, or 2 to 4 membered heteroalkyl), cycloalkyl (e.g., C$_3$-C$_8$ cycloalkyl, C$_3$-C$_6$ cycloalkyl, or C$_5$-C$_6$ cycloalkyl), heterocycloalkyl (e.g., 3 to 8 membered heterocycloalkyl, 3 to 6 membered heterocycloalkyl, or 5 to 6 membered heterocycloalkyl), aryl (e.g., C$_6$-C$_{10}$ aryl, C$_{10}$ aryl, or phenyl), heteroaryl (e.g., 5 to 10 membered heteroaryl, 5 to 9 membered heteroaryl, or 5 to 6 membered heteroaryl), substituted with at least one substituent selected from: oxo, halogen, —CCL$_3$, —CBR$_3$, —CF$_3$, —CI$_3$, —CH$_2$CL, —CH$_2$BR, —CH$_2$F, —CH$_2$I, —CHCL$_2$, —CHBR$_2$, —CHF₂, —CHI₂, —CN, —OH, —NH₂, —COOH, —CONH₂, —NO₂, —SH, —SO₃H, —SO₄H, —SO₂NH₂, —NHNH₂, —ONH₂, —NHC(O)NHNH₂, —NHC(O)NH₂, —NHSO₂H, —NHC(O)H, —NHC(O)OH, —NHOH, —OCCL₃, —OCF₃, —OCBR₃, —OCI₃, —OCHCL₂, —OCHBR₂, —OCHI₂, —OCHF₂, —N₃, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl).

A "size-limited substituent" or "size-limited substituent group," as used herein, means a group selected from all of the substituents described above for a "substituent group," wherein each substituted or unsubstituted alkyl is a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and each substituted or unsubstituted heteroaryl is a substituted or unsubstituted 5 to 10 membered heteroaryl.

A "lower substituent" or "lower substituent group," as used herein, means a group selected from all of the substituents described above for a "substituent group," wherein each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted phenyl, and each substituted or unsubstituted heteroaryl is a substituted or unsubstituted 5 to 6 membered heteroaryl.

In some embodiments, each substituted group described in the compounds herein is substituted with at least one substituent group. More specifically, in some embodiments, each substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene described in the compounds herein are substituted with at least one substituent group. In other embodiments, at least one or all of these groups are substituted with at least one size-limited substituent group. In other embodiments, at least one or all of these groups are substituted with at least one lower substituent group.

In other embodiments of the compounds herein, each substituted or unsubstituted alkyl may be a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 10 membered heteroaryl. In some embodiments of the compounds herein, each substituted or unsubstituted alkylene is a substituted or unsubstituted $C_1$-$C_{20}$ alkylene, each substituted or unsubstituted heteroalkylene is a substituted or unsubstituted 2 to 20 membered heteroalkylene, each substituted or unsubstituted cycloalkylene is a substituted or unsubstituted $C_3$-$C_8$ cycloalkylene, each substituted or unsubstituted heterocycloalkylene is a substituted or unsubstituted 3 to 8 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 10 membered heteroarylene.

In some embodiments, each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 9 membered heteroaryl. Cn some embodiments, each substituted or unsubstituted alkylene is a substituted or unsubstituted $C_1$-$C_8$ alkylene, each substituted or unsubstituted heteroalkylene is a substituted or unsubstituted 2 to 8 membered heteroalkylene, each substituted or unsubstituted cycloalkylene is a substituted or unsubstituted $C_3$-$C_7$ cycloalkylene, each substituted or unsubstituted heterocycloalkylene is a substituted or unsubstituted 3 to 7 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 9 membered heteroarylene. In some embodiments, the compound is a chemical species set forth in the examples section, figures, or tables below.

In embodiments, a substituted or unsubstituted moiety (e.g., substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, substituted or unsubstituted alkylene, substituted or unsubstituted heteroalkylene, substituted or unsubstituted cycloalkylene, substituted or unsubstituted heterocycloalkylene, substituted or unsubstituted arylene, and/or substituted or unsubstituted heteroarylene) is unsubstituted (e.g., is an unsubstituted alkyl, unsubstituted heteroalkyl, unsubstituted cycloalkyl, unsubstituted heterocycloalkyl, unsubstituted aryl, unsubstituted heteroaryl, unsubstituted alkylene, unsubstituted heteroalkylene, unsubstituted cycloalkylene, unsubstituted heterocycloalkylene, unsubstituted arylene, and/or unsubstituted heteroarylene, respectively). In embodiments, a substituted or unsubstituted moiety (e.g., substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, substituted or unsubstituted alkylene, substituted or unsubstituted heteroalkylene, substituted or unsubstituted cycloalkylene, substituted or unsubstituted heterocycloalkylene, substituted or unsubstituted arylene, and/or substituted or unsubstituted heteroarylene) is substituted (e.g., is a substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene, respectively).

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one substituent group, wherein if the substituted moiety is substituted with a plurality of substituent groups, each substituent group may optionally be different. In embodiments, if the substituted moiety is substituted with a plurality of substituent groups, each substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one size-limited substituent group, wherein if the substituted moiety is substituted with a plurality of size-limited substituent groups, each size-limited substituent group may optionally be different. In embodiments, if the substituted moiety is substituted with a plurality of size-limited substituent groups, each size-limited substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one lower substituent group, wherein if the substituted moiety is substituted with a plurality of lower substituent groups, each lower substituent group may optionally be different. In embodiments, if the substituted moiety is substituted with a plurality of lower substituent groups, each lower substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one substituent group, size-limited substituent group, or lower substituent group; wherein if the substituted moiety is substituted with a plurality of groups selected from substituent groups, size-limited substituent groups, and lower substituent groups; each substituent group, size-limited substituent group, and/or lower substituent group may optionally be different. In embodiments, if the substituted moiety is substituted with a plurality of groups selected from substituent groups, size-limited substituent groups, and lower substituent groups; each substituent group, size-limited substituent group, and/or lower substituent group is different.

Certain compounds of the present disclosure possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)- or (S)- or, as (D)- or (L)- for amino acids, and individual isomers are encompassed within the scope of the present disclosure. The compounds of the present disclosure do not include those that are known in art to be too unstable to synthesize and/or isolate. The present disclosure is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both e and z geometric isomers.

As used herein, the term "isomers" refers to compounds having the same number and kind of atoms, and hence the same molecular weight, but differing in respect to the structural arrangement or configuration of the atoms.

The term "tautomer," as used herein, refers to one of two or more structural isomers which exist in equilibrium and which are readily converted from one isomeric form to another.

It will be apparent to one skilled in the art that certain compounds of this disclosure may exist in tautomeric forms, all such tautomeric forms of the compounds being within the scope of the disclosure.

Unless otherwise stated, structures depicted herein are also meant to include all stereochemical forms of the structure; i.e., the r and s configurations for each asymmetric center. Therefore, single stereochemical isomers as well as enantiomeric and diastereomeric mixtures of the present compounds are within the scope of the disclosure.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}$C- or $^{14}$C-enriched carbon are within the scope of this disclosure.

The compounds of the present disclosure may also contain unnatural proportions of atomic isotopes at one or more of the atoms that constitute such compounds. For example, the compounds may be radiolabeled with radioactive isotopes, such as for example tritium ($^{3}$H), iodine-125 ($^{125}$I), or carbon-14 ($^{14}$C). All isotopic variations of the compounds of the present disclosure, whether radioactive or not, are encompassed within the scope of the present disclosure.

It should be noted that throughout the application that alternatives are written in markush groups, for example, each amino acid position that contains more than one possible amino acid. It is specifically contemplated that each member of the markush group should be considered separately, thereby comprising another embodiment, and the markush group is not to be read as a single unit.

As used herein, the terms "bioconjugate" and "bioconjugate linker" refers to the resulting association between atoms or molecules of "bioconjugate reactive groups" or "bioconjugate reactive moieties". The association can be direct or indirect. For example, a conjugate between a first bioconjugate reactive group (e.g., —NH2, —C(O)OH, —N-hydroxysuccinimide, or -maleimide) and a second bioconjugate reactive group (e.g., sulfhydryl, sulfur-containing amino acid, amine, amine sidechain containing amino acid, or carboxylate) provided herein can be direct, e.g., by covalent bond or linker (e.g. a first linker of second linker), or indirect, e.g., by non-covalent bond (e.g. electrostatic interactions (e.g. ionic bond, hydrogen bond, halogen bond), van der waals interactions (e.g. dipole-dipole, dipole-induced dipole, london dispersion), ring stacking (pi effects), hydrophobic interactions and the like). In embodiments, bioconjugates or bioconjugate linkers are formed using bioconjugate chemistry (i.e. the association of two bioconjugate reactive groups) including, but are not limited to nucleophilic substitutions (e.g., reactions of amines and alcohols with acyl halides, active esters), electrophilic substitutions (e.g., enamine reactions) and additions to carbon-carbon and carbon-heteroatom multiple bonds (e.g., michael reaction, diels-alder addition). These and other useful reactions are discussed in, for example, March, Advanced Organic Chemistry, 3rd ed., John Wiley & sons, New York, 1985; Hermanson, Bioconjugate Techniques, Academic Press, Aan Diego, 1996; and Feeney et al., Modification of Proteins; Advances in Chemistry series, vol. 198, American Chemical Society, Washington, D.C., 1982. In embodiments, the first bioconjugate reactive group (e.g., maleimide moiety) is covalently attached to the second bioconjugate reactive group (e.g. a sulfhydryl). In embodiments, the first bioconjugate reactive group (e.g., haloacetyl moiety) is covalently attached to the second bioconjugate reactive group (e.g. a sulfhydryl). In embodiments, the first bioconjugate reactive group (e.g., pyridyl moiety) is covalently attached to the second bioconjugate reactive group (e.g. a sulfhydryl). In embodiments, the first bioconjugate reactive group (e.g., -n-hydroxysuccinimide moiety) is covalently attached to the second bioconjugate reactive group (e.g. an amine). In embodiments, the first bioconjugate reactive group (e.g., maleimide moiety) is covalently attached to the second bioconjugate reactive group (e.g. a sulfhydryl). In embodiments, the first bioconjugate reactive group (e.g., -sulfo-N-hydroxysuccinimide moiety) is covalently attached to the second bioconjugate reactive group (e.g. an amine).

Useful bioconjugate reactive moieties used for bioconjugate chemistries herein include, for example:

(a) carboxyl groups and various derivatives thereof including, but not limited to, N-hydroxysuccinimide esters, N-hydroxybenztriazole esters, acid halides, acyl imidazoles, thioesters, p-nitrophenyl esters, alkyl, alkenyl, alkynyl and aromatic esters;

(b) hydroxyl groups which can be converted to esters, ethers, aldehydes, etc.

(c) haloalkyl groups wherein the halide can be later displaced with a nucleophilic group such as, for example, an amine, a carboxylate anion, thiol anion, carbanion, or an alkoxide ion, thereby resulting in the covalent attachment of a new group at the site of the halogen atom;

(d) dienophile groups which are capable of participating in diels-alder reactions such as, for example, maleimido or maleimide groups;

(e) aldehyde or ketone groups such that subsequent derivatization is possible via formation of carbonyl derivatives such as, for example, imines, hydrazones, semicarbazones or oximes, or via such mechanisms as grignard addition or alkyllithium addition;

(f) sulfonyl halide groups for subsequent reaction with amines, for example, to form sulfonamides;

(g) thiol groups, which can be converted to disulfides, reacted with acyl halides, or bonded to metals such as gold, or react with maleimides;

(h) amine or sulfhydryl groups (e.g., present in cysteine), which can be, for example, acylated, alkylated or oxidized;

(i) alkenes, which can undergo, for example, cycloadditions, acylation, michael addition, etc;

(j) epoxides, which can react with, for example, amines and hydroxyl compounds;

(k) phosphoramidites and other standard functional groups useful in nucleic acid synthesis;

(l) metal silicon oxide bonding;

(m) metal bonding to reactive phosphorus groups (e.g. phosphines) to form, for example, phosphate diester bonds;

(n) azides coupled to alkynes using copper catalyzed cycloaddition click chemistry; and (o) biotin conjugate can react with avidin or strepavidin to form a avidin-biotin complex or streptavidin-biotin complex.

The bioconjugate reactive groups can be chosen such that they do not participate in, or interfere with, the chemical stability of the conjugate described herein. Alternatively, a reactive functional group can be protected from participating in the crosslinking reaction by the presence of a protecting group. In embodiments, the bioconjugate comprises a molecular entity derived from the reaction of an unsaturated bond, such as a maleimide, and a sulfhydryl group.

"Analog," or "analogue" is used in accordance with its plain ordinary meaning within chemistry and biology and refers to a chemical compound that is structurally similar to another compound (i.e., a so-called "reference" compound) but differs in composition, e.g., in the replacement of one atom by an atom of a different element, or in the presence of a particular functional group, or the replacement of one functional group by another functional group, or the absolute stereochemistry of one or more chiral centers of the reference compound. Accordingly, an analog is a compound that is similar or comparable in function and appearance but not in structure or origin to a reference compound.

The terms "a" or "an," as used in herein means one or more. In addition, the phrase "substituted with a[n]," as used herein, means the specified group may be substituted with one or more of any or all of the named substituents. For example, where a group, such as an alkyl or heteroaryl group, is "substituted with an unsubstituted $C_1$-$C_{20}$ alkyl, or unsubstituted 2 to 20 membered heteroalkyl," the group may contain one or more unsubstituted $C_1$-$C_{20}$ alkyls, and/or one or more unsubstituted 2 to 20 membered heteroalkyls.

Moreover, where a moiety is substituted with an R substituent, the group may be referred to as "R-substituted." where a moiety is R-substituted, the moiety is substituted with at least one R substituent and each R substituent is optionally different. Where a particular R group is present in the description of a chemical genus (such as formula (i)), a roman alphabetic symbol may be used to distinguish each appearance of that particular R group. For example, where multiple $R^1$ substituents are present, each $R^1$ substituent may be distinguished as $R^{1.A}$, $R^{1.B}$, $R^{1.C}$, $R^{3.D}$, etc., wherein each of $R^{1.A}$, $R^{1.B}$, $R^{1.C}$, $R^{1.D}$, etc., is defined within the scope of the definition of $R^1$ and optionally differently.

A "detectable agent" or "detectable moiety" is a composition, substance, element, or compound; or moiety thereof; detectable by appropriate means such as spectroscopic, photochemical, biochemical, immunochemical, chemical, magnetic resonance imaging, or other physical means. For example, useful detectable agents include $^{18}F$, $^{32}P$, $^{33}P$, $^{45}Ti$, $^{47}Sc$, $^{52}Fe$, $^{59}Fe$, $^{62}Cu$, $^{64}Cu$, $^{67}Cu$, $^{67}Ga$, $^{68}Ga$, $^{77}As$, $^{86}Y$, $^{90}Y$, $^{89}Sr$, $^{89}Zr$, $^{94}Tc$, $^{94}Tc$, $^{99M}Tc$, $^{99}Mo$, $^{105}Pd$, $^{105}Rh$, $^{111}Ag$, $^{111}In$, $^{123}I$, $^{124}I$, $^{125}I$, $^{131}I$, $^{142}Pr$, $^{143}Pr$, $^{149}Pm$, $^{153}Sm$, $^{154-158}Gd$, $^{161}Tb$, $^{166}Dy$, $^{166}Ho$, $^{169}Er$, $^{175}Lu$, $^{177}Lu$, $^{186}Re$, $^{188}Re$, $^{189}Re$, $^{194}Ir$, $^{198}Au$, $^{199}Au$, $^{211}At$, $^{211}Pb$, $^{212}Bi$, $^{212}Pb$, $^{213}Bi$, $^{223}Ra$, $^{225}Ac$, Cc, V, Mn, Fe, Co, Ni, Cu, La, Ce, Pr, Nd, Pm, Sm, Eu, Gd, Tb, Dy, Ho, Er, Tm, Yb, Lu, $^{32}P$, fluorophore (e.g. fluorescent dyes), electron-dense reagents, enzymes (e.g., as commonly used in an elisa), biotin, digoxigenin, paramagnetic molecules, paramagnetic nanoparticles, ultrasmall superparamagnetic iron oxide ("USPIO") nanoparticles, uspio nanoparticle aggregates, superparamagnetic iron oxide ("SPIO") nanoparticles, spio nanoparticle aggregates, monochrystalline iron oxide nanoparticles, monochrystalline iron oxide, nanoparticle contrast agents, liposomes or other delivery vehicles containing gadolinium chelate ("GD-Chelate") molecules, gadolinium, radioisotopes, radionuclides (e.g. Carbon-11, Nitrogen-13, Oxygen-15, Fluorine-18, Rubidium-82), fluorodeoxyglucose (e.g. Fluorine-18 labeled), any gamma ray emitting radionuclides, positron-emitting radionuclide, radiolabeled glucose, radiolabeled water, radiolabeled ammonia, biocolloids, microbubbles (e.g. including microbubble shells including albumin, galactose, lipid, and/or polymers; microbubble gas core including air, heavy gas(es), perfluorcarbon, nitrogen, octafluoropropane, perflexane lipid microsphere, perflutren, etc.), iodinated contrast agents (e.g. iohexol, iodixanol, ioversol, iopamidol, ioxilan, iopromide, diatrizoate, metrizoate, ioxaglate), barium sulfate, thorium dioxide, gold, gold nanoparticles, gold nanoparticle aggregates, fluorophores, two-photon fluorophores, or haptens and proteins or other entities which can be made detectable, e.g., by incorporating a radiolabel into a peptide or antibody specifically reactive with a target peptide. A detectable moiety is a monovalent detectable agent or a detectable agent capable of forming a bond with another composition.

Descriptions of compounds of the present disclosure are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

The term "leaving group" is used in accordance with its ordinary meaning in chemistry and refers to a moiety (e.g., atom, functional group, molecule) that separates from the molecule following a chemical reaction (e.g., bond formation, reductive elimination, condensation, cross-coupling reaction) involving an atom or chemical moiety to which the leaving group is attached, also referred to herein as the "leaving group reactive moiety", and a complementary reactive moiety (i.e. a chemical moiety that reacts with the leaving group reactive moiety) to form a new bond between the remnants of the leaving groups reactive moiety and the complementary reactive moiety. Thus, the leaving group reactive moiety and the complementary reactive moiety form a complementary reactive group pair. Non limiting examples of leaving groups include hydrogen, hydroxide, organotin moieties (e.g., organotin heteroalkyl), halogen (e.g., br), perfluoroalkylsulfonates (e.g. triflate), tosylates, mesylates, water, alcohols, nitrate, phosphate, thioether, amines, ammonia, fluoride, carboxylate, phenoxides, boronic acid, boronate esters, and alkoxides. In embodiments, two molecules with leaving groups are allowed to contact, and upon a reaction and/or bond formation (e.g., acyloin condensation, aldol condensation, claisen condensation, stille reaction) the leaving groups separates from the respective molecule. In embodiments, a leaving group is a bioconjugate reactive moiety. In embodiments, at least two leaving groups are allowed to contact such that the leaving groups are sufficiently proximal to react, interact or physically touch. In embodiments, the leaving groups is designed to facilitate the reaction.

The term "protecting group" is used in accordance with its ordinary meaning in organic chemistry and refers to a moiety covalently bound to a heteroatom, heterocycloalkyl, or heteroaryl to prevent reactivity of the heteroatom, heterocycloalkyl, or heteroaryl during one or more chemical reactions performed prior to removal of the protecting group. Typically a protecting group is bound to a heteroatom (e.g., O) during a part of a multipart synthesis wherein it is not desired to have the heteroatom react (e.g., a chemical reduction) with the reagent. Following protection the protecting group may be removed (e.g., by modulating the ph). In embodiments the protecting group is an alcohol protecting group. Non-limiting examples of alcohol protecting groups include acetyl, benzoyl, benzyl, methoxymethyl ether (mom), tetrahydropyranyl (thp), and silyl ether (e.g., trimethylsilyl (TMS)). In embodiments the protecting group is an amine protecting group. Non-limiting examples of amine protecting groups include carbobenzyloxy (cbz), tert-butyloxycarbonyl (BOC), 9-fluorenylmethyloxycarbonyl (FMOC), acetyl, benzoyl, benzyl, carbamate, p-methoxybenzyl ether (PMB), and tosyl (TS).

A person of ordinary skill in the art will understand when a variable (e.g., moiety or linker) of a compound or of a compound genus (e.g., a genus described herein) is described by a name or formula of a standalone compound with all valencies filled, the unfilled valence(s) of the variable will be dictated by the context in which the variable is used. For example, when a variable of a compound as described herein is connected (e.g., bonded) to the remainder of the compound through a single bond, that variable is understood to represent a monovalent form (i.e., capable of forming a single bond due to an unfilled valence) of a standalone compound (e.g., if the variable is named "methane" in an embodiment but the variable is known to be attached by a single bond to the remainder of the compound, a person of ordinary skill in the art would understand that the variable is actually a monovalent form of methane, i.e., methyl or —CH$_3$). Likewise, for a linker variable (e.g., L$^1$, L$^2$, or L$^3$ as described herein), a person of ordinary skill in the art will understand that the variable is the divalent form of a standalone compound (e.g., if the variable is assigned to "PEG" or "polyethylene glycol" in an embodiment but the variable is connected by two separate bonds to the remainder of the compound, a person of ordinary skill in the art would understand that the variable is a divalent (i.e., capable of forming two bonds through two unfilled valences) form of PEG instead of the standalone compound PEG).

The term "exogenous" refers to a molecule or substance (e.g., a compound, nucleic acid or protein) that originates from outside a given cell or organism. For example, an "exogenous promoter" as referred to herein is a promoter that does not originate from the plant it is expressed by. Conversely, the term "endogenous" or "endogenous promoter" refers to a molecule or substance that is native to, or originates within, a given cell or organism.

The term "lipid moiety" is used in accordance with its ordinary meaning in chemistry and refers to a hydrophobic molecule which is typically characterized by an aliphatic hydrocarbon chain. In embodiments, the lipid moiety includes a carbon chain of 3 to 100 carbons. In embodiments, the lipid moiety includes a carbon chain of 5 to 50 carbons. In embodiments, the lipid moiety includes a carbon chain of 5 to 25 carbons. In embodiments, the lipid moiety includes a carbon chain of 8 to 525 carbons. Lipid moieties may include saturated or unsaturated carbon chains, and may be optionally substituted. In embodiments, the lipid moiety is optionally substituted with a charged moiety at the terminal end. In embodiments, the lipid moiety is an alkyl or heteroalkyl optionally substituted with a carboxylic acid moiety at the terminal end.

A charged moiety refers to a functional group possessing an abundance of electron density (i.e. electronegative) or is deficient in electron density (i.e. electropositive). Non-limiting examples of a charged moiety includes carboxylic acid, alcohol, phosphate, aldehyde, and sulfonamide. In embodiments, a charged moiety is capable of forming hydrogen bonds.

The term "coupling reagent" is used in accordance with its plain ordinary meaning in the arts and refers to a substance (e.g., a compound or solution) which participates in chemical reaction and results in the formation of a covalent bond (e.g., between bioconjugate reactive moieties, between a bioconjugate reactive moiety and the coupling reagent). In embodiments, the level of reagent is depleted in the course of a chemical reaction. This is in contrast to a solvent, which typically does not get consumed over the course of the chemical reaction. Non-limiting examples of coupling reagents include benzotriazol-1-yl-oxytripyrrolidinophosphonium hexafluorophosphate (PYBOP), 7-azabenzotriazol-1-yloxy)tripyrrolidinophosphonium hexafluorophosphate (PYAOP), 6-chloro-benzotriazole-1-yloxy-tris-pyrrolidinophosphonium hexafluorophosphate (PYCLOCK), 1-[bis(dimethylamino)methylene]-1h-1,2,3-triazolo[4,5-b]pyridinium 3-oxid hexafluorophosphate (HATU), or 2-(1h-benzotriazol-1-yl)-1,1,3,3-tetramethyluronium hexafluorophosphate (HBTU).

The term "solution" is used in accord and refers to a liquid mixture in which the minor component (e.g., a solute or compound) is uniformly distributed within the major component (e.g., a solvent).

The term "organic solvent" as used herein is used in accordance with its ordinary meaning in chemistry and refers to a solvent which includes carbon. Non-limiting examples of organic solvents include acetic acid, acetone, acetonitrile, benzene, 1-butanol, 2-butanol, 2-butanone, t-butyl alcohol, carbon tetrachloride, chlorobenzene, chloroform, cyclohexane, 1,2-dichloroethane, diethylene glycol, diethyl ether, diglyme (diethylene glycol, dimethyl ether), 1,2-dimethoxyethane (GLYME, DME), dimethylformamide (DMF), dimethyl sulfoxide (DMSO), 1,4-dioxane, ethanol, ethyl acetate, ethylene glycol, glycerin, heptane, hexamethylphosphoramide (HMPA), hexamethylphosphorous, triamide (HMPT), hexane, methanol, methyl t-butyl ether (MTBE), methylene chloride, n-methyl-2-pyrrolidinone (NMP), nitromethane, pentane, petroleum ether (LIGROINE), 1-propanol, 2-propanol, pyridine, tetrahydrofuran (THF), toluene, triethyl amine, o-xylene, m-xylene, or p-xylene. In embodiments, the organic solvent is or includes chloroform, dichloromethane, methanol, ethanol, tetrahydrofuran, or dioxane.

As used herein, the term "salt" refers to acid or base salts of the compounds used in the methods of the present invention. Illustrative examples of acceptable salts are mineral acid (hydrochloric acid, hydrobromic acid, phosphoric acid, and the like) salts, organic acid (acetic acid, propionic acid, glutamic acid, citric acid and the like) salts, quaternary ammonium (methyl iodide, ethyl iodide, and the like) salts.

The terms "bind" and "bound" as used herein is used in accordance with its plain and ordinary meaning and refers to the association between atoms or molecules. The association can be direct or indirect. For example, bound atoms or molecules may be bound, e.g., by covalent bond, linker (e.g. a first linker or second linker), or non-covalent bond (e.g. electrostatic interactions (e.g. ionic bond, hydrogen bond, halogen bond), Van der Waals interactions (e.g. dipole-dipole, dipole-induced dipole, london dispersion), ring stacking (pi effects), hydrophobic interactions and the like).

The term "capable of binding" as used herein refers to a moiety (e.g. a compound as described herein) that is able to measurably bind to a target (e.g., a NF-KB, a toll-like receptor protein). In embodiments, where a moiety is capable of binding a target, the moiety is capable of binding with a Kd of less than about 10 µm, 5 µm, 1 µm, 500 nm, 250 nm, 100 nm, 75 nm, 50 nm, 25 nm, 15 nm, 10 nm, 5 nm, 1 nm, or about 0.1 nm.

As used herein, the term "conjugated" when referring to two moieties means the two moieties are bonded, wherein the bond or bonds connecting the two moieties may be covalent or non-covalent. In embodiments, the two moieties are covalently bonded to each other (e.g. directly or through a covalently bonded intermediary). In embodiments, the two moieties are non-covalently bonded (e.g. through ionic bond(s), Van der Waal's bond(s)/interactions, hydrogen bond(s), polar bond(s), or combinations or mixtures thereof).

The term "non-nucleophilic base" as used herein refers to any sterically hindered base that is a poor nucleophile.

The term "nucleophile" as used herein refers to a chemical species that donates an electron pair to an electrophile to form a chemical bond in relation to a reaction. All molecules or ions with a free pair of electrons or at least one pi bond can act as nucleophiles.

The term "strong acid" as used herein refers to an acid that is completely dissociated or ionized in an aqueous solution. Examples of common strong acids include hydrochloric acid (HCL), nitric acid ($HNO_3$), sulfuric acid ($H_2SO_4$), hydrobromic acid (HBR), hydroiodic acid (HI), perchloric acid ($HCLO_4$), or chloric acid ($HCLO_3$).

The term "carbocation stabilizing solvent" as used herein refers to any polar protic solvent capable of forming dipole-dipole interactions with a carbocation, thereby stabilizing the carbocation.

As used herein, the terms "subject", "patient", and "individual" are used interchangeably to refer to humans and non-human animals. The term "non-human animal" includes all vertebrates, e.g., mammals and non-mammals, such as non-human primates, horses, sheep, dogs, cows, pigs, chickens, and other veterinary subjects and test animals. In some embodiments of the present invention, the subject is a mammal. In some embodiments of the present invention, the subject is a human.

The use of the singular can include the plural unless specifically stated otherwise. As used in the specification and the appended claims, the singular forms "a", "an", and "the" can include plural referents unless the context clearly dictates otherwise.

As used herein, "and/or" means "and" or "or". For example, "A and/or B" means "A, B, or both A and B" and "A, B, C, and/or D" means "A, B, C, D, or a combination thereof" and said "A, B, C, D, or a combination thereof" means any subset of A, B, C, and D, for example, a single member subset (e.g., A or B or C or D), a two-member subset (e.g., A and B; A and C; etc.), or a three-member subset (e.g., A, B, and C; or A, B, and D; etc.), or all four members (e.g., A, B, C, and D).

As used herein, the phrase "one or more of", e.g., "one or more of A, B, and/or C" means "one or more of A", "one or more of B", "one or more of C", "one or more of A and one or more of B", "one or more of B and one or more of C", "one or more of A and one or more of C" and "one or more of A, one or more of B, and one or more of C".

The phrase "comprises, consists essentially of, or consists of A" is used as a tool to avoid excess page and translation fees and means that in some embodiments the given thing at issue: comprises A, consists essentially of A, or consists of A. For example, the sentence "In some embodiments, the composition comprises, consists essentially of, or consists of A" is to be interpreted as if written as the following three separate sentences: "In some embodiments, the composition comprises A. In some embodiments, the composition consists essentially of A. In some embodiments, the composition consists of A."

Similarly, a sentence reciting a string of alternates is to be interpreted as if a string of sentences were provided such that each given alternate was provided in a sentence by itself. For example, the sentence "in some embodiments, the composition comprises A, B, or C" is to be interpreted as if written as the following three separate sentences: "In some embodiments, the composition comprises A. In some embodiments, the composition comprises B. In some embodiments, the composition comprises C." As another example, the sentence "in some embodiments, the composition comprises at least A, B, or C" is to be interpreted as if written as the following three separate sentences: "In some embodiments, the composition comprises at least A. In some embodiments, the composition comprises at least B. In some embodiments, the composition comprises at least C."

As used herein, the terms "PEG-DPCA hydrogel" and "PEG-DPCA gel" are used interchangeably to refer to a sol-gel that comprises one or more PEG-DPCA conjugates. As used herein, "PEG-DPCA conjugates" refers to a PEG compound having one or more terminal DPCA groups at one or both ends. As used herein "sol-gel" refers to a hydrogel that exhibits a reversible transition from a solid gel to a liquid through either heating/cooling or through the application of shear stress, or a combination of heating and shear stress.

As used herein, a "DPCA group" refers to a chemical moiety having

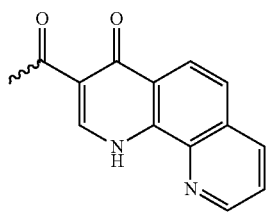

as part of its backbone, wherein ⁓ is a bond and one or more of the hydrogens may be substituted. Alternatively, the DPCA group may be presented herein as:

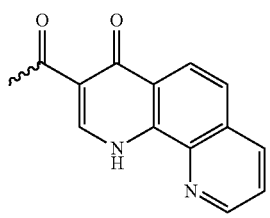

wherein ⁓ represents the point of attachment to the remainder of the compound.

In some embodiments, a PEG-DPCA hydrogel has the formula $X_m$-PEG(A)-$X_p$, where X is DPCA, m and p represent the number of DPCA molecules at each end (flanking the PEG) and m plus p is equal to or greater than 1 and wherein (A) describes the type of PEG compound.

As used herein, the terms "PEG compound" or "PEG group" or "PEG linker" are used interchangeably and refer to a polyether compound having

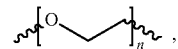

wherein n>1 and ⁓ is a bond, as part of its structural formula. Alternatively, the PEG compound presented herein as:

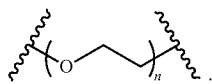

The variable n, as used herein, is 1 to 1000. In embodiments, n is 1 to 500. In embodiments, n is 1 to 250. In embodiments, n is 10 to 200. A number following the term "PEG" is used to indicate the average molecular weight of the PEG compound, e.g., "PEG8000" denotes a PEG compound having an average molecular weight of 8,000 Da. As used herein, "P80" is sometimes used as an abbreviation for PEG8000 and "P7" is sometimes used as an abbreviation for PEG750 (i.e., a PEG compound having an average molecular weight of 750 Da).

In some embodiments of the PEG-DPCA hydrogel, m is 0, 1, 2, 3, 4, 5, 6, or more than 6. In some embodiments of the PEG-DPCA hydrogel, when m is 0, p is 1 or greater than 1, or when m is 1, p is 2 or greater than 2 and when m is 3 or more than 3, p is 0, 1, 2, 3, 4, 5, 6, or more 6. In some embodiments of the PEG-DPCA hydrogel, when m is 0, p is 2 or greater than 2, and when m is 1, p is 1 or greater than 1.

As disclosed herein, PEG-DPCA hydrogels can induce, improve, enhance, or increase tissue regeneration and/or cellular repair in a subject when administered to the subject at a local site or a distal site specifically, subcutaneous injection of PEG-DPCA hydrogels in the back of mice wounded with a critical-sized defect in the ear led to transient upregulation of hypoxia-inducible factor 1α (HIF-1α) and regeneration of ear tissue in a manner reminiscent of epimorphic regeneration. Additionally, regeneration of jaw bone in aged mice was observed after treatment with PEG-DPCA hydrogels. Tissue regeneration by administration of a PEG-DPCA hydrogel to a remote eliminates the need for delivery of biologics (e.g., growth factors, cells, etc.), and avoids the administration of a foreign material or tissue graft directly to the tissue to be treated.

As used herein, "epimorphic regeneration" refers to a complete (or substantially complete) replication of the full structural and functional complexity of the original tissue. At the end of this process, a wound is virtually indistinguishable from the previously unwounded state. Here many tissue types including muscle, nerve, vasculature, cartilage, hair follicles, and bone can be involved, depending on the area of the body and the animal involved. Biological response to a naturally occurring or surgically created wound in animals generally results in one of two mutually exclusive outcomes: wound repair or regeneration. "Wound repair", a more typical response, is characterized by some growth of tissue and scarring over the defects with no attempt to recreate the original structure or function. "Tissue regeneration" is a subset of healing in which a single tissue type can regrow without scarring.

The process of epimorphic regeneration begins after a wound is made. An extremely rapid wound covering by the epidermis occurs which is followed by the formation of the blastema, a structure that is formed from local cells and in-migrating cells into the wound site. This is happening at the time that there is local tissue breakdown or remodeling to allow renewed cell accumulation from local sites by setting cells free of their matrix and the laying down of new matrix structures. In the blastema, the de-differentiation of accumulated cells to a more immature state (the cells now expressing stem cell markers), then the proliferation of these cells, and the re-differentiation of cells into their final mature state in the appropriate 3D location allows perfect structure and function. As provided herein, the compositions of PEG-DPCA hydrogels comprising PEG-DPCA conjugates, and methods of using these compositions promote epimorphic regeneration.

As disclosed herein, PEG-DPCA hydrogels comprising PEG-DPCA conjugates, which have multiple hydrophobic DPCA groups at one terminal end or at both terminal ends of a PEG compound, exploits DPCA as both a structure-directing agent and a therapeutic agent. Weak and reversible hydrophobic interactions between the DPCA groups enable the hydrogels to flow under applied shear stress and to recover completely and immediately to the gel state when the stress is removed. The PEG-DPCA hydrogels have high DPCA loading which is released by ester hydrolysis and the released DPCA results in HIF-1α stabilization and tissue regeneration of a variety of tissues including cartilage and cardiac tissue in otherwise non-healing mice. Therefore, PEG-DPCA hydrogels may be used for tissue regeneration of a variety of different tissues in subjects.

Conjugates

The term "biomacromolecule" as used herein refers to a compound that may be of synthetic origin or produced by a biological process, that is compatible with administration to an animal (such as a mammal or a human), that is covalently joined to one or more DPCA groups. In embodiments, the biomacromolecule is capable as a conjugate with the DPCA of forming a supramolecular polymer structure. In embodiments, the conjugate is capable of releasing DPCA subsequent to administration.

The terms "biomacromolecule," "biomolecule", "macromolecule" and "polymer" may be used interchangeably herein.

In embodiments, the conjugation of DPCA to the biomacromolecule forms a supramolecular therapeutic, whereby the DPCA acts both as a regeneration-inducing therapeutic and a structure-directing agent for the supramolecular polymer structure. In embodiments, the conjugation of DPCA to the biomacromolecule creates a supramolecular polymer that forms a shear-thinning nanofiber hydrogel. In embodiments, the supramolecular polymer hydrogel has shear-thinning properties to facilitate administration by simple injection. In embodiments, the supramolecular polymer hydrogel formed from conjugation of the biomacromolecule and DPCA group(s) has a high drug loading capacity. In embodiments, the supramolecular polymer hydrogel formed from conjugation of the biomacromolecule and DPCA group(s) decomposes in vivo to produce only DPCA and biomacromolecule, for example decomposes to DPCA and PEG.

In embodiments, the biomacromolecule may include, but is not limited to, a PEG, PEG-PPO block copolymer, dextran, alginate, hyaluronic acid, cyclodextrins, cellulose, hydroxypropylcellulose, chitosan, gelatin, PGA/PLA/PCL and copolymers thereof, PGA/PLA/PCL block copolymers with PEG, poly(acrylic acid), poly(methacrylic acid), poly (vinyl alcohol), poly(hydroxyethyl methacrylate), and/or poly(N-isopropyl acrylamide) (PNIPAAm). In embodiments, the biomacromolecule is or may include a linear PEG, branched PEG, multiarm PEG, or star PEG. In embodiments, the biomacromolecule is or includes a PEG that has an average molecular weight of about 250-20,000 Da, about 300-10,000 Da, about 400-9,000 Da, or about 500-8,000 Da.

In embodiments, weak and reversible hydrophobic interactions between DPCA domains in the conjugate of DPCA and biomacromolecule enable the hydrogel to flow under applied shear stress and to recover to the gel state when the stress is removed. In embodiments, a biomacromolecule is selected for the conjugate and joined to DPCA in a manner that is capable of releasing DPCA by hydrolysis, such as ester hydrolysis, and/or hydrolysis in vivo.

Polyethylene glycol (PEG) is a chemical compound that contains polyether. In embodiments, PEG may function as an osmotic laxative. In embodiments, the PEG compound presented herein is:

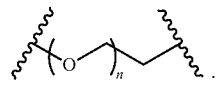

The variable n, as used herein, is an integer greater than 1. In embodiments, the variable n is an integer from 1 to 100,000,000**.

A number following the term "PEG" is used to indicate the average molecular weight of the PEG compound, e.g., "PEG8000" denotes a PEG compound having an average molecular weight of 8,000 Da. As used herein, "P80" is sometimes used as an abbreviation for PEG8000 and "P7" is sometimes used as an abbreviation for PEG750 (i.e., a PEG compound having an average molecular weight of 750 Da).

Poly(ethylene glycol)-block-poly(propylene glycol)-block-poly(ethylene glycol) (PEG-PPO block copolymer) is used according to its ordinary meaning in the art and refers to a symmetric triblock copolymer consisting of poly(ethylene oxide)(PEO) and poly (propylene oxide) (PPO). In embodiments, the PPO block is hydrophobic at temperatures above 288K and soluble in water at temperatures below 288K. In embodiments, the combination of properties leads to formation of micelle consisting of PEO-PPO-PEO triblock copolymers.

Dextran is used according to its ordinary meaning in the art and refers to a water-soluble complex branched glucan (made of monosaccharide glucose molecules) composed of chains of varying lengths (e.g. from 3 to 2000 kilodaltons). In embodiments, the polymer main chain includes α-1,6 glycosidic linkages between glucose monomers, with branches from α-1,3 linkages.

Alginate or alginic acid are used according to their ordinary meaning in the art and refers to a copolymer with homopolymeric blocks of (1-4)-linked β-D-mannuronate (M) and α-L-guluronate (G) residues, respectively, covalently linked together in different sequences or blocks.

Hyaluronic acid is used according to its ordinary meaning and refers to a polymer of disaccharides, wherein each disaccharide includes a D-glucoronic acid and N-acetyl-D-glucosaomine kined through alternating beta-(1-4) and beta-(1-3) glycosidic bonds.

Cyclodextrin is used according to its ordinary meaning and refers to a cyclic oligosaccharides consisting of a ring of glucose subunits joined by α-1,4 glycosidic bonds.

Cellulose is used according to its plain meaning and refers to a polysaccharide consisting of a linear chain of β(1→4) linked D-glucose units.

Hydroxypropylcellulose is used according to its plain meaning and refers to an ether of cellulose in which a portion of the hydroxyl groups in the repeating glucose units have been hydroxypropylated forming —OCH$_2$CH(OH)CH$_3$ groups (e.g. using propylene oxide).

Chitosan is used according to its plain meaning and refers to a linear polysaccharide composed of freely distributed beta (1→4)-linked D-glucosamine (deacetylated unit) and N-acetyl-D-glucosamine (acetylated unit).

Gelatin is used according to its plain meaning and refers to a substance obtained by partial hydrolysis of collagen (e.g. derived from skin or white connective tissue).

PLA is used according to its plain meaning and refers to a polyester polymer of poly lactic acid (PLA), which contains an asymmetric α-carbon. PGA is used according to its plain meaning and refers to a polyester polymer of poly glycolic acid (PGA). PCL is used according to its plain meaning and refers to a polymer of poly(F-caprolactone). PLGA is used according to its plain meaning and refers to a copolymer of poly lactic acid (PLA) and poly glycolic acid (PGA).

PGA/PLA/PCL and copolymers thereof is used according to its plain meaning and refers to a polymer combining block sections of PLA, PGA and PCL, optionally containing additional copolymers. Where the coppolyer contains a PEG, it may be referred to herein as a PGA/PLA/PCL block copolymers with PEG.

Poly(acrylic acid) or poly(1-carboxyethylene) is used according to its plain meaning and includes a polymer of acrylic acid (e.g. synthetic high-molecular weight). The polymer may be a homopolymer of acrylic acid, or cross-linked with an allyl ether of pentaerythritol, allyl ether of sucrose, or allyl ether of propylene.

Poly(methacrylic acid) is used according to its plain meaning and refers to a polymer of methacrylic acid.

Poly(vinyl alcohol) is used according to its plain meaning and includes polymers with a repeating —(CH$_2$—CH(OH)— subunit.

Poly-2-hydroxyethyl methacrylate (polyHEMA) is used according to its plain meaning and refers to a polymer containing a repeating subunit of —(CH$_2$—C(CH$_3$)(C(O)—O—CH$_2$CH$_2$OH))—.

Poly(N-isopropylacrylamide) (PNIPAAm) is used according to its plain meaning and includes polymers synthesized from N-isopropylacrylamide via free-radical polymerization and/or polymers including a repeating —(CH$_2$—CH(C(O)NHCH(CH$_3$)$_2$)— subunit.

In embodiments, a conjugate comprises a biomacromolecule and a first DPCA group, wherein the biomacromolecule comprises a first terminal end and a second terminal end, and wherein the first DPCA group is covalently joined directly or indirectly to the first terminal end or the second terminal end.

In embodiments, the conjugate further comprising a second DPCA group covalently joined directly or indirectly to the first terminal end or the second terminal end. In embodiments, the DPCA is covalently joined to the biomacromolecule by a linker. In embodiments, the linker is capable of in vivo cleavage. In embodiments, the cleavage is hydrolytic cleavage.

In embodiments, the linker comprises a group selected from the group consisting of ester, anhydride, peptide, thioester, hydrazine, disulfide, azo, Schiff bases and acetal.

In embodiments, the linker has the formula -L$^1$-L$^2$-L$^3$-. In embodiments, the linker -L$^1$-L$^2$-L$^3$- is a cleavable linker. In embodiments, -L$^1$-L$^2$-L$^3$- is the linker cleavable by an esterase.

In embodiments, the conjugate has the formula (X-L$^3$-L$^2$-L$^1$)$_{n2}$-A. In embodiments, the conjugate has the formula (X-L$^3$-L$^2$)$_{n2}$-L$^1$-A. In embodiments, the conjugate has the formula (X-L$^3$-L$^2$-L$^1$)$_{n2}$-A-(L$^1$-L$^2$-L$^3$-X)$_{n3}$. In embodiments, the conjugate has the formula (X-L$^{3,4}$-L$^{2,4}$-L$^{1,4}$)$_{n2}$-A-(L$^1$-L$^2$-L$^3$-X)$_{n3}$. In embodiments, the conjugate has the formula (X-L$^3$-L$^2$)$_{n2}$-L$^1$-A-L$^1$-(L$^2$-L$^3$-X)$_{n3}$. In embodiments, the conjugate has the formula (X-L$^{3,4}$-L$^{2,4}$) -L$^{1,4}$-A-L$^1$-(L$^2$-L$^3$-X)$_{n3}$. In embodiments, X is a DPCA group. In embodiments, the variables n2 and n3 are independently integers from 1 to 10. In embodiments, A is a biomacromolecule.

L$^1$ and L$^3$ are independently a bond, —O—, —S—, —NH—, —C(O)NH—, —C(O)—, —S(O)$_{n1}$NH—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. The variable n1 is an integer from 1 to 3. L$^{1,4}$ and L$^{3,4}$ are independently a bond, —O—, —S—, —NH—, —C(O)NH—, —C(O)—, —S(O)$_{n10}$NH—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. The variable n10 is independently an integer from 1 to 3

L$^2$ is —C(O)O—, —C(O)—O—C(O)—, a peptide linker, —C(O)S—, —NH—NH—, —S—S—, —N=N—, —C(N(R$^1$))—, —C(OR$^2$)(OR$^3$)—, wherein R$^1$, R$^2$, and R$^3$ are independently substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. L$^{2,4}$ is —C(O)O—, —C(O)—O—C(O)—, a peptide linker, —C(O)S—, —NH—NH—, —S—S—, —N=N—, —C(N(R$^{1,4}$))—, —C(OR$^{2,4}$)(OR$^{3,4}$)—, wherein R$^{1,4}$, R$^{2,4}$, and R$^{3,4}$ are independently substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In embodiments, L$^1$ is independently a bond, —O—, —S—, —NH—, —C(O)NH—, —C(O)—, —S(O)$_{n1}$NH—, substituted (e.g., substituted with a substituent group, a size-limited substituent group, or lower substituent group) or unsubstituted alkylene (e.g., C$_1$-C$_8$, C$_1$-C$_6$, or C$_1$-C$_4$), substituted (e.g., substituted with a substituent group, a size-limited substituent group, or lower substituent group) or unsubstituted heteroalkylene (e.g., 2 to 8 membered, 2 to 6 membered, or 2 to 4 membered), substituted (e.g., substituted with a substituent group, a size-limited substituent group, or lower substituent group) or unsubstituted cycloalkylene (e.g., C$_3$-C$_8$, C$_3$-C$_6$, or C$_5$-C$_6$), substituted (e.g., substituted with a substituent group, a size-limited substituent group, or lower substituent group) or unsubstituted heterocycloalkylene (e.g., 3 to 8 membered, 3 to 6 membered, or 5 to 6 membered), substituted (e.g., substituted with a substituent group, a size-limited substituent group, or lower substituent group) or unsubstituted arylene (e.g., $C_6$-$C_{10}$, $C_6$, or phenyl), or substituted (e.g., substituted with a substituent group, a size-limited substituent group, or lower substituent group) or unsubstituted heteroarylene (e.g., 5 to 10 membered, 5 to 9 membered, or 5 to 6 membered).

In embodiments, $L^{1.4}$ is independently a bond, —O—, —S—, —NH—, —C(O)NH—, —C(O)—, —S(O)$_{n10}$NH—, substituted (e.g., substituted with a substituent group, a size-limited substituent group, or lower substituent group) or unsubstituted alkylene (e.g., $C_1$-$C_8$, $C_1$-$C_6$, or $C_1$-$C_4$), substituted (e.g., substituted with a substituent group, a size-limited substituent group, or lower substituent group) or unsubstituted heteroalkylene (e.g., 2 to 8 membered, 2 to 6 membered, or 2 to 4 membered), substituted (e.g., substituted with a substituent group, a size-limited substituent group, or lower substituent group) or unsubstituted cycloalkylene (e.g., $C_3$-$C_8$, $C_3$-$C_6$, or $C_5$-$C_6$), substituted (e.g., substituted with a substituent group, a size-limited substituent group, or lower substituent group) or unsubstituted heterocycloalkylene (e.g., 3 to 8 membered, 3 to 6 membered, or 5 to 6 membered), substituted (e.g., substituted with a substituent group, a size-limited substituent group, or lower substituent group) or unsubstituted arylene (e.g., $C_6$-$C_{10}$, $C_6$, or phenyl), or substituted (e.g., substituted with a substituent group, a size-limited substituent group, or lower substituent group) or unsubstituted heteroarylene (e.g., 5 to 10 membered, 5 to 9 membered, or 5 to 6 membered).

In embodiments, $L^1$ is independently a bond, —O—, —S—, —NH—, —C(O)NH—, —C(O)—, —S(O)$_1$NH—, substituted with a substituent group or unsubstituted $C_1$-$C_8$ substituted alkylene, substituted with a substituent group or unsubstituted 2 to 8 membered heteroalkylene, substituted substituted with a substituent group or unsubstituted $C_3$-$C_8$ cycloalkylene, substituted with a substituent group or unsubstituted 3 to 8 membered heterocycloalkylene, substituted with a substituent group or unsubstituted $C_6$-$C_{10}$ arylene, or substituted with a substituent group or unsubstituted 5 to 10 membered heteroarylene.

In embodiments, $L^{1.4}$ is independently a bond, —O—, —S—, —NH—, —C(O)NH—, —C(O)—, —S(O)$_{n10}$NH—, substituted with a substituent group or unsubstituted $C_1$-$C_8$ substituted alkylene, substituted with a substituent group or unsubstituted 2 to 8 membered heteroalkylene, substituted substituted with a substituent group or unsubstituted $C_3$-$C_8$ cycloalkylene, substituted with a substituent group or unsubstituted 3 to 8 membered heterocycloalkylene, substituted with a substituent group or unsubstituted $C_6$-$C_{10}$ arylene, or substituted with a substituent group or unsubstituted 5 to 10 membered heteroarylene.

In embodiments, $L^1$ is independently a bond, —O—, —S—, —NH—, —C(O)NH—, —C(O)—, —S(O)$_{n1}$NH—, unsubstituted alkylene (e.g., $C_1$-$C_8$, $C_1$-$C_6$, or $C_1$-$C_4$), unsubstituted heteroalkylene (e.g., 2 to 8 membered, 2 to 6 membered, or 2 to 4 membered), unsubstituted cycloalkylene (e.g., $C_3$-$C_8$, $C_3$-$C_6$, or $C_5$-$C_6$), unsubstituted heterocycloalkylene (e.g., 3 to 8 membered, 3 to 6 membered, or 5 to 6 membered), unsubstituted arylene (e.g., $C_6$-$C_{10}$, $C_6$, or phenyl), or unsubstituted heteroarylene (e.g., 5 to 10 membered, 5 to 9 membered, or 5 to 6 membered).

In embodiments, $L^{1.4}$ is independently a bond, —O—, —S—, —NH—, —C(O)NH—, —C(O)—, —S(O)$_{n10}$NH—, unsubstituted alkylene (e.g., $C_1$-$C_8$, $C_1$-$C_6$, or $C_1$-$C_4$), unsubstituted heteroalkylene (e.g., 2 to 8 membered, 2 to 6 membered, or 2 to 4 membered), unsubstituted cycloalkylene (e.g., $C_3$-$C_8$, $C_3$-$C_6$, or $C_5$-$C_6$), unsubstituted heterocycloalkylene (e.g., 3 to 8 membered, 3 to 6 membered, or 5 to 6 membered), unsubstituted arylene (e.g., $C_6$-$C_{10}$, $C_6$, or phenyl), or unsubstituted heteroarylene (e.g., 5 to 10 membered, 5 to 9 membered, or 5 to 6 membered).

In embodiments, $L^3$ is independently a bond, —O—, —S—, —NH—, —C(O)NH—, —C(O)—, —S(O)$_{n1}$NH—, substituted (e.g., substituted with a substituent group, a size-limited substituent group, or lower substituent group) or unsubstituted alkylene (e.g., $C_1$-$C_8$, $C_1$-$C_6$, or $C_1$-$C_4$), substituted (e.g., substituted with a substituent group, a size-limited substituent group, or lower substituent group) or unsubstituted heteroalkylene (e.g., 2 to 8 membered, 2 to 6 membered, or 2 to 4 membered), substituted (e.g., substituted with a substituent group, a size-limited substituent group, or lower substituent group) or unsubstituted cycloalkylene (e.g., $C_3$-$C_8$, $C_3$-$C_6$, or $C_5$-$C_6$), substituted (e.g., substituted with a substituent group, a size-limited substituent group, or lower substituent group) or unsubstituted heterocycloalkylene (e.g., 3 to 8 membered, 3 to 6 membered, or 5 to 6 membered), substituted (e.g., substituted with a substituent group, a size-limited substituent group, or lower substituent group) or unsubstituted arylene (e.g., $C_6$-$C_{10}$, $C_6$, or phenyl), or substituted (e.g., substituted with a substituent group, a size-limited substituent group, or lower substituent group) or unsubstituted heteroarylene (e.g., 5 to 10 membered, 5 to 9 membered, or 5 to 6 membered).

In embodiments, $L^{3.4}$ is independently a bond, —O—, —S—, —NH—, —C(O)NH—, —C(O)—, —S(O)$_{n10}$NH—, substituted (e.g., substituted with a substituent group, a size-limited substituent group, or lower substituent group) or unsubstituted alkylene (e.g., $C_1$-$C_8$, $C_1$-$C_6$, or $C_1$-$C_4$), substituted (e.g., substituted with a substituent group, a size-limited substituent group, or lower substituent group) or unsubstituted heteroalkylene (e.g., 2 to 8 membered, 2 to 6 membered, or 2 to 4 membered), substituted (e.g., substituted with a substituent group, a size-limited substituent group, or lower substituent group) or unsubstituted cycloalkylene (e.g., $C_3$-$C_8$, $C_3$-$C_6$, or $C_5$-$C_6$), substituted (e.g., substituted with a substituent group, a size-limited substituent group, or lower substituent group) or unsubstituted heterocycloalkylene (e.g., 3 to 8 membered, 3 to 6 membered, or 5 to 6 membered), substituted (e.g., substituted with a substituent group, a size-limited substituent group, or lower substituent group) or unsubstituted arylene (e.g., $C_6$-$C_{10}$, $C_6$, or phenyl), or substituted (e.g., substituted with a substituent group, a size-limited substituent group, or lower substituent group) or unsubstituted heteroarylene (e.g., 5 to 10 membered, 5 to 9 membered, or 5 to 6 membered).

In embodiments, $L^3$ is independently a bond, —O—, —S—, —NH—, —C(O)NH—, —C(O)—, —S(O)$_1$NH—, substituted with a substituent group or unsubstituted $C_1$-$C_8$ substituted alkylene, substituted with a substituent group or unsubstituted 2 to 8 membered heteroalkylene, substituted substituted with a substituent group or unsubstituted $C_3$-$C_8$ cycloalkylene, substituted with a substituent group or unsubstituted 3 to 8 membered heterocycloalkylene, substituted with a substituent group or unsubstituted $C_6$-$C_{10}$ arylene, or substituted with a substituent group or unsubstituted 5 to 10 membered heteroarylene.

In embodiments, $L^{3.4}$ is independently a bond, —O—, —S—, —NH—, —C(O)NH—, —C(O)—, —S(O)$_{n10}$NH—, substituted with a substituent group or unsubstituted $C_1$-$C_8$ substituted alkylene, substituted with a substituent group or unsubstituted 2 to 8 membered heteroalkylene, substituted substituted with a substituent group or unsubstituted $C_3$-$C_8$ cycloalkylene, substituted with a substituent group or unsubstituted 3 to 8 membered heterocycloalkylene, substituted with a substituent group or unsubstituted $C_6$-$C_{10}$ arylene, or substituted with a substituent group or unsubstituted 5 to 10 membered heteroarylene.

In embodiments, $L^3$ is independently a bond, —O—, —S—, —NH—, —C(O)NH—, —C(O)—, —S(O)$_{n10}$NH—, unsubstituted alkylene (e.g., $C_1$-$C_8$, $C_1$-$C_6$, or $C_1$-$C_4$), unsubstituted heteroalkylene (e.g., 2 to 8 membered, 2 to 6 membered, or 2 to 4 membered), unsubstituted cycloalkylene (e.g., $C_3$-$C_8$, $C_3$-$C_6$, or $C_5$-$C_6$), unsubstituted heterocycloalkylene (e.g., 3 to 8 membered, 3 to 6 membered, or 5 to 6 membered), unsubstituted arylene (e.g., $C_6$-$C_{10}$, $C_6$, or phenyl), or unsubstituted heteroarylene (e.g., 5 to 10 membered, 5 to 9 membered, or 5 to 6 membered).

In embodiments, $L^{3A}$ is independently a bond, —O—, —S—, —NH—, —C(O)NH—, —C(O)—, —S(O)$_{n10}$NH—, unsubstituted alkylene (e.g., $C_1$-$C_8$, $C_1$-$C_6$, or $C_1$-$C_4$), unsubstituted heteroalkylene (e.g., 2 to 8 membered, 2 to 6 membered, or 2 to 4 membered), unsubstituted cycloalkylene (e.g., $C_3$-$C_8$, $C_3$-$C_6$, or $C_5$-$C_6$), unsubstituted heterocycloalkylene (e.g., 3 to 8 membered, 3 to 6 membered, or 5 to 6 membered), unsubstituted arylene (e.g., $C_6$-$C_{10}$, $C_6$, or phenyl), or unsubstituted heteroarylene (e.g., 5 to 10 membered, 5 to 9 membered, or 5 to 6 membered).

In embodiments, $L^2$ is —C(O)O—, —C(O)—O—C(O)—, a peptide linker, —C(O)S—, —NH—NH—, —S—S—, —N=N—, —C(N(R'))—, —C(OR$^2$)(OR$^3$)—, wherein R$^1$, R$^2$, and R$^3$ are independently substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In embodiments, $L^{2A}$ is —C(O)O—, —C(O)—O—C(O)—, a peptide linker, —C(O)S—, —NH—NH—, —S—S—, —N=N—, —C(N(R$^{1A}$))—, —C(OR$^{2A}$)(OR$^{3A}$)—, wherein R$^{1A}$, R$^{2A}$, and R$^{3A}$ are independently substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In embodiments, $L^2$ is —C(O)O—, —C(O)—O—C(O)—, a peptide linker, —C(O)S—, —NH—NH—, —S—S—, —N=N—, —C(N(R$^1$))—, —C(OR$^2$)(OR$^3$)—.

In embodiments, $L^{2A}$ is —C(O)O—, —C(O)—O—C(O)—, a peptide linker, —C(O)S—, —NH—NH—, —S—S—, —N=N—, —C(N(R$^{1A}$))—, —C(OR$^{2A}$)(OR$^{3A}$)—.

In embodiments, R$^1$ is hydrogen, substituted (e.g., substituted with a substituent group, a size-limited substituent group, or lower substituent group) or unsubstituted alkyl (e.g., $C_1$-$C_8$, $C_1$-$C_6$, or $C_1$-$C_4$), substituted (e.g., substituted with a substituent group, a size-limited substituent group, or lower substituent group) or unsubstituted heteroalkyl (e.g., 2 to 8 membered, 2 to 6 membered, or 2 to 4 membered), substituted (e.g., substituted with a substituent group, a size-limited substituent group, or lower substituent group) or unsubstituted cycloalkyl (e.g., $C_3$-$C_8$, $C_3$-$C_6$, or $C_5$-$C_6$), substituted (e.g., substituted with a substituent group, a size-limited substituent group, or lower substituent group) or unsubstituted heterocycloalkyl (e.g., 3 to 8 membered, 3 to 6 membered, or 5 to 6 membered), substituted (e.g., substituted with a substituent group, a size-limited substituent group, or lower substituent group) or unsubstituted aryl (e.g., $C_6$-$C_{10}$, $C_6$, or phenyl), or substituted (e.g., substituted with a substituent group, a size-limited substituent group, or lower substituent group) or unsubstituted heteroaryl (e.g., 5 to 10 membered, 5 to 9 membered, or 5 to 6 membered).

In embodiments, R$^{1A}$ is hydrogen, substituted (e.g., substituted with a substituent group, a size-limited substituent group, or lower substituent group) or unsubstituted alkyl (e.g., $C_1$-$C_8$, $C_1$-$C_6$, or $C_1$-$C_4$), substituted (e.g., substituted with a substituent group, a size-limited substituent group, or lower substituent group) or unsubstituted heteroalkyl (e.g., 2 to 8 membered, 2 to 6 membered, or 2 to 4 membered), substituted (e.g., substituted with a substituent group, a size-limited substituent group, or lower substituent group) or unsubstituted cycloalkyl (e.g., $C_3$-$C_8$, $C_3$-$C_6$, or $C_5$-$C_6$), substituted (e.g., substituted with a substituent group, a size-limited substituent group, or lower substituent group) or unsubstituted heterocycloalkyl (e.g., 3 to 8 membered, 3 to 6 membered, or 5 to 6 membered), substituted (e.g., substituted with a substituent group, a size-limited substituent group, or lower substituent group) or unsubstituted aryl (e.g., $C_6$-$C_{10}$, $C_6$, or phenyl), or substituted (e.g., substituted with a substituent group, a size-limited substituent group, or lower substituent group) or unsubstituted heteroaryl (e.g., 5 to 10 membered, 5 to 9 membered, or 5 to 6 membered).

In embodiments, R$^1$ is substituted with a substituent group or unsubstituted $C_1$-$C_8$ substituted alkyl, substituted with a substituent group or unsubstituted 2 to 8 membered heteroalkyl, substituted substituted with a substituent group or unsubstituted $C_3$-$C_8$ cycloalkyl, substituted with a substituent group or unsubstituted 3 to 8 membered heterocycloalkyl, substituted with a substituent group or unsubstituted $C_6$-$C_{10}$ aryl, or substituted with a substituent group or unsubstituted 5 to 10 membered heteroaryl.

In embodiments, R$^{1A}$ is substituted with a substituent group or unsubstituted $C_1$-$C_8$ substituted alkyl, substituted with a substituent group or unsubstituted 2 to 8 membered heteroalkyl, substituted substituted with a substituent group or unsubstituted $C_3$-$C_8$ cycloalkyl, substituted with a substituent group or unsubstituted 3 to 8 membered heterocycloalkyl, substituted with a substituent group or unsubstituted $C_6$-$C_{10}$ aryl, or substituted with a substituent group or unsubstituted 5 to 10 membered heteroaryl.

In embodiments, R$^1$ is unsubstituted alkyl (e.g., $C_1$-$C_8$, $C_1$-$C_6$, or $C_1$-$C_4$), unsubstituted heteroalkyl (e.g., 2 to 8 membered, 2 to 6 membered, or 2 to 4 membered), unsubstituted cycloalkyl (e.g., $C_3$-$C_8$, $C_3$-$C_6$, or $C_5$-$C_6$), unsubstituted heterocycloalkyl (e.g., 3 to 8 membered, 3 to 6 membered, or 5 to 6 membered), unsubstituted aryl (e.g., $C_6$-$C_{10}$, $C_6$, or phenyl), or unsubstituted heteroaryl (e.g., 5 to 10 membered, 5 to 9 membered, or 5 to 6 membered).

In embodiments, R$^{1A}$ is unsubstituted alkyl (e.g., $C_1$-$C_8$, $C_1$-$C_6$, or $C_1$-$C_4$), unsubstituted heteroalkyl (e.g., 2 to 8 membered, 2 to 6 membered, or 2 to 4 membered), unsubstituted cycloalkyl (e.g., $C_3$-$C_8$, $C_3$-$C_6$, or $C_5$-$C_6$), unsubstituted heterocycloalkyl (e.g., 3 to 8 membered, 3 to 6 membered, or 5 to 6 membered), unsubstituted aryl (e.g., $C_6$-$C_{10}$, $C_6$, or phenyl), or unsubstituted heteroaryl (e.g., 5 to 10 membered, 5 to 9 membered, or 5 to 6 membered).

In embodiments, R$^2$ is substituted (e.g., substituted with a substituent group, a size-limited substituent group, or lower substituent group) or unsubstituted alkyl (e.g., $C_1$-$C_8$, $C_1$-$C_6$, or $C_1$-$C_4$), substituted (e.g., substituted with a substituent group, a size-limited substituent group, or lower substituent group) or unsubstituted heteroalkyl (e.g., 2 to 8 membered, 2 to 6 membered, or 2 to 4 membered), substituted (e.g., substituted with a substituent group, a size-limited substituent group, or lower substituent group) or unsubstituted cycloalkyl (e.g., $C_3$-$C_8$, $C_3$-$C_6$, or $C_5$-$C_6$), substituted (e.g., substituted with a substituent group, a size-limited substituent group, or lower substituent group) or unsubstituted heterocycloalkyl (e.g., 3 to 8 membered, 3 to 6 membered, or 5 to 6 membered), substituted (e.g., substituted with a substituent group, a size-limited substituent group, or lower substituent group) or unsubstituted aryl (e.g., $C_6$-$C_{10}$, $C_6$, or phenyl), or substituted (e.g., substituted with a substituent group, a size-limited substituent group, or lower substituent group) or unsubstituted heteroaryl (e.g., 5 to 10 membered, 5 to 9 membered, or 5 to 6 membered).

In embodiments, $R^{2A}$ is substituted (e.g., substituted with a substituent group, a size-limited substituent group, or lower substituent group) or unsubstituted alkyl (e.g., $C_1$-$C_8$, $C_1$-$C_6$, or $C_1$-$C_4$), substituted (e.g., substituted with a substituent group, a size-limited substituent group, or lower substituent group) or unsubstituted heteroalkyl (e.g., 2 to 8 membered, 2 to 6 membered, or 2 to 4 membered), substituted (e.g., substituted with a substituent group, a size-limited substituent group, or lower substituent group) or unsubstituted cycloalkyl (e.g., $C_3$-$C_8$, $C_3$-$C_6$, or $C_5$-$C_6$), substituted (e.g., substituted with a substituent group, a size-limited substituent group, or lower substituent group) or unsubstituted heterocycloalkyl (e.g., 3 to 8 membered, 3 to 6 membered, or 5 to 6 membered), substituted (e.g., substituted with a substituent group, a size-limited substituent group, or lower substituent group) or unsubstituted aryl (e.g., $C_6$-$C_{10}$, $C_6$, or phenyl), or substituted (e.g., substituted with a substituent group, a size-limited substituent group, or lower substituent group) or unsubstituted heteroaryl (e.g., 5 to 10 membered, 5 to 9 membered, or 5 to 6 membered).

In embodiments, $R^2$ is substituted with a substituent group or unsubstituted $C_1$-$C_8$ substituted alkyl, substituted with a substituent group or unsubstituted 2 to 8 membered heteroalkyl, substituted substituted with a substituent group or unsubstituted $C_3$-$C_8$ cycloalkyl, substituted with a substituent group or unsubstituted 3 to 8 membered heterocycloalkyl, substituted with a substituent group or unsubstituted $C_6$-$C_{10}$ aryl, or substituted with a substituent group or unsubstituted 5 to 10 membered heteroaryl.

In embodiments, $R^{2A}$ is substituted with a substituent group or unsubstituted $C_1$-$C_8$ substituted alkyl, substituted with a substituent group or unsubstituted 2 to 8 membered heteroalkyl, substituted substituted with a substituent group or unsubstituted $C_3$-$C_8$ cycloalkyl, substituted with a substituent group or unsubstituted 3 to 8 membered heterocycloalkyl, substituted with a substituent group or unsubstituted $C_6$-$C_{10}$ aryl, or substituted with a substituent group or unsubstituted 5 to 10 membered heteroaryl.

In embodiments, $R^2$ is unsubstituted alkyl (e.g., $C_1$-$C_8$, $C_1$-$C_6$, or $C_1$-$C_4$), unsubstituted heteroalkyl (e.g., 2 to 8 membered, 2 to 6 membered, or 2 to 4 membered), unsubstituted cycloalkyl (e.g., $C_3$-$C_8$, $C_3$-$C_6$, or $C_5$-$C_6$), unsubstituted heterocycloalkyl (e.g., 3 to 8 membered, 3 to 6 membered, or 5 to 6 membered), unsubstituted aryl (e.g., $C_6$-$C_{10}$, $C_6$, or phenyl), or unsubstituted heteroaryl (e.g., 5 to 10 membered, 5 to 9 membered, or 5 to 6 membered).

In embodiments, $R^{2A}$ is unsubstituted alkyl (e.g., $C_1$-$C_8$, $C_1$-$C_6$, or $C_1$-$C_4$), unsubstituted heteroalkyl (e.g., 2 to 8 membered, 2 to 6 membered, or 2 to 4 membered), unsubstituted cycloalkyl (e.g., $C_3$-$C_8$, $C_3$-$C_6$, or $C_5$-$C_6$), unsubstituted heterocycloalkyl (e.g., 3 to 8 membered, 3 to 6 membered, or 5 to 6 membered), unsubstituted aryl (e.g., $C_6$-$C_{10}$, $C_6$, or phenyl), or unsubstituted heteroaryl (e.g., 5 to 10 membered, 5 to 9 membered, or 5 to 6 membered).

In embodiments, $R^3$ is substituted (e.g., substituted with a substituent group, a size-limited substituent group, or lower substituent group) or unsubstituted alkyl (e.g., $C_1$-$C_8$, $C_1$-$C_6$, or $C_1$-$C_4$), substituted (e.g., substituted with a substituent group, a size-limited substituent group, or lower substituent group) or unsubstituted heteroalkyl (e.g., 2 to 8 membered, 2 to 6 membered, or 2 to 4 membered), substituted (e.g., substituted with a substituent group, a size-limited substituent group, or lower substituent group) or unsubstituted cycloalkyl (e.g., $C_3$-$C_8$, $C_3$-$C_6$, or $C_5$-$C_6$), substituted (e.g., substituted with a substituent group, a size-limited substituent group, or lower substituent group) or unsubstituted heterocycloalkyl (e.g., 3 to 8 membered, 3 to 6 membered, or 5 to 6 membered), substituted (e.g., substituted with a substituent group, a size-limited substituent group, or lower substituent group) or unsubstituted aryl (e.g., $C_6$-$C_{10}$, $C_6$, or phenyl), or substituted (e.g., substituted with a substituent group, a size-limited substituent group, or lower substituent group) or unsubstituted heteroaryl (e.g., 5 to 10 membered, 5 to 9 membered, or 5 to 6 membered).

In embodiments, $R^{3A}$ is substituted (e.g., substituted with a substituent group, a size-limited substituent group, or lower substituent group) or unsubstituted alkyl (e.g., $C_1$-$C_8$, $C_1$-$C_6$, or $C_1$-$C_4$), substituted (e.g., substituted with a substituent group, a size-limited substituent group, or lower substituent group) or unsubstituted heteroalkyl (e.g., 2 to 8 membered, 2 to 6 membered, or 2 to 4 membered), substituted (e.g., substituted with a substituent group, a size-limited substituent group, or lower substituent group) or unsubstituted cycloalkyl (e.g., $C_3$-$C_8$, $C_3$-$C_6$, or $C_5$-$C_6$), substituted (e.g., substituted with a substituent group, a size-limited substituent group, or lower substituent group) or unsubstituted heterocycloalkyl (e.g., 3 to 8 membered, 3 to 6 membered, or 5 to 6 membered), substituted (e.g., substituted with a substituent group, a size-limited substituent group, or lower substituent group) or unsubstituted aryl (e.g., $C_6$-$C_{10}$, $C_6$, or phenyl), or substituted (e.g., substituted with a substituent group, a size-limited substituent group, or lower substituent group) or unsubstituted heteroaryl (e.g., 5 to 10 membered, 5 to 9 membered, or 5 to 6 membered).

In embodiments, $R^3$ is substituted with a substituent group or unsubstituted $C_1$-$C_8$ substituted alkyl, substituted with a substituent group or unsubstituted 2 to 8 membered heteroalkyl, substituted substituted with a substituent group or unsubstituted $C_3$-$C_8$ cycloalkyl, substituted with a substituent group or unsubstituted 3 to 8 membered heterocycloalkyl, substituted with a substituent group or unsubstituted $C_6$-$C_{10}$ aryl, or substituted with a substituent group or unsubstituted 5 to 10 membered heteroaryl.

In embodiments, $R^{3A}$ is substituted with a substituent group or unsubstituted $C_1$-$C_8$ substituted alkyl, substituted with a substituent group or unsubstituted 2 to 8 membered heteroalkyl, substituted substituted with a substituent group or unsubstituted $C_3$-$C_8$ cycloalkyl, substituted with a substituent group or unsubstituted 3 to 8 membered heterocycloalkyl, substituted with a substituent group or unsubstituted $C_6$-$C_{10}$ aryl, or substituted with a substituent group or unsubstituted 5 to 10 membered heteroaryl.

In embodiments, $R^3$ is unsubstituted alkyl (e.g., $C_1$-$C_8$, $C_1$-$C_6$, or $C_1$-$C_4$), unsubstituted heteroalkyl (e.g., 2 to 8 membered, 2 to 6 membered, or 2 to 4 membered), unsubstituted cycloalkyl (e.g., $C_3$-$C_8$, $C_3$-$C_6$, or $C_5$-$C_6$), unsubstituted heterocycloalkyl (e.g., 3 to 8 membered, 3 to 6 membered, or 5 to 6 membered), unsubstituted aryl (e.g., $C_6$-$C_{10}$, $C_6$, or phenyl), or unsubstituted heteroaryl (e.g., 5 to 10 membered, 5 to 9 membered, or 5 to 6 membered).

In embodiments, $R^{3A}$ is unsubstituted alkyl (e.g., $C_1$-$C_8$, $C_1$-$C_6$, or $C_1$-$C_4$), unsubstituted heteroalkyl (e.g., 2 to 8 membered, 2 to 6 membered, or 2 to 4 membered), unsubstituted cycloalkyl (e.g., $C_3$-$C_8$, $C_3$-$C_6$, or $C_5$-$C_6$), unsubstituted heterocycloalkyl (e.g., 3 to 8 membered, 3 to 6 membered, or 5 to 6 membered), unsubstituted aryl (e.g., $C_6$-$C_{10}$, $C_6$, or phenyl), or unsubstituted heteroaryl (e.g., 5 to 10 membered, 5 to 9 membered, or 5 to 6 membered).

In embodiments, the conjugate has the formula: $(X\text{-}L^3\text{-}L^2\text{-}L^1)_{n2}\text{-}A\text{-}(L^1\text{-}L^2\text{-}L^3\text{-}X)_{n3}$, wherein: X is a DPCA group; n2 and n3 are independently integers from 1 to 10; A is said biomacromolecule, and $L^1$, $L^2$, and $L^3$ are as described above, including embodiments. In embodiments, n2 and n3 are independently integers from 1 to 3. In embodiments, A is: —NH—C(O)—CH$_2$—O—(CH$_2$—CH$_2$—O)$_n$—CH$_2$—C(O)—NH—. In embodiments, n is an integer from 100 to 300. In embodiments, n is an integer from 150 to 250. In embodiments, n is an integer from 150-200. In embodiments, n is about 180.

In embodiments, the conjugate has the formula: $(X\text{-}L^3\text{-}L^2\text{-}L^1)_{n2}\text{-}A$, wherein: X is a DPCA group; n2 is an integer from 1 to 10; A is said biomacromolecule, and $L^1$, $L^2$, and $L^3$ are as described above, including embodiments. In embodiments, n2 is an integer from 1 to 3. In embodiments, A is: CH$_3$—O—(CH$_2$—CH$_2$—O)$_n$—CH$_2$—C(O)—NH—. In embodiments, n is an integer from 1 to 100. In embodiments, n is an integer from 1 to 50. In embodiments, n is an integer from 10-20. In embodiments, n is about 16.

In embodiments, the conjugate has the formula: $(X\text{-}L^3\text{-}L^2)_{n2}\text{-}L^1\text{-}A$, wherein: X is a DPCA group; n2 is an integer from 1 to 10; A is said biomacromolecule, and $L^1$, $L^2$, and $L^3$ are as described above, including embodiments. In embodiments, n2 is an integer from 1 to 3. In embodiments, A is: CH$_3$—O—(CH$_2$—CH$_2$—O)$_n$—. In embodiments, $L^1$ is substituted or unsubstituted heteroalkyl (e.g. —CH$_2$—C(O)—NH—, wherein the carbon of the CH$_2$ group is attached to the PEG oxygen when A is CH$_3$—O—(CH$_2$—CH$_2$—O)$_n$—). In embodiments, n is an integer from 1 to 100. In embodiments, n is an integer from 1 to 50. In embodiments, n is an integer from 10-20. In embodiments, n is about 16.

In embodiments, the conjugate has the formula: $(X\text{-}L^{3A}\text{-}L^{2A}\text{-}L^{1A})_{n2}\text{-}A\text{-}(L^1\text{-}L^2\text{-}L^3\text{-}X)_{n3}$, wherein: X is a DPCA group; n2 and n3 are independently integers from 1 to 10; A is said biomacromolecule, and $L^{1A}$, $L^{2A}$, $L^{3A}$, $L^1$, $L^2$, and $L^3$ are as described above, including embodiments. In embodiments, n2 and n3 are independently integers from 1 to 3. In embodiments, A is: —NH—C(O)—CH$_2$—O—(CH$_2$—CH$_2$—O)$_n$—CH$_2$—C(O)—NH—. In embodiments, n is an integer from 100 to 300. In embodiments, n is an integer from 150 to 250. In embodiments, n is an integer from 150-200. In embodiments, n is about 180.

In embodiments, the conjugate has the formula: $(X\text{-}L^{3A}\text{-}L^{2A})_2\text{-}L^{1A}\text{-}A\text{-}L^1\text{-}(L^2\text{-}L^3\text{-}X)_{n3}$, wherein: X is a DPCA group; n2 and n3 are independently integers from 1 to 10; A is said biomacromolecule, and $L^{1A}$, $L^{2A}$, $L^{3A}$, $L^1$, $L^2$, and $L^3$ are as described above, including embodiments. In embodiments, n2 and n3 are independently integers from 1 to 3. In embodiments, A is —(CH$_2$—CH$_2$—O)$_n$—. In embodiments, $L^{1A}$ is substituted or unsubstituted heteroalkyl (e.g. —NH—C(O)—CH$_2$—O— wherein the ether oxygen is attached to the PEG carbon when A is —(CH$_2$—CH$_2$—O)$_n$—). In embodiments, $L^1$ is substituted or unsubstituted heteroalkyl (e.g. —CH$_2$—C(O)—NH— wherein the carbon of the CH$_2$ group is attached to the PEG oxygen when A is —(CH$_2$—CH$_2$—O)$_n$—). In embodiments, n is an integer from 100 to 300. In embodiments, n is an integer from 150 to 250. In embodiments, n is an integer from 150-200. In embodiments, n is about 180.

Self-Assembled Nanofibers of PEG-DPCA Conjugates

Examples of chemical structures of 1,4-dihydrophenonthrolin-4-one-3-carboxylic acid (DPCA) and exemplary PEG-DPCA conjugates (such as P3D1, P7D1, P7D3, and P80D6) discussed herein are shown in FIG. 1. Initial studies of PEG-DPCA conjugates having a single terminal DPCA group (P7D1 and P3D1) did not produce evidence of self-assembly in aqueous solutions (data not shown). Therefore, PEG-DPCA conjugates comprising multiple terminal DPCA groups were synthesized. P7D3 is an example of a PEG-DPCA conjugate comprising multiple DPCA groups at one terminal end of a PEG compound and P80D6 is an example of a PEG-DPCA conjugate comprising multiple DPCA groups at each terminal end of a PEG compound.

Figure 10A:
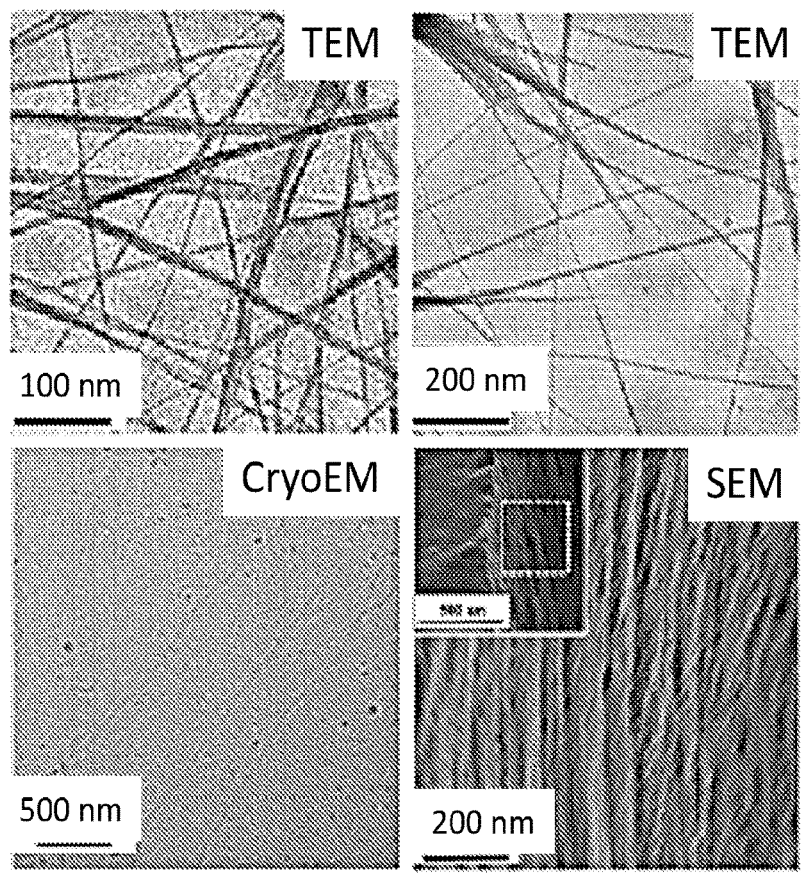
FIGS. 10A and 10B: P7D3 forms nanofiber assemblies.

TEM, cryo-TEM, and SEM images of aqueous dispersions of P7D3 revealed the presence of nanofiber structures with an average fiber diameter of 5-8 nm and length of over 1 μm (FIG. 10A). Bundles of nanofibers were observed at higher concentrations (>3 mg/mL) and also in lyophilized powder samples of P7D3 as shown in SEM images. Small-angle X-ray scattering (SAXS) analysis of P7D3 revealed a −1 slope in the low q range of the 1-D scattering curve, confirming the presence of long cylinders (black curve in FIG. 10B). The diameter of the cylinders was calculated to be 4.0 nm using a modified Guinier analysis (FIG. 5), consistent with an order size of 4-6 nm for lyophilized P7D3 (curve in FIG. 10B) and 5-8 nm obtained from the TEM images. The P7D3 nanofibers likely contain a hydrophilic PEG corona and a hydrophobic core of DPCA, an arrangement that is consistent with the combined dimensions of the PEG chain (radius of the polymer in the mushroom regime $R_f$ about 1.85 nm) and the DPCA group (about 1.1 nm). The continuous shear viscosity of aqueous P7D3 increased steeply at concentrations above 0.1 mg/mL (FIG. 4), which was suggestive of entanglements formed by long nanofibers. Under oscillating shear, the storage modulus (G') of the nanofiber suspension was found to be low ($10^2$ Pa at 100 mg/mL) and only slightly higher than the loss modulus (G"), indicating liquid-like behavior. P80D6 exhibits gel stabilization by noncovalent bridging between nanofibers.

PEG-DPCA Hydrogels

Aqueous mixtures of P80D6 and P7D3 over a wide compositional range (17 different compositions at 100 mg/mL overall polymer concentration) were prepared by heating to 50° C. and cooling to room temperature. Qualitative visual observation indicated that gelation occurred within seconds upon cooling to room temperature for all compositions containing 35 mol % (7.8 wt. %) or more of P7D3. Table 1 sets forth the different mixtures of P7D3 and P80D6 and their characteristics:

TABLE 1

DPCA content and sol-gel behavior of P7D3 and P80D6 mixtures as a function of composition

| Mixture # | P7D3 Mole % | P7D3 mg/ml | P80D6 Mole % | P80D6 mg/ml | Wt % DPCA | mg DPCA/ 25 μL | Liq. or Gel @ 37° C. | $T_{sol\text{-}gel}$ (° C.) |
|---|---|---|---|---|---|---|---|---|
| 1  | 100  | 100  | 0    | 0    | 49.0 | 1.225 | L/G | 33.5 |
| 2  | 97.5 | 88.4 | 2.5  | 11.6 | 45.0 | 1.125 | L/G | 34.5 |
| 3  | 95   | 75.6 | 5    | 24.4 | 40.8 | 1.02  | G   | 42   |
| 4  | 92.5 | 66.0 | 7.5  | 34.0 | 37.4 | 0.935 | G   | 44   |
| 5  | 90   | 58.6 | 10   | 41.4 | 34.9 | 0.873 | G   | 41.5 |
| 6  | 85   | 47.6 | 15   | 52.4 | 31.2 | 0.78  | G   | 41   |
| 7  | 80   | 38.5 | 20   | 61.5 | 28.1 | 0.703 | G   | 41   |
| 8  | 75   | 32.2 | 25   | 67.8 | 25.9 | 0.648 | G   | 45   |
| 9  | 62   | 20   | 38   | 80   | 21.8 | 0.545 | G   | 50   |
| 10 | 53   | 15.0 | 47   | 85.0 | 20.1 | 0.503 | G   | 47.8 |
| 11 | 45   | 11.4 | 55   | 88.6 | 18.9 | 0.473 | G   | 46.5 |
| 12 | 41   | 10   | 59   | 90   | 18.4 | 0.460 | G   | 46.5 |
| 13 | 35   | 7.8  | 65   | 92.2 | 17.6 | 0.440 | G   | 46.5 |
| 14 | 25   | 5.0  | 75   | 95.0 | 16.7 | 0.418 | L   | *    |
| 15 | 15   | 2.8  | 85   | 97.2 | 16.0 | 0.400 | L   | *    |
| 16 | 5    | 0.8  | 95   | 99.2 | 15.3 | 0.383 | L   | *    |
| 17 | 0    | 0    | 100  | 100  | 15.0 | 0.375 | L   | *    |

L = liquid;
G = gel;
* = no transition observed above 10° C.
As used herein, a gel formed from a given mixture above is referred to as "Gel" (or "Mixture" unless the context dictates otherwise) followed by the number of the given mixture. As an example, a gel formed from Mixture #10 may be referred to as "Mixture #10" or "Gel #10".

Detailed evaluations were performed for selected compositions using a combination of dynamic shear, frequency sweep, strain sweep, and step strain rheology (FIG. 5). For brevity, Mixtures #3 and #12 (95:5 and 41:59 mole % P7D3:P80D6, respectively) are focused on herein as representative examples of low and high P80D6 content gels. Data on other compositions is provided in FIG. 6. The frequency sweep of Mixture #3 showed characteristics of viscoelastic hydrogels, with loss modulus (G") greater than storage modulus (G') at low frequency and a cross-over point above which G'>G", indicative of more elastic-like behavior at high frequency (FIG. 5A). Mixture #12 exhibited a cross-over at substantially lower frequency than Mixture #3, signifying higher gel stability at low frequency. Strain sweep curves of Mixture #3 indicated that G' was largely strain independent except at very high strain (γ>100%), however Mixture #12 exhibited a rapid decay in G' above 10% strain and ultimately behaved as a liquid (G">G') above about 30% strain (FIG. 5B). Step-strain measurements were performed in which a high instantaneous strain (γ=200%) was applied to break the network followed by constant low strain (γ=1%) to monitor the time-dependent recovery of the hydrogel. Mixtures #3 and #12 exhibited rapid decrease in G' followed by nearly complete recovery within seconds (FIG. 5C), with no hysteresis in the recovery noted over several cycles.

Figure 5A:
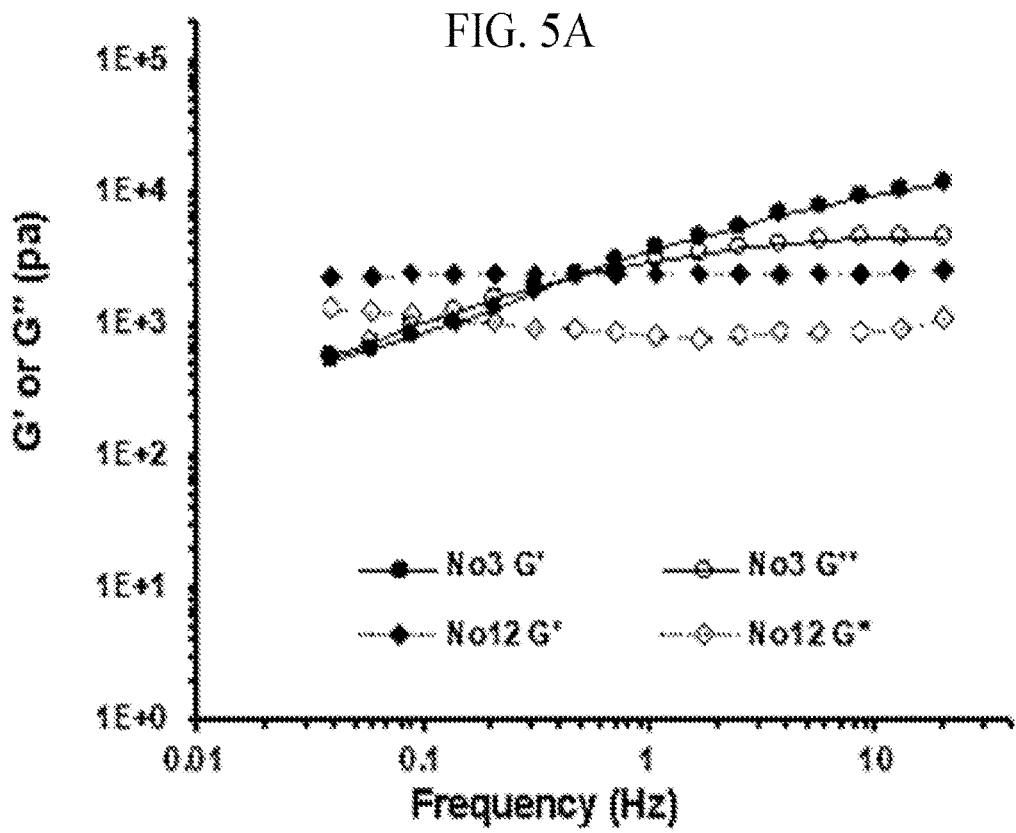
FIGS. 5A-5D: Rheological behavior of self-assembled P7D3/P80D6 mixtures #3 and #12 (see Table 1).
Figure 5B:
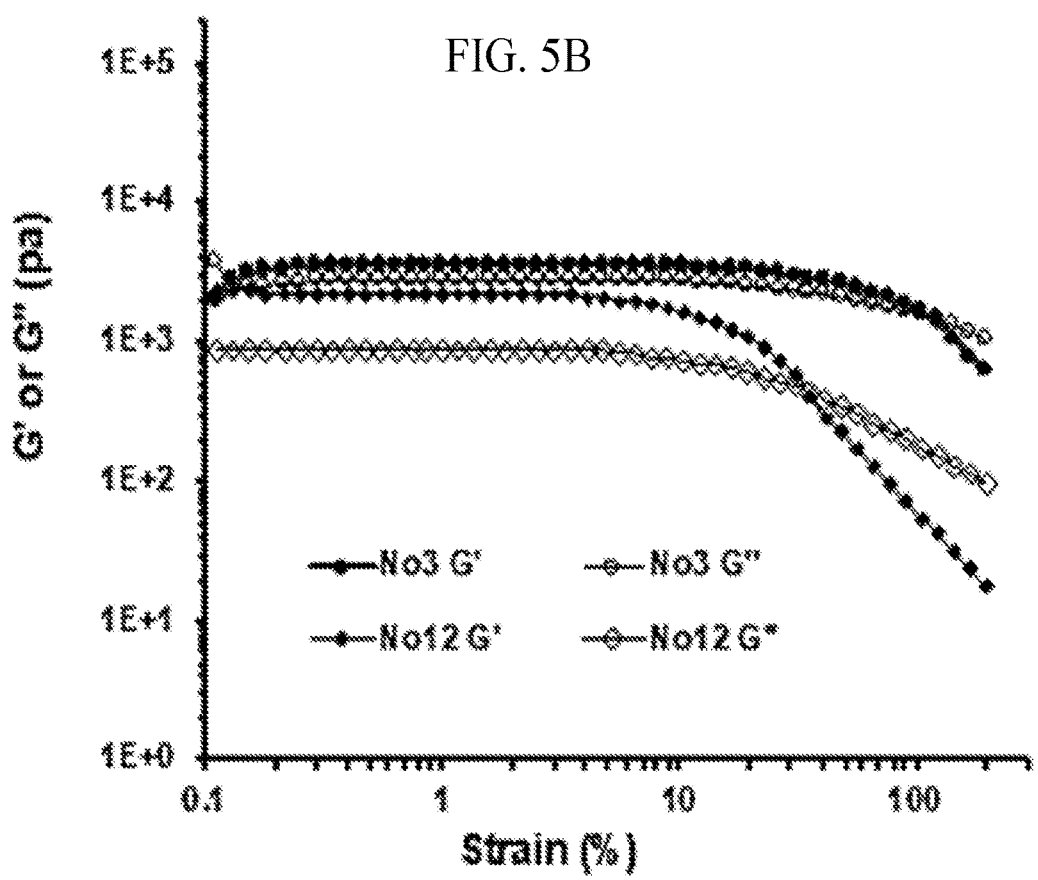
Figure 5C:
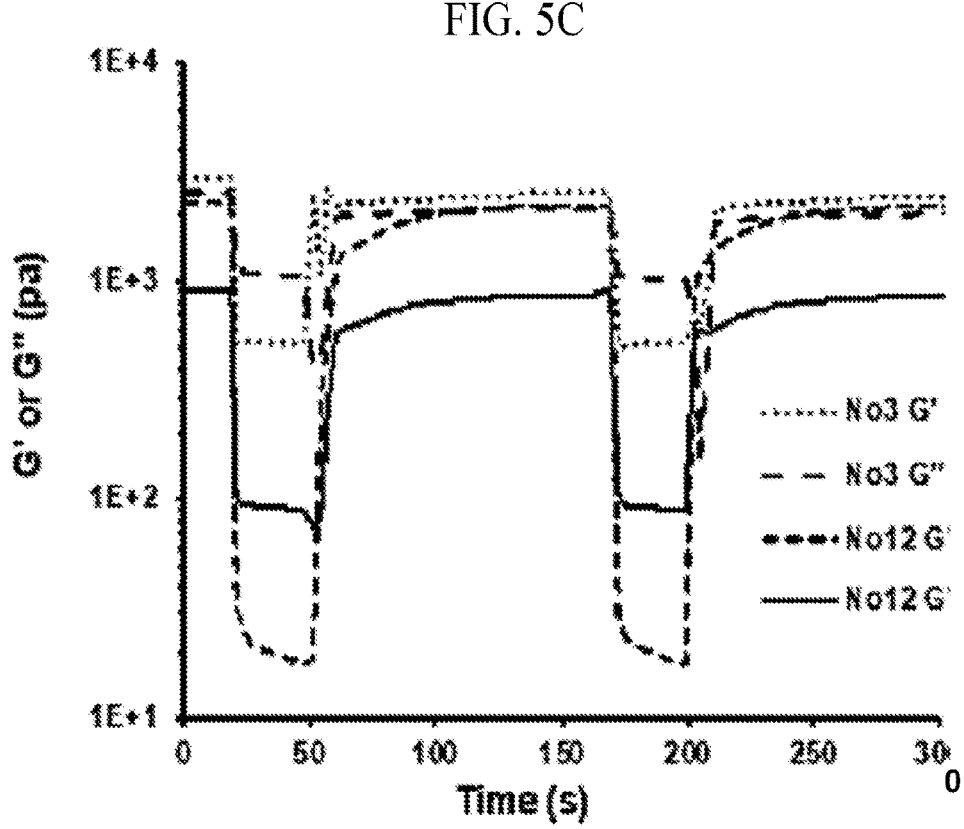
Figure 5D:
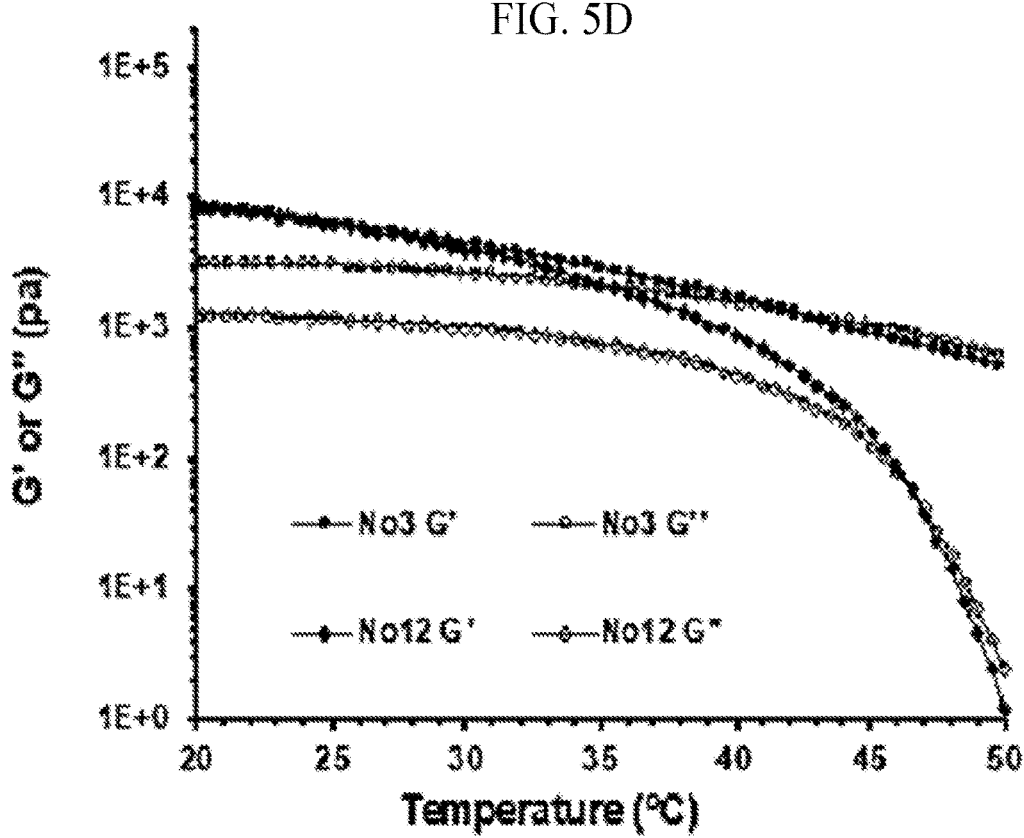

The temperature-dependent rheological behavior of Mixtures #3 and #12 are shown in FIG. 5D, and other compositions in FIG. 7. A general trend of gradual decrease in G' with increasing temperature was observed in most cases, eventually reaching a cross-over point (G'=G"). As used herein, "$T_{sol\text{-}gel}$" refers to the temperature at which a given composition reaches the cross-over point (G'=G"); the given composition behaves as a liquid above and as a gel below $T_{sol\text{-}gel}$.

Figure 12:
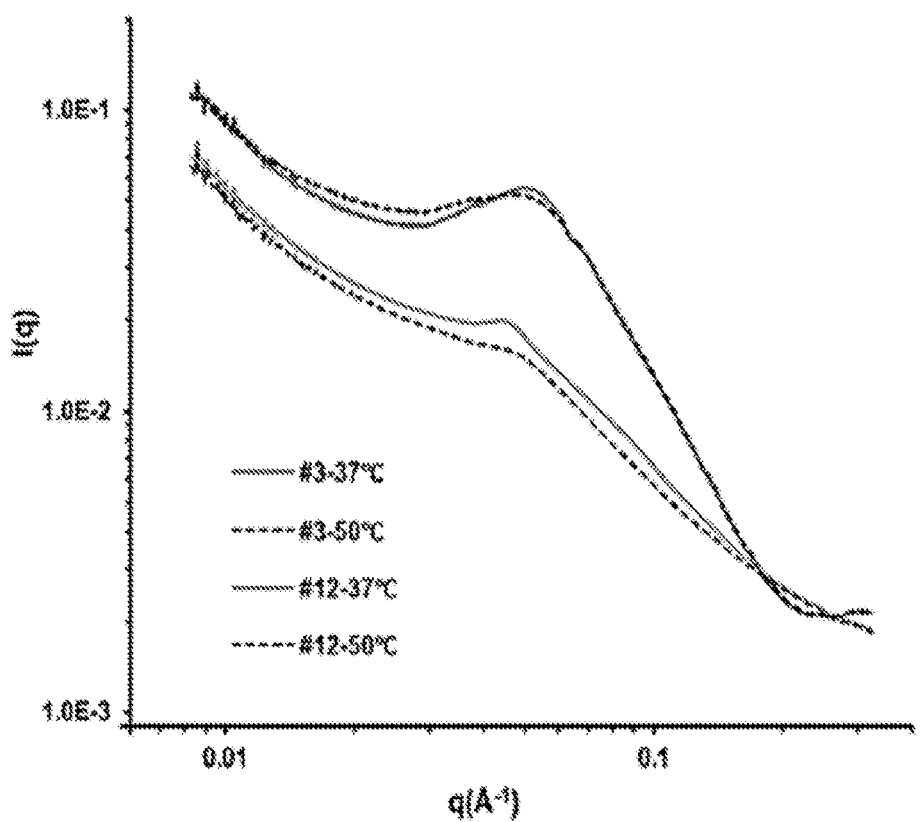
FIG. 12: SAXS analysis of P7D3/P80D6 Mixtures #3 and #12 at 370 and 50° C.

Mixtures #3 and #12 were found to have $T_{sol\text{-}gel}$ values of about 42° C. and about 46° C., respectively. Interestingly, Mixture #3 remained highly viscous above $T_{sol\text{-}gel}$ whereas Mixture #12 exhibited a more dramatic decrease in G' above the $T_{sol\text{-}gel}$ (G' decreased by 4 orders of magnitude from 20° C. to 50° C.). As this behavior was suggestive of differences in aggregation state above $T_{sol\text{-}gel}$, SAXS analysis of Mixtures #3 and #12 was performed at 37° C. and 50° C. (FIG. 12). Indeed, Mixture #12 displayed a decrease in order at 50° C. compared to 37° C. as indicated by attenuation of the peak at q values of 0.04-0.05 Å$^{-1}$ whereas order in Mixture #3 remained nearly unchanged over the same temperature range.

Figure 8A:
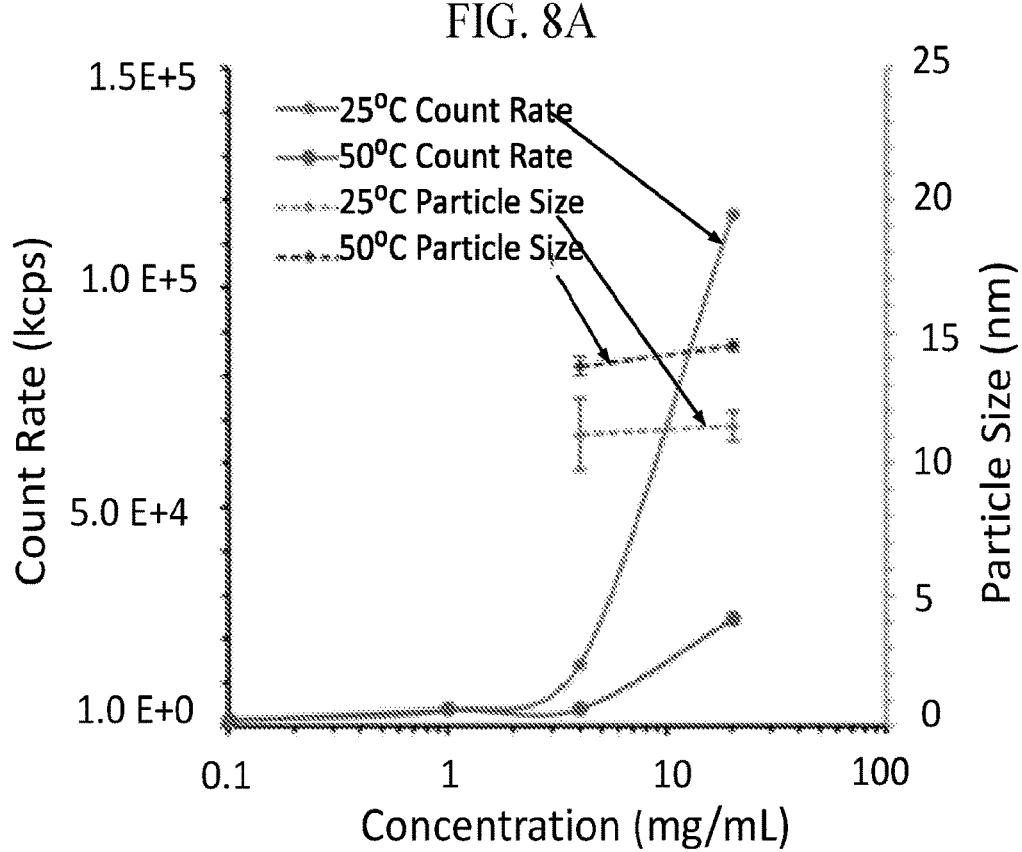
FIGS. 8A and 8B: Summary of thermorheological and self-assembly behavior of PEG-DPCA hydrogels.
Figure 8B:
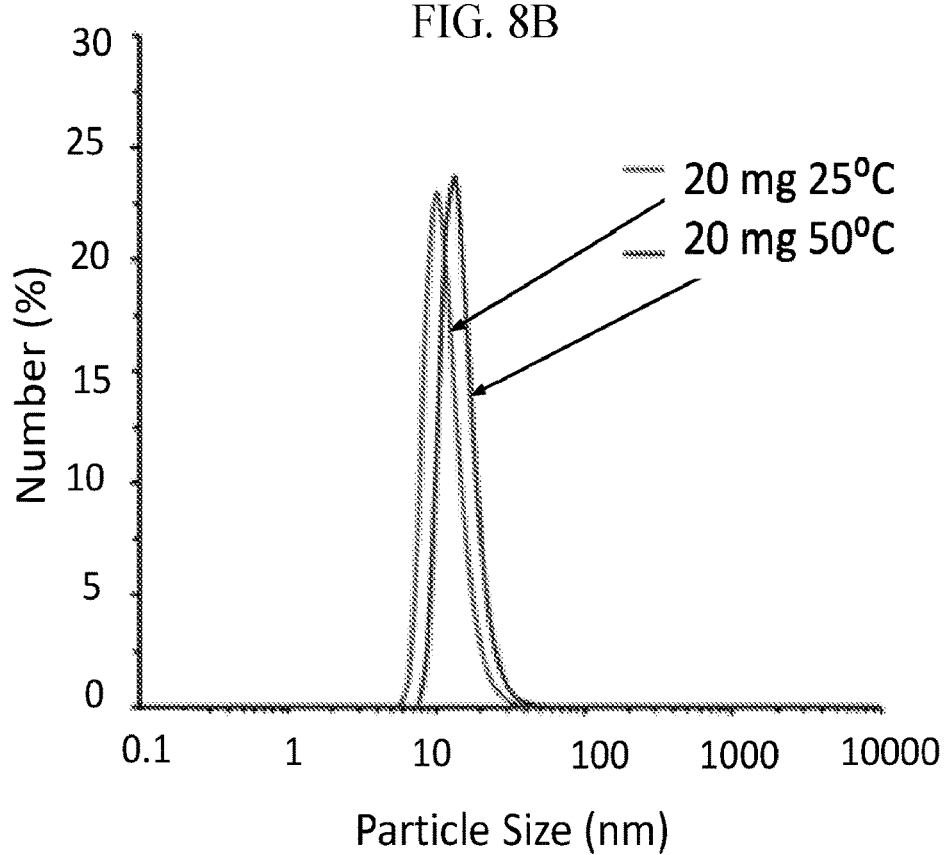
Figure 13A:
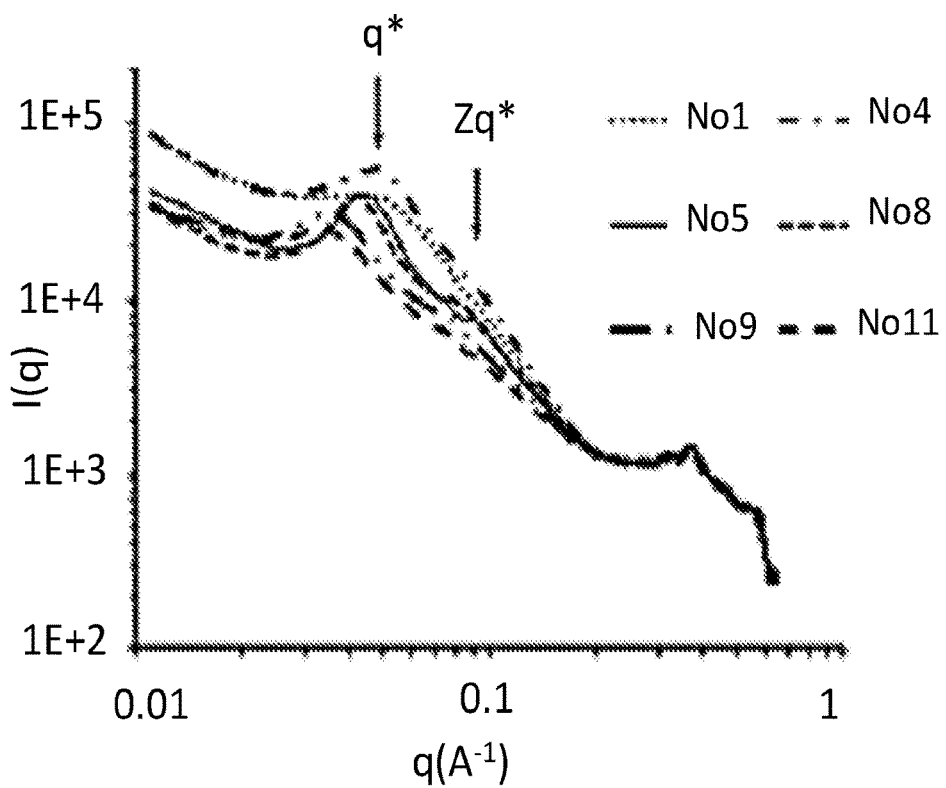
FIGS. 13A and 13B: SAXS analysis of P7D3/P80D6 Mixtures #1, #4, #5, #8, #9, and #11.
Figure 13B:
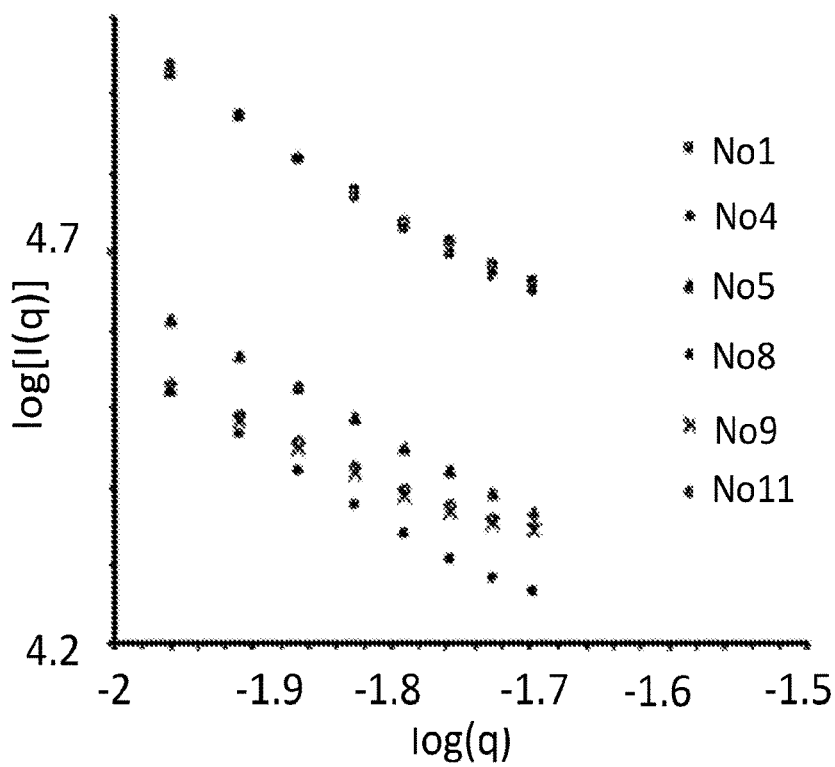

Rheological and SAXS analysis of additional compositions revealed several regimes of behavior and provided further insight into the supramolecular underpinnings of the P7D3/P80D6 compositions (FIG. 8). As indicated by the shaded region in FIG. 8, mixtures containing 5-65 mol % P80D6 were stable gels at or below 40° C. and possessed G' of at least 10$^4$ Pa, orders of magnitude greater than pure P7D3 and P80D6. At low P80D6 concentration (e.g., 2.5-25 mol %, Mixtures #2-#8, Table 1), viscoelastic gels are formed in which the basic framework consists of nanofibers of mostly P7D3 that are bridged by P80D6 (FIG. 8B). SAXS data on gels in this regime confirm the presence of cylindrical nanofiber structures as evidenced by a slope of −1 in a modified Guinier plot (FIG. 13). By virtue of its telechelic architecture, P80D6 is capable of bridging nanofibers via hydrophobic interactions between DPCA groups into the nanofiber cores, thereby stabilizing the network of nanofibers. Due to the weak nature of the hydrophobic associations among DPCA groups, shear stress or increased thermal energy can readily disrupt the network of nanofiber bridges and give rise to a gel-sol transition. Upon removal of shear, rapid re-association of hydrophobic DPCA groups of P80D6 into the nanofiber cores occurs to re-establish a gel.

Figure 4:
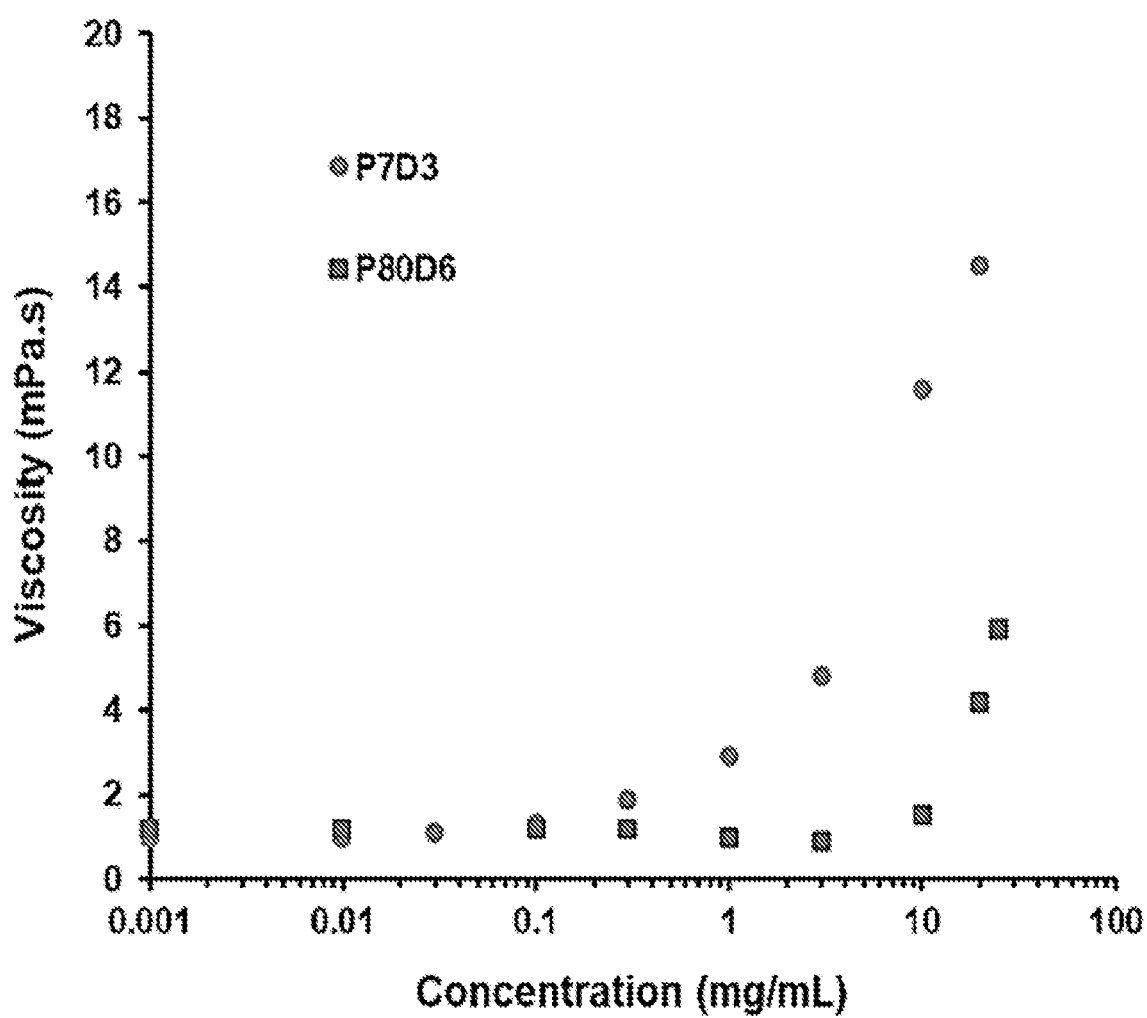
FIG. 4: Constant shear viscosity of P7D3 and P80D6 solutions at 20° C.
Figure 14:
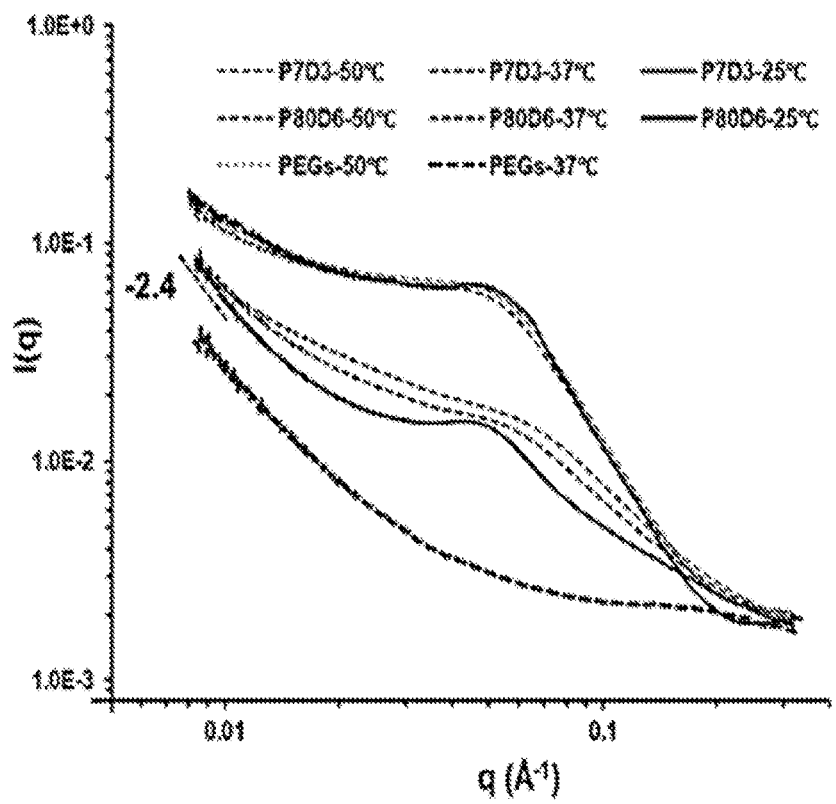
FIG. 14: SAXS scattering of P7D3, P80D6 and unmodified PEGs (PEG8000:PEG750=9:1, m/m) solution (100 mg/mL) at 25°, 370 and 50° C. The −2.4 slope in the low-q range of the P80D6 scattering curve at 25° C. indicated crosslinked nanoparticle network.

SAXS analysis suggests a change in morphology from long to shorter but wider nanowires at moderate P80D6 concentrations (Mixtures #9-#13) (FIG. 13). In this range, samples showed very low G' and G" under shear stress or when heated above $T_{sol\text{-}gel}$, which is likely attributed to disruption of nanofiber bridging and to reduced nanofiber entanglements as a likely consequence of shorter and fewer nanofibers. Above 75 mol % P80D6 (Mixtures #14-#17), mixtures did not exhibit a $T_{sol-gel}$ above 10° C. (data not shown) and behaved like liquids at room temperature. The behavior in this regime is exemplified by pure P80D6, which at low concentration (>1 mg/mL, room temperature) formed micellar aggregates measuring 11 nm in diameter as determined by DLS (FIG. 9). At higher concentrations (>25 mg/mL) micelles were bridged by telechelic P80D6 molecules leading to a steep increase in viscosity (FIG. 4). SAXS data confirmed this bridged micelle structure, where the −2.4 slope at low q (FIG. 14) indicated a crosslinked nanoparticle network with order size about 12 nm which matched the nanoparticle size determined by DLS. DLS (FIG. 9) and SAXs data (FIG. 14) showed that the bridged micelle structure of P80D6 disaggregated when heated to 50° C., whereas P7D3 nanofibers were not affected by heating, suggesting that disruption of P80D6 bridges between nanofibers occurs above $T_{sol-gel}$.

Figure 15A:
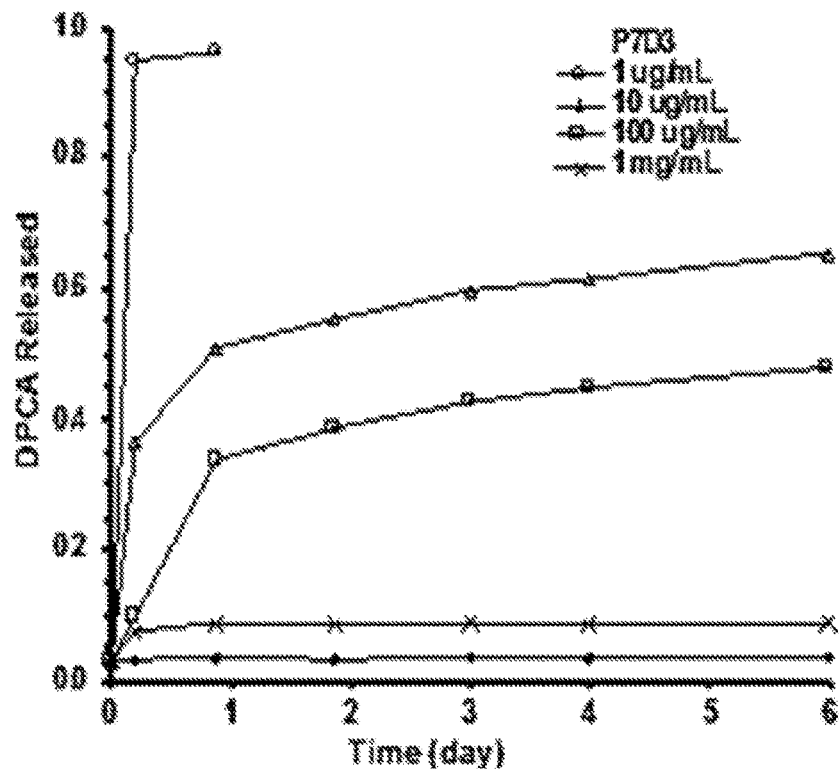
FIG. 15A-15C: In vitro DPCA release of P7D3 (FIG. 15A), P80D6 (FIG. 15B), and Gels #9, #10, and #12 (FIG. 15C) in PBS buffer at 37° C. with shaking (100 rpm).
Figure 15B:
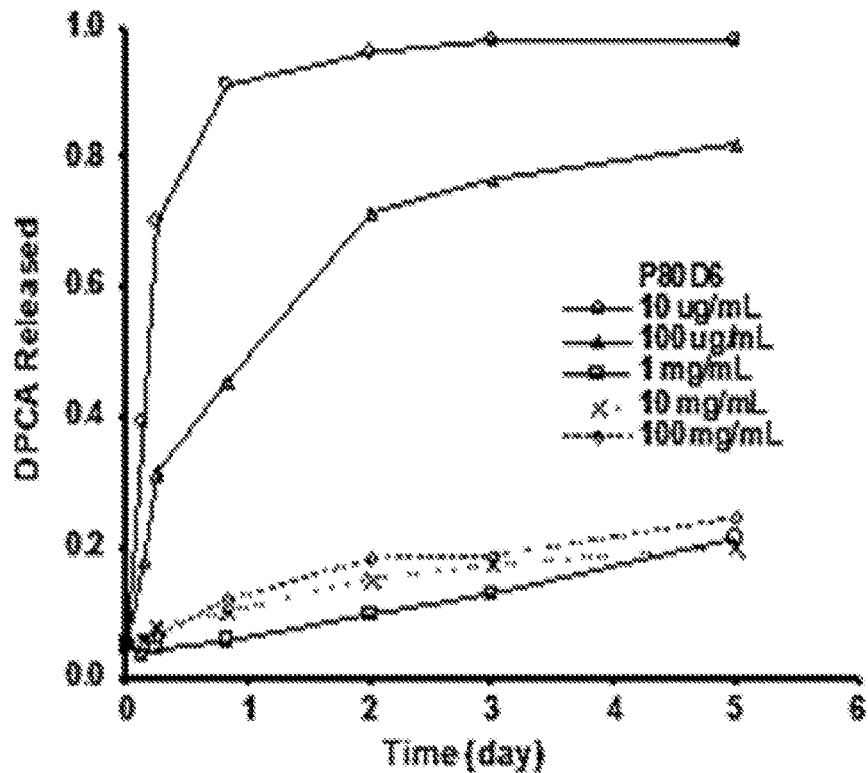
Figure 15C:
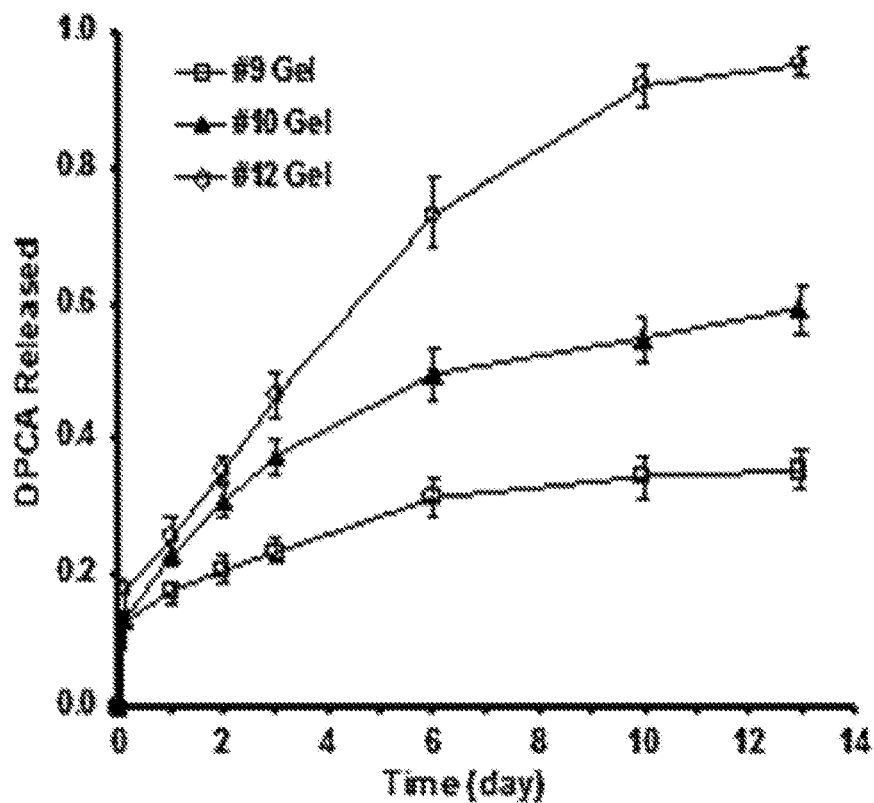

Drug Release, HIF-1α Upregulation and Progenitor Cell Marker Expression In Vitro Ester linkages between PEG compounds and DPCA groups afforded release of DPCA via hydrolysis. In vitro experiments on pure P7D3 and P80D6 showed strong concentration-dependent DPCA release behavior (FIGS. 15A and 15B). For P7D3, DPCA release was very rapid at low concentration (>95% released within 1 day @ 1 μg/mL) but was remarkably slower at high concentration (<5% release after 6 days@10 mg/mL). Similar trends were observed for pure P80D6, although at concentrations >1 mg/ml release was approximately linear through the first five days. In view of the desirable shear-thinning and self-healing properties of Gels #9, #10, and #12, in vitro drug release experiments were performed with these mixtures (FIG. 15C). An initial burst release of DPCA followed by an approximately linear release rate over a period of 12 days was observed for these gels, with DPCA release rate being generally slower in in gels with more P7D3. Gradual erosion of the hydrogel was observed, implying the disassembly of the gel by DPCA hydrolysis. Combining the results of drug release and rheological behavior, Gels #10 and #12 were identified as the best candidates for further studies.

Figure 16:
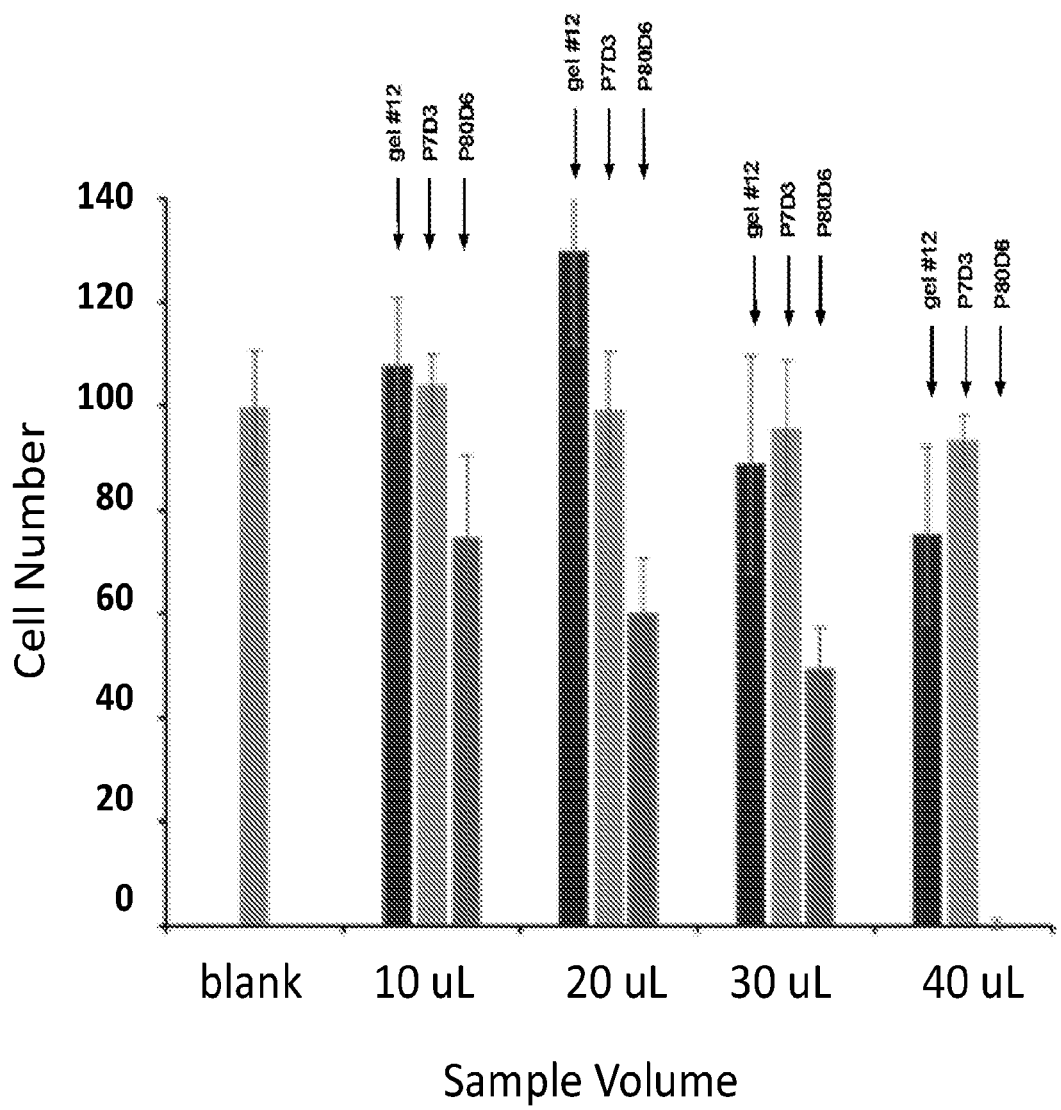
FIG. 16: Cytotoxicity of Gel #12 toward B6 fibroblast cells.
Figure 17:
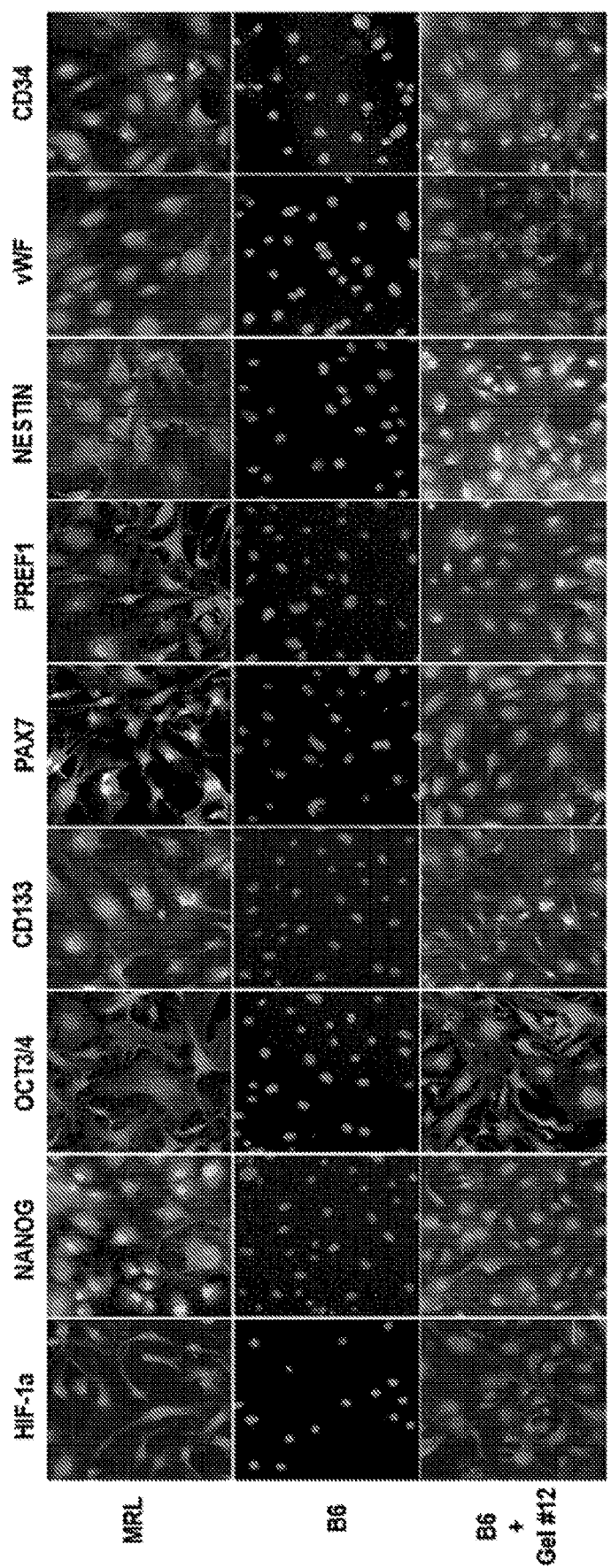
FIG. 17: Release of DPCA from PEG-DPCA hydrogel upregulates HIF-1α and induces a progenitor cell phenotype. HIF-1α stabilization and progenitor cell marker expression induced by supramolecular hydrogels. MRL mouse fibroblasts (top row), B6 mouse fibroblasts (middle row), and B6 mouse fibroblasts cultured with extract from Gel #12 (bottom row) were grown for 24 hours in 96-well plates and immunostained with antibodies against HIF-1α, NANOG, OCT3/4, CD133, PAX7, PREF1, Nestin, von Willebrand factor (vWF), and CD34.

Cells isolated from regeneration-competent adult Murphy Roths Large (MRL) mice are known to have higher expression levels of HIF-1α as well as a range of stem cell markers, compared to cells from non-healing B6 mice. Following a favorable in vitro cytotoxicity study of Gel #12 (FIG. 16), whether an MRL-like phenotype could be induced in normal cells by exposure to a PEG-DPCA hydrogel was investigated. Ear-derived primary fibroblasts harvested from adult MRL and B6 mice were cultured in conditioned media that had been exposed to Gel #12 and then evaluated for cell marker expression (FIG. 17). MRL fibroblasts (FIG. 17, top row) stained positive for HIF-1α expression and a suite of progenitor cell markers, whereas untreated B6 fibroblasts (FIG. 17, middle row) stained negative for these cell markers with the exception of slight positive staining of HIF-1α observed in dividing cells. In contrast, B6 fibroblasts treated with conditioned media for 24 hours (FIG. 17, bottom row) stained positive for HIF-1α expression as well as a number of progenitor cell markers, displaying similar patterns of cytoplasmic and nuclear staining found in primary MRL fibroblasts. B6 fibroblasts treated with PEG in the absence of DPCA stained negative for HIF-1α (FIG. 17), thereby allowing these results to be attributed to release of DPCA from the hydrogel.

PEG-DPCA Hydrogels Induce Epimorphic Tissue Regeneration

Figure 18A:
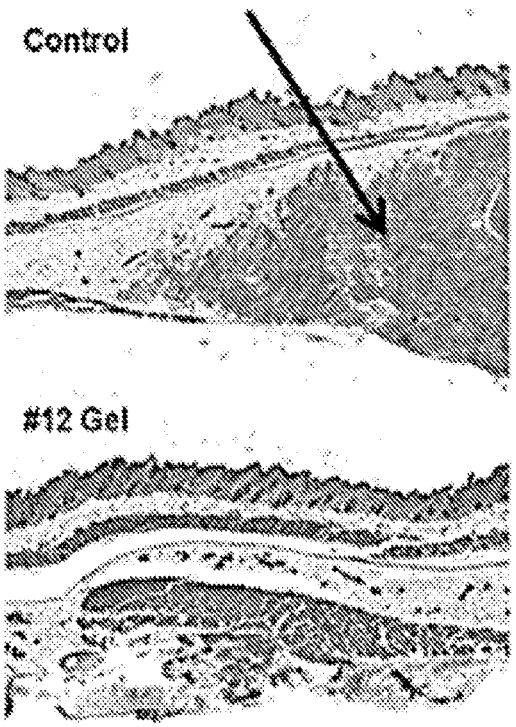
FIGS. 18A and 18B: Injection site response and earhole closure for Gel #12.
Figure 18B:
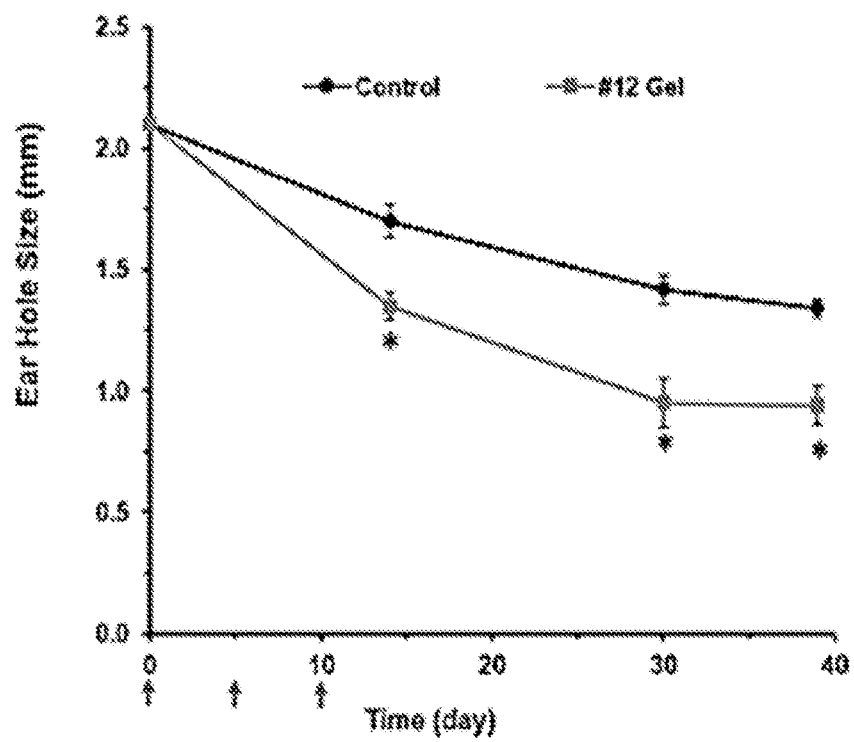
Figure 19A:
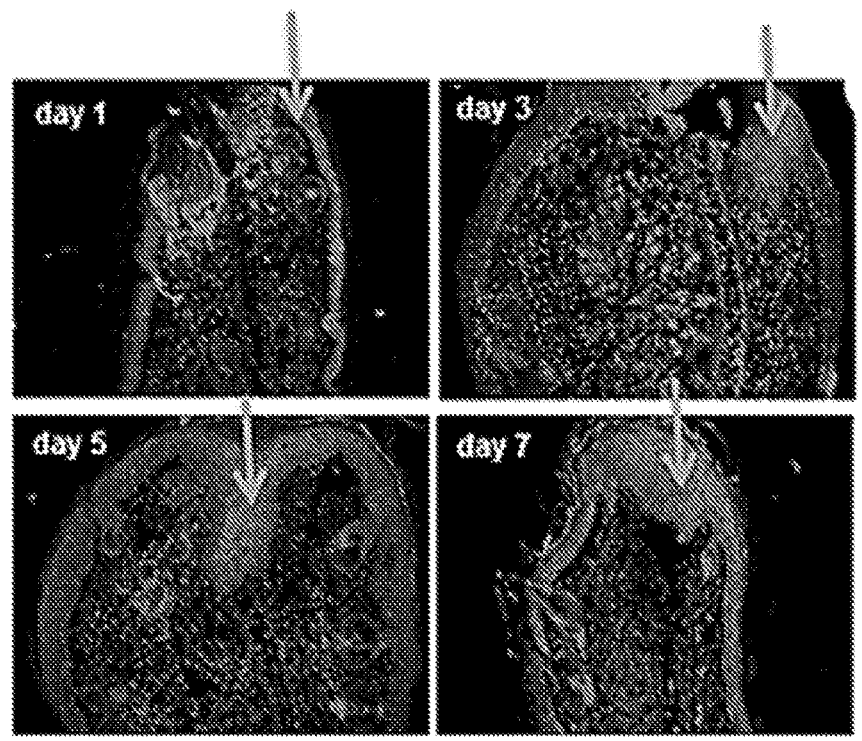
FIGS. 19A-19E: PEG-DPCA hydrogels enhance tissue regeneration in Swiss Webster mice. Swiss Webster Mice were injected subcutaneously with 25 uL of Gel #10 or PEG (control) on Day 0 and Day 8 after ear hole punching.
Figure 19B:
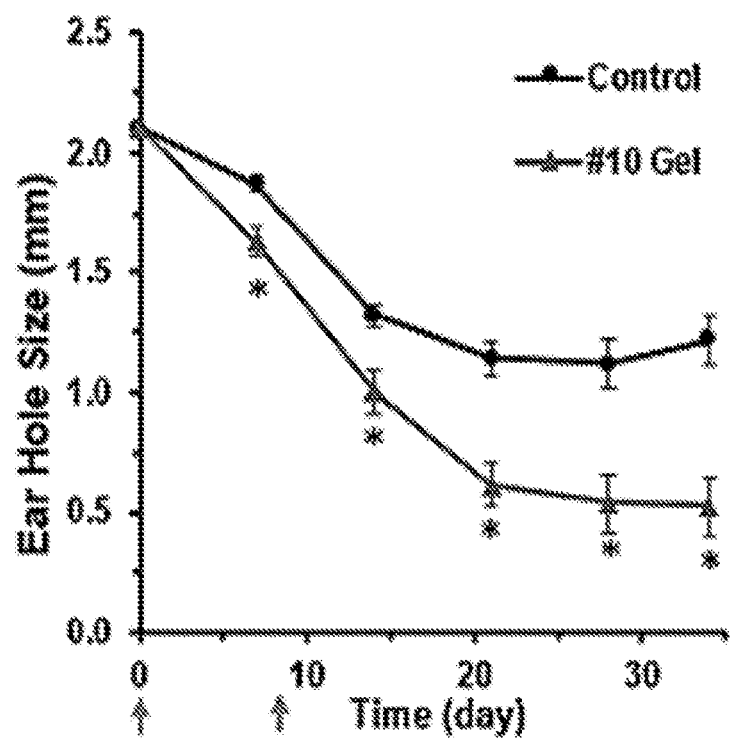
Figure 19C:
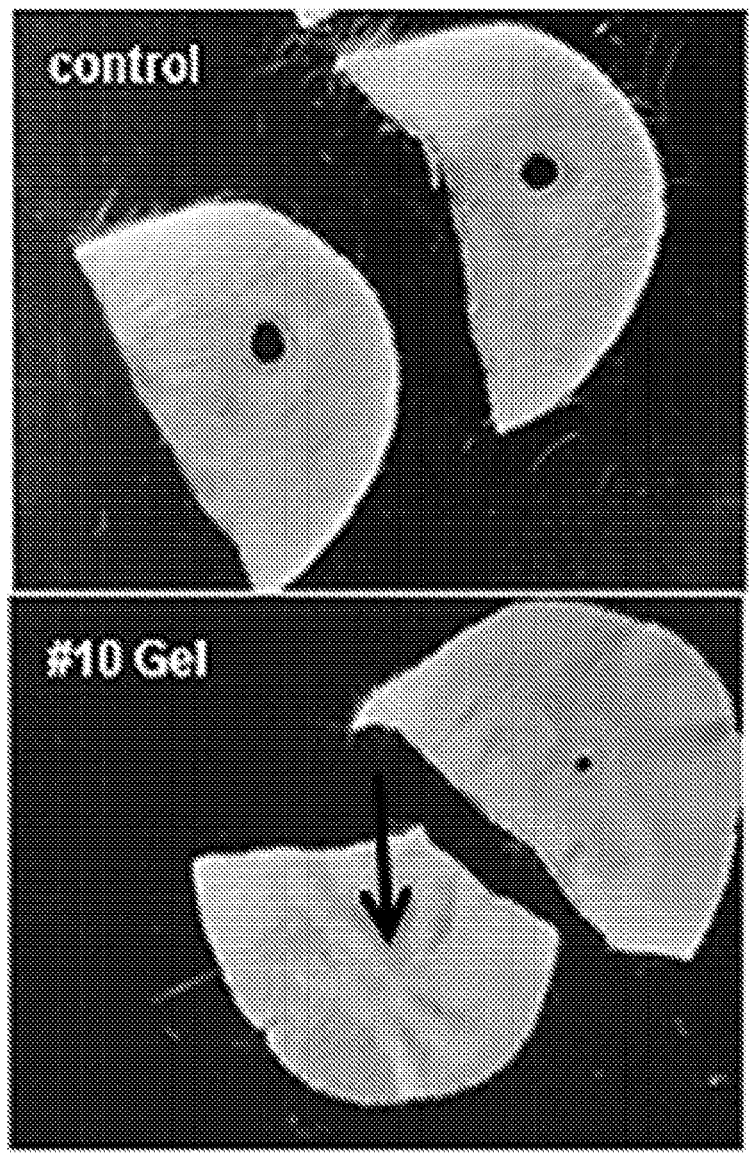
Figure 19D:
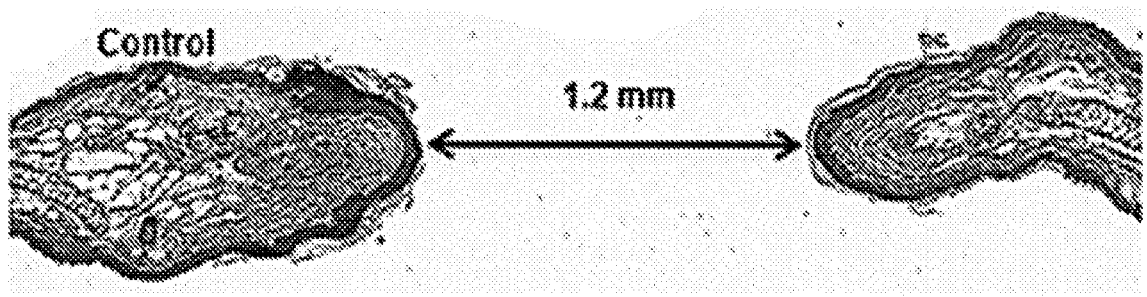
Figure 19E:
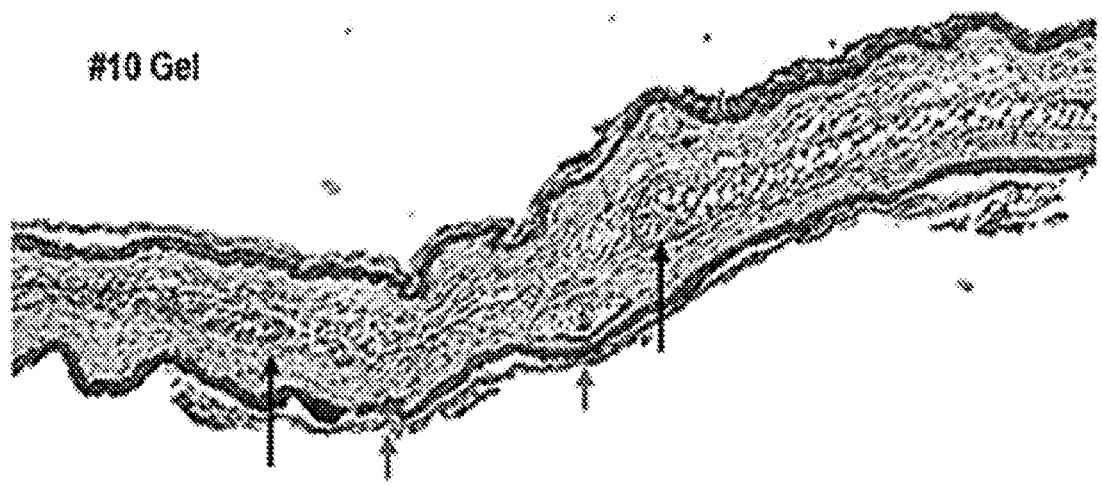

Swiss Webster (sw) mice were chosen to test the hydrogel therapy since they do not show a regenerative phenotype. An established ear hole punch model (see Clark et al. 1998) that involves punching a 2.1 mm through-thickness hole in the ear was used to ascertain tissue regeneration by physical measurements of ear hole closure combined with ear tissue harvesting and immunohistochemical analysis. 25 μL of Gels #10, #12, and a control (PEG polymers without any DPCA groups) were administered by subcutaneous injection in the upper back at Days 0 and 8. The host response at the injection site in the upper back 10 days after administration was minimal for the hydrogels, revealing intact skin and underlying muscle with no evidence of the hydrogels (FIG. 18). In contrast, a tissue hematoma was observed in the control group (treated with the control). Immunohistochemical staining of ear hole tissue revealed increased expression of HIF-1α from Days 1-7 (FIG. 19A) relative to mice without injection (data not shown). In the mice treated with Gel #10, the ear holes closed to 0.5 mm on average after 34 days (FIG. 19B), with a subset of ear holes closing completely (FIG. 19C). In contrast, earhole closure with the Gel #12 was less effective (FIG. 18). The control group showed significantly less closure, culminating in an average ear hole size of 1.2 mm which is characteristic of the typical response in non-healing mice. Alcian blue staining of tissue sections harvested at Day 34 from mice treated with control and Gel #10 showed evidence of new hair follicles and early cartilage formation (FIGS. 19D and 19E).

A separate experiment in aged C57BL/6 mice demonstrated jaw bone regeneration upon treatment with the hydrogel.

Exemplary PEG-DPCA Conjugates, Hydrogels, and Compositions

Exemplary PEG-DPCA conjugates: In some embodiments, a PEG-DPCA hydrogel has the formula $X_m$-PEG(A)-$X_p$, where X is DPCA, m and p represent the number of DPCA molecules at each end (flanking the PEG) and m plus p is equal to or greater than 1, and (A) describes the type of PEG compound. In some embodiments of the PEG-DPCA hydrogel, m is 0, 1, 2, 3, 4, 5, 6, or more than 6, and when m is 0, p is 1 or greater than 1, when m is 1, p is 2 or greater than 2 and when m is 3 or more than 3, p is 0, 1, 2, 3, 4, 5, 6, or more 6. In some embodiments of the PEG-DPCA hydrogel, when m is 0, p is 2 or greater than 2, and when m is 1, p is 1 or greater than 1.

In some embodiments, PEG-DPCA conjugates according to the present invention comprise a PEG compound and two or more DPCA groups at one terminal end or at each terminal end of the PEG compound. In some embodiments, the PEG-DPCA conjugates comprise three or more DPCA groups at one terminal end or at each terminal end of the PEG compound. In some embodiments, the PEG-DPCA conjugates comprise three DPCA groups at one terminal end or at each terminal end of the PEG compound. In some embodiments, the PEG-DPCA conjugates have Structural Formula I or Structural Formula II as follows:

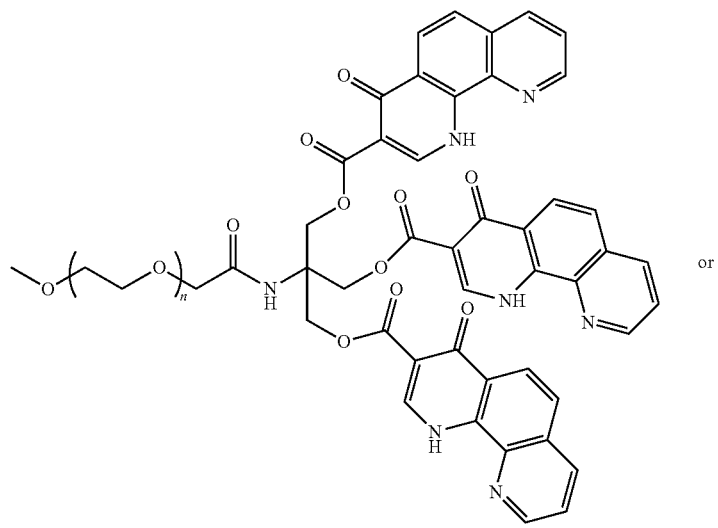
(I)

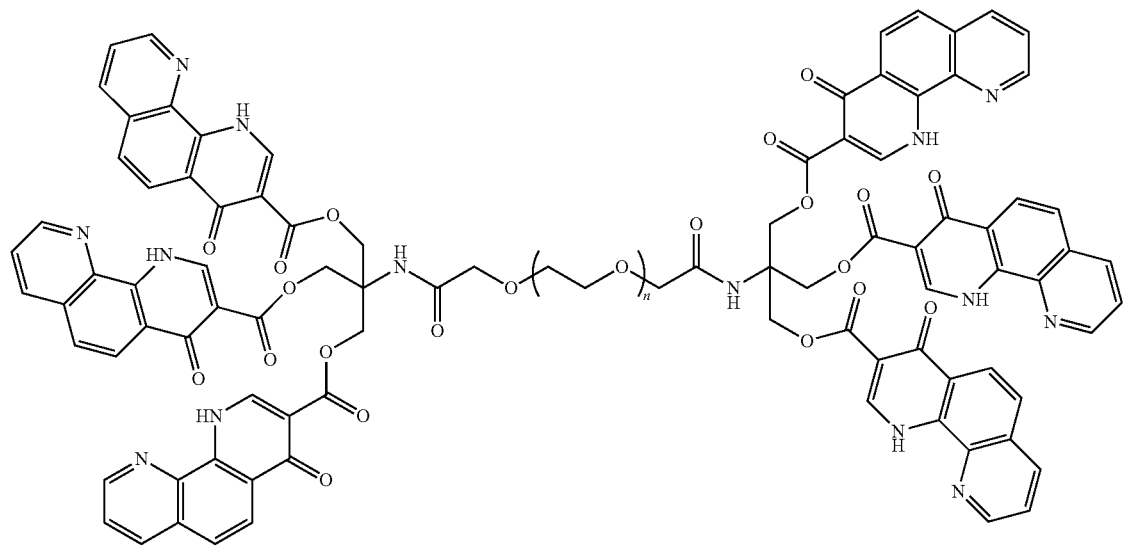
(II)

wherein n>1. In some embodiments, the PEG-DPCA conjugate is P7D3. In some embodiments, the PEG-DPCA conjugate is P80D6.

Exemplary PEG-DPCA Hydrogels. In some embodiments, PEG-DPCA hydrogels according to the present invention comprise, consists essentially of, or consist of a plurality of PEG-DPCA conjugates. As used herein, the phrase "consists essentially of" in the context of PEG-DPCA conjugates (including P7D3 and P80D6) means that the PEG-DPCA hydrogel may comprise other components, e.g., therapeutic agents, supramolecular compounds, etc., so long as the other components do not negatively impact gel formation (as compared to gel formation in the absence of the other components). In some embodiments, the PEG-DPCA hydrogels comprise, consists essentially of, or consist of at least two different PEG-DPCA conjugates. In some embodiments, the PEG-DPCA hydrogels comprise, consists essentially of, or consist of two different PEG-DPCA conjugates. In some embodiments, at least one of the PEG-DPCA conjugates comprises two or more DPCA groups at one terminal end or at each terminal end of the PEG compound. In some embodiments, at least one of the PEG-DPCA conjugates comprise three or more DPCA groups at one terminal end or at each terminal end of the PEG compound. In some embodiments, at least one of the PEG-DPCA conjugates comprise three DPCA groups at one terminal end or at each terminal end of the PEG compound. In some embodiments, at least one of the PEG-DPCA conjugates is P7D3. In some embodiments, at least one of the PEG-DPCA conjugates is P80D36. In some embodiments, a PEG-DPCA conjugate has one or more (e.g., at least one) DPCA group per PEG chain end. In some embodiments, one of the PEG-DPCA conjugates has two or more DPCA groups at one terminal end and another one of the PEG-DPCA conjugates has two or more DPCA groups at both terminal ends of the PEG compound. In some embodiments, one of the PEG-DPCA conjugates has three or more DPCA groups at one terminal end and another one of the PEG-DPCA conjugates has three or more DPCA groups at both terminal ends of the PEG compound. In some embodiments, one of the PEG-DPCA conjugates has three DPCA groups at one terminal end and another one of the PEG-DPCA conjugates has three DPCA groups at both terminal ends of the PEG compound. In some embodiments, one of the PEG-DPCA conjugates is P7D3 and another one of the PEG-DPCA conjugates is P80D6. In some embodiments, all the PEG-DPCA conjugates in a PEG-DPCA hydrogel comprise two or more DPCA groups at one terminal end of the PEG compound. In some embodiments, all the PEG-DPCA conjugates in a PEG-DPCA hydrogel comprise two or more DPCA groups at both terminal ends of the PEG compound. In some embodiments, all the PEG-DPCA conjugates in a PEG-DPCA hydrogel comprise three or more DPCA groups at one terminal end of the PEG compound. In some embodiments, all the PEG-DPCA conjugates in a PEG-DPCA hydrogel comprise three or more DPCA groups at both terminal ends of the PEG compound. In some embodiments, all the PEG-DPCA conjugates in a PEG-DPCA hydrogel comprise three DPCA groups at one terminal end of the PEG compound. In some embodiments, all the PEG-DPCA conjugates in a PEG-DPCA hydrogel comprise three DPCA groups at both terminal ends of the PEG compound. In some embodiments, all the PEG-DPCA conjugates are P7D3. In some embodiments, all the PEG-DPCA conjugates are P80D6. In some embodiments, the average molecular weights of the PEG compounds are about 250-20,000 Da, about 300-10,000 Da, and about 400-9,000 Da, about 500-8,000 Da. In some embodiments, the PEG compound is a multi-arm PEG compound, e.g., a compound having two or more PEG chains. In some embodiments, the PEG compounds are branched PEGs that have three to ten PEG chains emanating from a central core group. In some embodiments, the PEG compounds are star PEGs having 10 to 100 PEG chains emanating from a central core group. In some embodiments, PEG compounds having multiple PEG chains comprise more than one DPCA group at least one terminal end of a single PEG chain. In some embodiments, PEG compounds having multiple PEG chains comprise more than one DPCA group at the terminal ends of two or more PEG chains. The PEG chains of a PEG compound may be the same or different, e.g., the PEG chains can have different molecular weights or one PEG chain can be linear while another PEG chain branches into multiple PEG chains. In some embodiments, the average molecular weights of the PEG chains are about 250-20,000 Da, about 300-10,000 Da, and about 400-9,000 Da, about 500-8,000 Da. In some embodiments, the average molecular weights of the PEG chains are about 5,000-20,000 Da.

Exemplary Combination Hydrogels: In some embodiments, PEG-DPCA hydrogels according to the present invention comprise, consists essentially of, or consist of 2 or more different PEG-DPCA hydrogels. The particular PEG-DPCA hydrogels and amounts thereof are selected to provide a desired amount or rate of DPCA release at a given temperature and/or in a particular environment (e.g. cellular or tissue environment).

For example, in some embodiments, PEG-DPCA hydrogels according to the present invention comprise, consists essentially of, or consist of P7D3 and/or P80D6. The amounts of P7D3 and/or P80D6 in the hydrogels may be selected for the desired amount or rate of DPCA release at a given temperature. In some embodiments, the PEG-DPCA hydrogel releases DPCA at a rate wherein at least 10%, at least 15% or at least 20% is released within 1 day (24 hour period). In some embodiments, at least 20%, at least 30% or at least 40% of the DPCA is released from the hydrogel within about 3 days. In some embodiments, at least 30%, at least 40% or at least 50% of the DPCA is released from the hydrogel within about 6 days. In some embodiments, the ratio of one hydrogel to another hydrogel is selected to provide a desired amount or release rate of DPCA. For example, increasing P7D3 relative to P80D6 slows DPCA release, whereas increasing P80D6 relative to P7D3 accelerates DPCA release (see e.g. FIG. 15). In some embodiments, the PEG-DPCA hydrogels comprise a mole % of P7D3 that is at least 5%, at least 15%, at least 25%, at least 35%, at least 41%, at least 45%, at least 53%, at least 62%, at least 75%, at least 80%, at least 85%, at least 90%, at least 92.5%, at least 95%, at least 97.5%, or 100%. In some embodiments, the PEG-DPCA hydrogels comprise a mole % of P80D6 that is at least 2.5%, at least 5%, at least 7.5%, at least 10%, at least 15%, at least 20%, at least 25%, at least 38%, at least 47%, at least 55%, at least 59%, at least 65%, at least 75%, at least 85%, at least 95%, or 100%. In some embodiments, the PEG-DPCA hydrogels comprise 100 mol % of P7D3 and 0 mol % of P80D6, about 97.5 mol % of P7D3 and about 2.5 mol % of P80D6, about 95 mol % of P7D3 and about 5 mol % of P80D6, about 92.5 mol % of P7D3 and about 7.5 mol % of P80D6, about 90 mol % of P7D3 and about 10 mol % of P80D6, about 85 mol % of P7D3 and about 15 mol % of P80D6, about 80 mol % of P7D3 and about 20 mol % of P80D6, about 75 mol % of P7D3 and about 25 mol % of P80D6, about 62 mol % of P7D3 and about 38 mol % of P80D6, about 53 mol % of P7D3 and about 47 mol % of P80D6, about 45 mol % of P7D3 and about 55 mol % of P80D6, about 41 mol % of P7D3 and about 59 mol % of P80D6, about 35 mol % of P7D3 and about 65 mol % of P80D6, about 25 mol % of P7D3 and about 75 mol % of P80D6, about 15 mol % of P7D3 and about 85 mol % of P80D6, about 5 mol % of P7D3 and about 95 mol % of P80D6, or 0 mol % of P7D3 and 100 mol % of P80D6. In some embodiments, the PEG-DPCA hydrogels comprise a concentration (in mg of DPCA-hydrogel/ml buffer or other aqueous or gel-like composition) of at least about 1 mg/mL P7D3, at least about 3 mg/mL P7D3, at least about 5 mg/mL P7D3, at least about 8 mg/mL P7D3, at least about 10 mg/mL P7D3, at least about 11 mg/mL P7D3, at least about 15 mg/mL P7D3, at least about 20 mg/mL P7D3, at least about 32 mg/mL P7D3, at least about 39 mg/mL P7D3, at least about 48 mg/mL P7D3, at least about 59 mg/mL P7D3, at least about 66 mg/mL P7D3, at least about 76 mg/mL P7D3, at least about 88 mg/mL P7D3, or 100 mg/mL P7D3. In some embodiments, the PEG-DPCA hydrogels comprise at least about 12 mg/mL P80D6, at least about 24 mg/mL P80D6, at least about 34 mg/mL P80D6, at least about 41 mg/mL P80D6, at least about 52 mg/mL P80D6, at least about 62 mg/mL P80D6, at least about 68 mg/mL P80D6, at least about 80 mg/mL P80D6, at least about 85 mg/mL P80D6, at least about 89 mg/mL P80D6, at least about 90 mg/mL P80D6, at least about 92 mg/mL P80D6, at least about 95 mg/mL P80D6, at least about 97 mg/mL P80D6, at least about 99 mg/mL P80D6, or 100 mg/mL P80D6. In some embodiments, the PEG-DPCA hydrogels comprise about 100 mg/mL P7D3 and about 0 mg/mL P80D6, about 88 mg/mL P7D3 and about 12 mg/mL P80D6, about 76 mg/mL P7D3 and about 24 mg/mL P80D6, about 66 mg/mL P7D3 and about 34 mg/mL P80D6, about 59 mg/mL P7D3 and about 41 mg/mL P80D6, about 48 mg/mL P7D3 and about 52 mg/mL P80D6, about 39 mg/mL P7D3 and about 62 mg/mL P80D6, about 32 mg/mL P7D3 and about 68 mg/mL P80D6, about 20 mg/mL P7D3 and about 80 mg/mL P80D6, about 15 mg/mL P7D3 and about 85 mg/mL P80D6, about 11 mg/mL P7D3 and about 89 mg/mL P80D6, about 10 mg/mL P7D3 and about 90 mg/mL P80D6, about 8 mg/mL P7D3 and about 92 mg/mL P80D6, about 5 mg/mL P7D3 and about 95 mg/mL P80D6, about 3 mg/mL P7D3 and about 97 mg/mL P80D6, about 1 mg/mL P7D3 and about 99 mg/mL P80D6, or about 0 mg/mL P7D3 and about 100 mg/mL P80D6. In some embodiments, the PEG-DPCA hydrogels comprise at least 25 mol % or at least 5 mg/mL of P7D3. In some embodiments, the PEG-DPCA hydrogels comprise less than 75 mol % or less than 95 mg/mL of P80D6. In some embodiments, the PEG-DPCA hydrogels comprise 5-65 mol % or 24-93 mg/mL of P80D6. In some embodiments, the PEG-DPCA hydrogels comprise about 8-80 g/mL of P7D3. In some embodiments, the PEG-DPCA hydrogels comprise about 25-95 g/mL of P80D6. In some embodiments, the PEG-DPCA hydrogels comprise about 8-80 g/mL of P7D3 and about 25-95 g/mL of P80D6.

In some embodiments, the PEG-DPCA hydrogels, such as the Exemplary PEG-DPCA Hydrogels (including the Exemplary P7D3/P80D6 Hydrogels), further comprise a pharmaceutically acceptable carrier. As used herein, "pharmaceutically acceptable vehicle" or "pharmaceutically acceptable carrier" are used interchangeably and refer to solvents, dispersion media, coatings, antibacterial and antifungal agents, isotonic and absorption delaying agents, and the like, that are compatible with pharmaceutical administration and comply with the applicable standards and regulations, e.g., the pharmacopeial standards set forth in the United States Pharmacopeia and the National Formulary (USP-NF) book, for pharmaceutical administration. Thus, for example, unsterile water is excluded as a pharmaceutically acceptable carrier for, at least, intravenous administration. Pharmaceutically acceptable vehicles include those known in the art. See, e.g., Remington: The Science and Practice of Pharmacy 20th ed (2000) Lippincott Williams & Wilkins, Baltimore, MD Exemplary Compositions: In some embodiments, the present invention is directed to compositions that comprise or consist of one or more PEG-DPCA hydrogels such as the Exemplary PEG-DPCA Hydrogels (including the Exemplary P7D3/P80D6 Hydrogels). In some embodiments, the compositions further comprise a pharmaceutically acceptable carrier. The compositions may be formulated for the intended route of delivery, including topical, intravenous, intramuscular, intra peritoneal, subcutaneous, intraocular, intrathecal, intraarticular, intrasynovial, cisternal, intrahepatic, intralesional injection, intracranial injection, infusion, oral and/or inhaled routes of administration using methods known in the art. The compositions may include one or more of the following: pH buffered solutions, adjuvants (e.g., preservatives, wetting agents, emulsifying agents, and dispersing agents), liposomal formulations, nanoparticles, dispersions, suspensions, or emulsions, as well as sterile powders for reconstitution into sterile injectable solutions or dispersions.

In some embodiments, the sol-gel properties of the hydrogels provided herein aid in the formulation of the PEG-DPCA hydrogel for specific applications. For example, the shear and/or heat thinning properties of the hydrogels provided herein is useful because it aids in injecting into a tissue (i.e., in a liquid form) whereupon it re-forms a gel, thus providing a means for localization of the PEG-DPCA at a particular site. In some embodiments, the PEG-DPCA is provided in liquid form and maintained in liquid form for example as direct intramuscular or intraperitoneal delivery. In some embodiments, solid (e.g., gel form) formulations of PEG-DPCA are useful for oral administration.

Exemplary Treatments with Biomacromolecule-DPCA Hydrogels, Such as PEG-DPCA Hydrogels In some embodiments, a biomacromolecule-DPCA hydrogel, such as a DPCA-PEG hydrogel or composition containing one or more DPCA-PEG hydrogels is used to treat an animal. In some embodiments, the treated animal is a human. In some embodiments, the treated animal is a non-human animal, such as a companion animal (e.g., cat, dog, rabbit, bird). or a livestock, commercial, or farm animal (e.g., cow, pig, sheep, goat, chicken, duck). In some embodiments, the treated animal is a mammal. In some embodiments, the treated animal is a non-mammal, such as a bird or reptile.

In some embodiments, biomacromolecule-DPCA hydrogel, such as a DPCA-PEG hydrogel or composition containing one or more DPCA-PEG hydrogels is used to treat a specific disease or condition that effects one or more tissues or organs including skin, nervous system CNS and PNS such as optic nerve, brain, cells in the eye, cells in the ear related to hearing, retinal and corneal wounds, cartilage articular in joints and elastic in ear pinnae, tendon, myocardium, lung, vascular tissue, blood vessels, muscle, skeletal and smooth, digits, limbs, organ transplants, bone, pancreatic acinear cells, beta cells, kidney, liver, gut, hair growth, periodontal injuries and disease with bone, gum, pulp, or periodontal ligament. In some embodiments, biomacromolecule-DPCA hydrogel, such as a DPCA-PEG hydrogel or composition containing one or more DPCA-PEG hydrogels is used to treat hard tissue. In some embodiments, biomacromolecule-DPCA hydrogel, such as a DPCA-PEG hydrogel or composition containing one or more DPCA-PEG hydrogels is used to treat soft tissue. In some embodiments, biomacromolecule-DPCA hydrogel, such as a DPCA-PEG hydrogel or composition containing one or more DPCA-PEG hydrogels is used to treat one or more organs.

Treatment with a biomacromolecule-DPCA hydrogel, such as a DPCA-PEG hydrogel or composition thereof includes single treatments and multiple treatments. Multiple treatments includes application or administration at one or more time points and/or to one or more areas or entry points of the treated subject. For example, treatment includes daily, weekly and monthly administration, as well as administration once, twice, thrice or more than 3 times per day.

In some embodiments, the present invention is directed to inducing, improving, enhancing, or increasing tissue regeneration and/or cellular repair in a cell or tissue, which comprises contacting the cell or tissue with one or more biomacromolecule-DPCA hydrogel, such as the Exemplary PEG-DPCA Hydrogels (including the Exemplary P7D3/P80D6 Hydrogels), or a composition thereof. In some embodiments, the present invention is directed to inducing, improving, enhancing, or increasing tissue regeneration and/or cellular repair in a subject, which comprises administering to the subject one or more PEG-DPCA hydrogels, such as the Exemplary PEG-DPCA Hydrogels (including the Exemplary P7D3/P80D6 Hydrogels), or a composition thereof. In some embodiments, the present invention is directed to upregulating or increasing the release of hypoxia-inducible factor 1α (HIF-1α) in a subject, which comprises administering to the subject one or more PEG-DPCA hydrogels, such as the Exemplary PEG-DPCA Hydrogels (including the Exemplary P7D3/P80D6 Hydrogels), or a composition thereof. The one or more PEG-DPCA hydrogels or composition thereof may be administered to a subject by any suitable route including oral, topical, transdermal, subcutaneous, intranasal, inhalation, intramuscular, and intravascular administration. In some embodiments, the methods comprise systemically or locally administering the one or more PEG-DPCA hydrogels to the subject. In some embodiments, the methods comprise topically administering the one or more PEG-DPCA hydrogels to the subject to the site of desired epimorphic tissue regeneration or cellular repair. In some embodiments, the methods comprise administering the one or more PEG-DPCA hydrogels to the subject at a site distal from where the epimorphic tissue regeneration or cellular repair is desired. In some embodiments, the methods comprise administering the one or more PEG-DPCA hydrogels to the subject at a site local or adjacent to where epimorphic tissue regeneration or cellular repair is desired. In some embodiments, the methods include application both locally and distally to where epimorphic tissue regeneration or cellular repair is desired. In some embodiments, a composition comprising (a) the one or more PEG-DPCA hydrogels and (b) tissue or cells which were obtained from the subject to be treated, were obtained from a donor subject, or were cultivated or synthetically created is administered to the subject.

EMBODIMENTS

Embodiment P1. A PEG-DPCA conjugate comprising two or more DPCA groups at one terminal end of a PEG compound or at each terminal end of the PEG compound.

Embodiment P2. The PEG-DPCA conjugate of embodiment P1, wherein the PEG-DPCA conjugate has the formula $X_a$-PEG(A)-$X_b$, wherein X is DPCA, a and b represent the number of DPCA groups at each terminal end of the PEG compound, wherein (A) represents the structure of the PEG compound, and wherein the sum of a and b is equal to or greater than 2.

Embodiment P3. The PEG-DPCA conjugate of embodiment P1 or P2, wherein when a is 0, b is 1 or greater than 1, when a is 1, b is 2 or greater than 2 and when a is 3 or more than 3, b is 0, 1, 2, 3, 4, 5, 6, or more 6.

Embodiment P4. The PEG-DPCA conjugate of embodiment P1 or P2, wherein when a is 0, b is 2 or greater than 2, and when a is 1, b is 1 or greater than 1.

Embodiment P5. The PEG-DPCA conjugate according to any one of embodiments P1-P4, wherein the PEG compound is selected from the group consisting of linear PEG, branched PEG, multiarm PEG, star PEG.

Embodiment P6. The PEG-DPCA conjugate according to any one of embodiments P1-P4, wherein the PEG compound has an average molecular weight of about 250-20,000 Da, about 300-10,000 Da, about 400-9,000 Da, or about 500-8,000 Da.

Embodiment P7. The PEG-DPCA conjugate of embodiment P1, wherein said PEG-DPCA conjugate has structural Formula I or structural Formula II as follows:

(I)

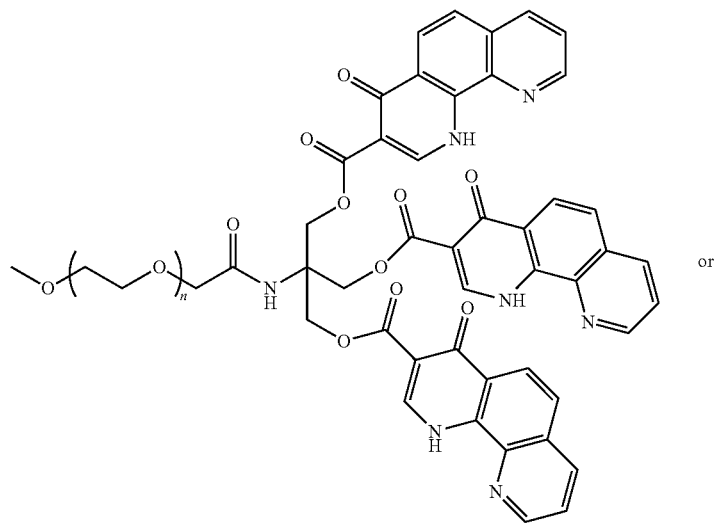

or (II)

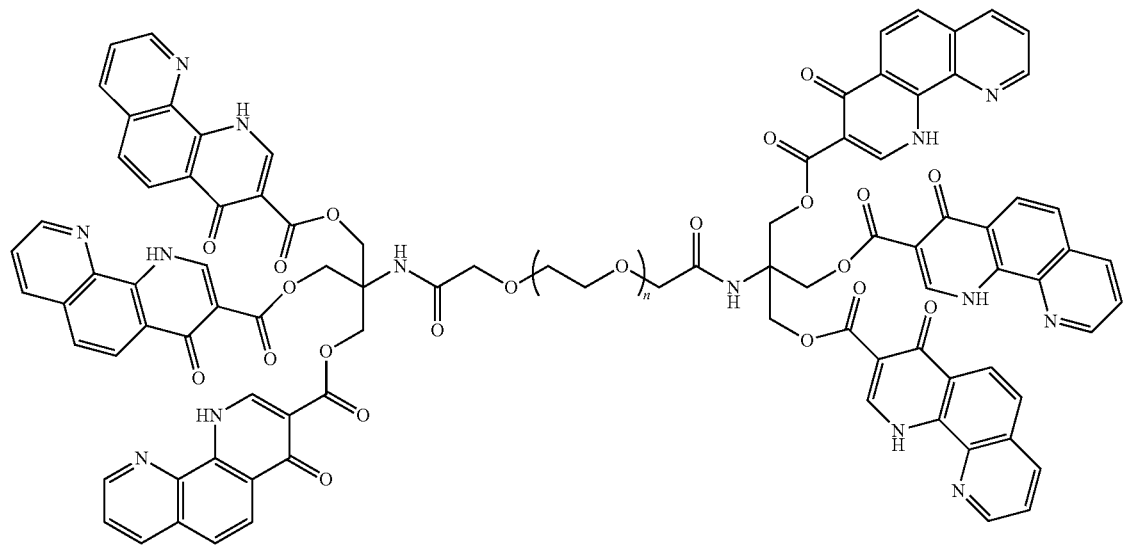

wherein n>1.

Embodiment P8. A composition comprising at least one PEG-DPCA conjugate according to any one of embodiments P1-P7.

Embodiment P9. A composition comprising two or more PEG-DPCA conjugates according to any one of embodiments P1-P7.

Embodiment P10. The composition of embodiments P8 or P9, wherein the composition comprises at least about 1 mg/mL, at least about 3 mg/mL, at least about 5 mg/mL, at least about 8 mg/mL, at least about 10 mg/mL, at least about 11 mg/mL, at least about 15 mg/mL, at least about 20 mg/mL, at least about 32 mg/mL, at least about 39 mg/mL, at least about 48 mg/mL, at least about 59 mg/mL, at least about 66 mg/mL, at least about 76 mg/mL, at least about 88 mg/mL, or at least about 100 mg/mL of the PEG-DPCA conjugate.

Embodiment P11. The composition of embodiments P10, wherein the conjugate comprises P7D3.

Embodiment P12. The composition of embodiments P8 or P9 wherein the composition comprises at least about 12 mg/mL, at least about 24 mg/mL, at least about 34 mg/mL, at least about 41 mg/mL, at least about 52 mg/mL, at least about 62 mg/mL, at least about 68 mg/mL, at least about 80 mg/mL, at least about 85 mg/mL, at least about 89 mg/mL, at least about 90 mg/mL, at least about 92 mg/mL, at least about 95 mg/mL, at least about 97 mg/mL, at least about 99 mg/mL, or at least about 100 mg/mL of the PEG-DPCA conjugate.

Embodiment P13. The composition of embodiment P12, wherein the conjugate comprises P80D6.

Embodiment P14. The composition of embodiment P9, wherein the composition is selected from the group consisting of:
a) about 100 mg/mL of the PEG-DPCA conjugate having Structural Formula I and about 0 mg/mL of the PEG-DPCA conjugate having Structural Formula II;
b) about 88 mg/mL of the PEG-DPCA conjugate having Structural Formula I and about 12 mg/mL of the PEG-DPCA conjugate having Structural Formula II;
c) about 76 mg/mL of the PEG-DPCA conjugate having Structural Formula I and about 24 mg/mL of the PEG-DPCA conjugate having Structural Formula II;
d) about 66 mg/mL of the PEG-DPCA conjugate having Structural Formula I and about 34 mg/mL of the PEG-DPCA conjugate having Structural Formula II;
e) about 59 mg/mL of the PEG-DPCA conjugate having Structural Formula I and about 41 mg/mL of the PEG-DPCA conjugate having Structural Formula II;
f) about 48 mg/mL of the PEG-DPCA conjugate having Structural Formula I and about 52 mg/mL of the PEG-DPCA conjugate having Structural Formula II;
g) about 39 mg/mL of the PEG-DPCA conjugate having Structural Formula I and about 61 mg/mL of the PEG-DPCA conjugate having Structural Formula II;
h) about 32 mg/mL of the PEG-DPCA conjugate having Structural Formula I and about 68 mg/mL of the PEG-DPCA conjugate having Structural Formula II;
i) about 20 mg/mL of the PEG-DPCA conjugate having Structural Formula I and about 80 mg/mL of the PEG-DPCA conjugate having Structural Formula II;
j) about 15 mg/mL of the PEG-DPCA conjugate having Structural Formula I and about 85 mg/mL of the PEG-DPCA conjugate having Structural Formula II;
k) about 11 mg/mL of the PEG-DPCA conjugate having Structural Formula I and about 89 mg/mL of the PEG-DPCA conjugate having Structural Formula II;
l) about 10 mg/mL of the PEG-DPCA conjugate having Structural Formula I and about 90 mg/mL of the PEG-DPCA conjugate having Structural Formula II;
m) about 8 mg/mL of the PEG-DPCA conjugate having Structural Formula I and about 92 mg/mL of the PEG-DPCA conjugate having Structural Formula II;
n) about 5 mg/mL of the PEG-DPCA conjugate having Structural Formula I and about 95 mg/mL of the PEG-DPCA conjugate having Structural Formula II;
o) about 3 mg/mL of the PEG-DPCA conjugate having Structural Formula I and about 97 mg/mL of the PEG-DPCA conjugate having Structural Formula II;
p) about 1 mg/mL of the PEG-DPCA conjugate having Structural Formula I and about 99 mg/mL of the PEG-DPCA conjugate having Structural Formula II; and
q) about 0 mg/mL of the PEG-DPCA conjugate having Structural Formula I and about 100 mg/mL of the PEG-DPCA conjugate having Structural Formula II.

Embodiment P15. The composition of embodiment P14, wherein the PEG-DPCA conjugate having structural Formula I is P7D3 and/or the PEG-DPCA conjugate having structural Formula II is P80D6.

Embodiment P16. A method of upregulating or increasing release of hypoxia-inducible factor 1α (HIF-1α) in a subject, which comprises administering to the subject one or more PEG-DPCA conjugates according to any one of embodiments P1-P7 or a composition according to any one of embodiments P8-P15.

Embodiment P17. A method of inducing, improving, enhancing, or increasing epimorphic tissue regeneration and/or cellular repair, which comprises contacting a cell or tissue with one or more PEG-DPCA conjugates according to any one of embodiments P1-P7 or a composition according to any one of embodiments P8-P15.

Embodiment P18. The method of embodiment P17, wherein the cell or tissue is ex-vivo or in vivo.

Embodiment P19. The method of embodiment P17 or P18, wherein the cell or tissue is derived from skin, bone or cartilage.

Embodiment P20. A method of inducing, improving, enhancing, or increasing epimorphic tissue regeneration and/or cellular repair in a subject, which comprises administering to the subject one or more PEG-DPCA conjugates according to any one of embodiments P1-P7 or a composition according to any one of embodiments P8-P15.

Embodiment P21. The method of embodiment P20, wherein the one or more conjugates or the composition is administered topically to the subject.

Embodiment P22. The method of embodiment P20, wherein the one or more conjugates or the composition is administered systemically to the subject.

Embodiment P23. The method according to any one of embodiments P20-P22, wherein the one or more PEG-DPCA conjugates or composition thereof is applied to a site distal to the site identified for epimorphic regeneration or cellular repair.

Embodiment P24. The method according to any one of embodiments P20-P23, wherein the site of epimorphic tissue regeneration and/or cellular repair comprises skin, hair, eye, ear, nervous system, bone, limb, organ or vascular tissue.

Embodiment P25. A method of reducing or reversing one or more symptoms of aging, comprising administering to a subject one or more PEG-DPCA conjugates according to any one of embodiments P1-P7 or a composition according to any one of embodiments P8-P15, wherein the administration improves the rate or the quality of epimorphic regeneration.

Embodiment P26. The method of embodiment P25, wherein the rate or the quality of epimorphic regeneration is improved for skin, bone, or hair.

Embodiment P27. A method of reducing or reversing one or more symptoms of aging, comprising administering to a subject one or more PEG-DPCA conjugates according to any one of embodiments P1-P7 or a composition according to any one of embodiments P8-P15, wherein the administration reduces or slows the rate of tissue or cell degeneration or death.

Embodiment P28. The method of embodiment P27, wherein the tissue or cell comprises skin, hair, bone or cartilage.

Embodiment P29. A method of inducing epimorphic tissue regeneration, comprising administering to a subject one or more PEG-DPCA conjugates according to any one of embodiments P1-P7 or a composition according to any one of embodiments P8-P15, wherein the administration results in the healing of a skin wound, a skin ulcer, the growth of bone, the growth of cartilage, the growth of hair and any combination thereof.

Embodiment P30. A method of inducing nerve growth, comprising administering to a subject one or more PEG-DPCA conjugates according to any one of embodiments P1-P7 or a composition according to any one of embodiments P8-P15, wherein the administration results in the growth of nerve cells.

Embodiment P31. A method of treating osteoporosis, comprising administering to a subject one or more PEG-DPCA conjugates according to any one of embodiments P1-P7 or a composition according to any one of embodiments P8-P15.

Embodiment P32. A method of improving density and quality of the bone, comprising administering to a subject one or more PEG-DPCA conjugates according to any one of embodiments P1-P7 or a composition according to any one of embodiments P8-P15, and wherein the administration results in the improvement of the quality or density of bone of the subject as compared to the bone prior to treatment.

Embodiment P33. A method of treating fibrosis, comprising administering to a subject one or more PEG-DPCA conjugates according to any one of claims embodiments P1-P7 or a composition according to any one of embodiments P8-P15.

Embodiment P34. The method of embodiment P33, wherein the fibrosis is kidney fibrosis or liver fibrosis.

Embodiment P35. A method of treating tissue injury, comprising administering to a subject one or more PEG-DPCA conjugates according to any one of embodiments P1-P7 or a composition according to any one of embodiments P8-P15, wherein the administration improves the health of the tissue as compared to the tissue prior to treatment.

Embodiment P36. The method of embodiment P35, wherein the tissue is kidney tissue or liver tissue.

Embodiment P37. A method of inducing vasculogenesis, comprising administering to a subject one or more PEG-DPCA conjugates according to any one of embodiments P1-P7 or a composition according to any one of embodiments P8-P15, wherein the administration induced the formation of or maturation of mature blood vessels in the subject.

Further Embodiments

Embodiment 38. A conjugate comprising a biomacromolecule and a first DPCA group, wherein the biomacromolecule comprises a first terminal end and a second terminal end and wherein the first DPCA group is covalently joined directly or indirectly to the first terminal end or the second terminal end.

Embodiment 39. The conjugate of embodiment 38 further comprising a second DPCA group covalently joined directly or indirectly to the first terminal end or the second terminal end.

Embodiment 40. The conjugate of embodiment 38 or 39, wherein the DPCA is covalently joined to the biomacromolecule by a linker.

Embodiment 41. The conjugate of any one of embodiments 38-40, wherein the linker is capable of being cleaved in vivo.

Embodiment 42. The conjugate of embodiment 41, wherein said cleavage is hydrolytic cleavage.

Embodiment 43. The conjugate of embodiment 41 or 42, wherein the linker comprises a group selected from the group consisting of ester, anhydride, peptide, thioester, hydrazine, disulfide, azo, Schiff bases and acetal.

Embodiment 44. The conjugate of any one of embodiments 38-43, wherein said linker has the formula -$L^1$-$L^2$-$L^3$-, wherein:

$L^1$ and $L^3$ are independently a bond, —O—, —S—, —NH—, —C(O)NH—, —C(O)—, —S(O)$_{n1}$NH—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene, wherein n1 is an integer from 1 to 3; and $L^2$ is —C(O)O—, —C(O)—O—C(O)—, a peptide linker, —C(O)S—, —NH—NH—, —S—S—, —N=N—, —C(N(R'))—, —C(O$R^2$)(O$R^3$)—, wherein $R^1$, $R^2$, and $R^3$ are independently substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

Embodiment 45. The conjugate of any one of embodiments 38-44, wherein the conjugate has the formula: (X-$L^3$-$L^2$-$L^1$)$_{n2}$-A-($L^1$-$L^2$-$L^3$-X)$_{n3}$, wherein: X is a DPCA group; n2 and n3 are independently integers from 1 to 10; and A is said biomacromolecule.

Embodiment 46. The conjugate of embodiment 45, wherein n2 and n3 are independently integers from 1 to 3.

Embodiment 47. The conjugate of any one of embodiments 38-44, wherein the conjugate has the formula: (X-$L^3$-$L^2$-$L^1$)$_{n2}$-A, wherein: X is a DPCA group; n2 is an integer from 1 to 10; and A is said biomacromolecule.

Embodiment 48. The conjugate of embodiment 47, wherein n2 is an integer from 1 to 3.

Embodiment 49. The conjugate according to any of any one of embodiments 38-48, wherein the biomacromolecule is selected from the group consisting of PEG, PEG-PPO block copolymer, dextran, alginate, hyaluronic acid, cyclodextrins, cellulose, hydroxypropylcellulose, chitosan, gelatin, PGA/PLA/PCL and copolymers thereof, PGA/PLA/PCL block copolymers with PEG, poly(acrylic acid), poly(methacrylic acid), poly(vinyl alcohol), poly(hydroxyethyl methacrylate), and poly(N-isopropyl acrylamide) (PNIPAAm).

Embodiment 50. The conjugate according to any one of embodiments 38-49, wherein the biomacromolecule is PEG.

Embodiment 51. The conjugate of any one of embodiments 38-50, wherein the PEG is a linear PEG, branched PEG, multiarm PEG, or star PEG.

Embodiment 52. The conjugate of embodiment 47 or 48, wherein the PEG has an average molecular weight of about 250-20,000 Da, about 300-10,000 Da, about 400-9,000 Da, or about 500-8,000 Da.

Embodiment 53. The conjugate of embodiment 38, wherein the conjugate comprises at least 2 DPCA groups.

Embodiment 54. The conjugate of embodiment 38, wherein the conjugate has structural Formula I or structural Formula II as follows:

Embodiment 55. A composition comprising at least one conjugate according to any one of embodiments 38-54.

Embodiment 56. A composition comprising two or more conjugates according to any one of embodiments 38-54.

Embodiment 57. The composition of embodiment 55 or 56, wherein one of the conjugate comprises P7D3.

Embodiment 58. The composition of embodiment 55 or 56, wherein one of the conjugates comprises P80D6.

Embodiment 59. The composition of embodiment 57 or 58, comprising P7D3 or P80D6.

Embodiment 60. The composition of embodiment 55, wherein the composition is selected from the group consisting of:
a) about 100 mg/mL of the PEG-DPCA conjugate having Structural Formula I and about 0 mg/mL of the PEG-DPCA conjugate having Structural Formula II;

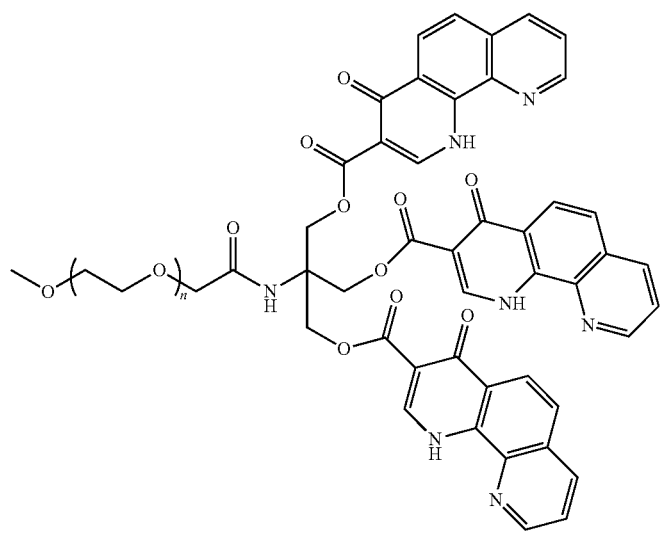

(I)

or

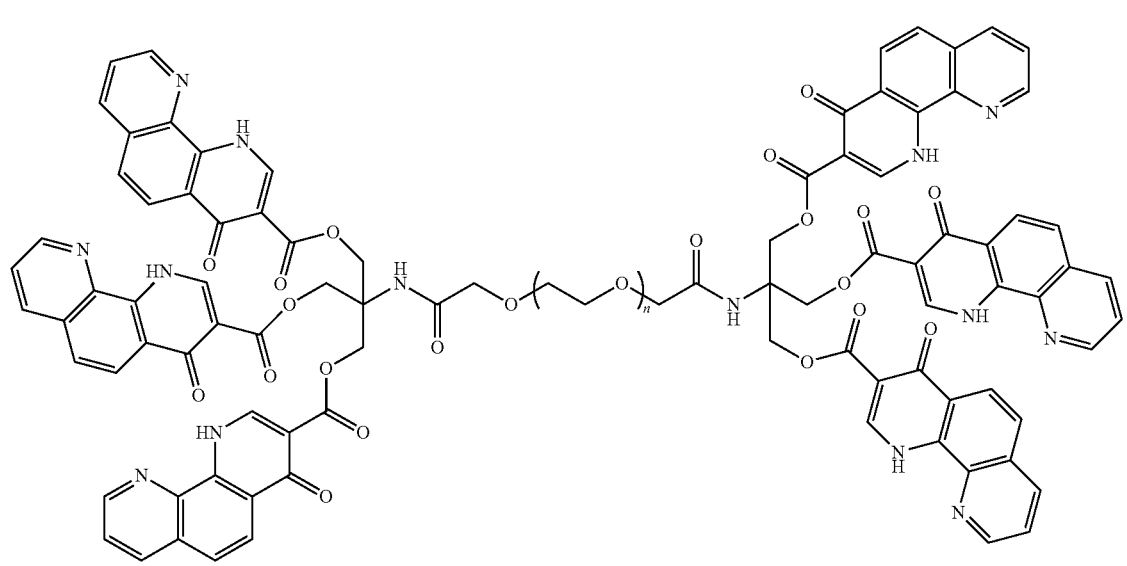

(II)

wherein n>1.

b) about 88 mg/mL of the PEG-DPCA conjugate having Structural Formula I and about 12 mg/mL of the PEG-DPCA conjugate having Structural Formula II;
c) about 76 mg/mL of the PEG-DPCA conjugate having Structural Formula I and about 24 mg/mL of the PEG-DPCA conjugate having Structural Formula II;
d) about 66 mg/mL of the PEG-DPCA conjugate having Structural Formula I and about 34 mg/mL of the PEG-DPCA conjugate having Structural Formula II;
e) about 59 mg/mL of the PEG-DPCA conjugate having Structural Formula I and about 41 mg/mL of the PEG-DPCA conjugate having Structural Formula II;
f) about 48 mg/mL of the PEG-DPCA conjugate having Structural Formula I and about 52 mg/mL of the PEG-DPCA conjugate having Structural Formula II;
g) about 39 mg/mL of the PEG-DPCA conjugate having Structural Formula I and about 61 mg/mL of the PEG-DPCA conjugate having Structural Formula II;
h) about 32 mg/mL of the PEG-DPCA conjugate having Structural Formula I and about 68 mg/mL of the PEG-DPCA conjugate having Structural Formula II;
i) about 20 mg/mL of the PEG-DPCA conjugate having Structural Formula I and about 80 mg/mL of the PEG-DPCA conjugate having Structural Formula II;
j) about 15 mg/mL of the PEG-DPCA conjugate having Structural Formula I and about 85 mg/mL of the PEG-DPCA conjugate having Structural Formula II;
k) about 11 mg/mL of the PEG-DPCA conjugate having Structural Formula I and about 89 mg/mL of the PEG-DPCA conjugate having Structural Formula II;
l) about 10 mg/mL of the PEG-DPCA conjugate having Structural Formula I and about 90 mg/mL of the PEG-DPCA conjugate having Structural Formula II;
m) about 8 mg/mL of the PEG-DPCA conjugate having Structural Formula I and about 92 mg/mL of the PEG-DPCA conjugate having Structural Formula II;
n) about 5 mg/mL of the PEG-DPCA conjugate having Structural Formula I and about 95 mg/mL of the PEG-DPCA conjugate having Structural Formula II;
o) about 3 mg/mL of the PEG-DPCA conjugate having Structural Formula I and about 97 mg/mL of the PEG-DPCA conjugate having Structural Formula II;
p) about 1 mg/mL of the PEG-DPCA conjugate having Structural Formula I and about 99 mg/mL of the PEG-DPCA conjugate having Structural Formula II; and
q) about 0 mg/mL of the PEG-DPCA conjugate having Structural Formula I and about 100 mg/mL of the PEG-DPCA conjugate having Structural Formula II.

Embodiment 61. The composition of embodiment 58, wherein the PEG-DPCA conjugate having structural Formula I is P7D3 and/or the PEG-DPCA conjugate having structural Formula II is P80D6.

Embodiment 62. The composition of embodiment 57 or 58, wherein the mol percentage ratio between structural Formula I and structural Formula II is selected from the group consisting of about 100:0, 97.5:2.5, 95:5, 92.5: 7.5, 90:10, 85:15, 80:20, 75:25, 62:38, 53:47, 45:55, 41:59, 35:65, 25:75, 15:85, 5:95, and 0:100.

Embodiment 63. A method of upregulating or increasing release of hypoxia-inducible factor 1α (HIF-1α) in a subject, which comprises administering to the subject one or more conjugates according to any one of embodiments 38-54 or a composition according to any one of embodiments 55-62.

Embodiment 64. A method of inducing, improving, enhancing, or increasing epimorphic tissue regeneration and/or cellular repair, which comprises contacting a cell or tissue with one or more conjugates according to any one of embodiments 38-54 or a composition according to any one of embodiments 54-61.

Embodiment 65. The method of embodiment 64, wherein the cell or tissue is ex-vivo or in vivo.

Embodiment 66. The method of embodiment 64 or 65, wherein the cell or tissue is derived from skin, bone or cartilage.

Embodiment 67. A method of inducing, improving, enhancing, or increasing epimorphic tissue regeneration and/or cellular repair in a subject, which comprises administering to the subject one or more conjugates according to any one of embodiments 38-54 or a composition according to any one of embodiments 55-62.

Embodiment 68. The method of embodiment 67, wherein the one or more conjugates or the composition is administered topically to the subject.

Embodiment 69. The method of embodiment 67, wherein the one or more conjugates or the composition is administered systemically to the subject.

Embodiment 70. The method according to any one of embodiments 64-66, wherein the one or more conjugates or composition is applied to a site distal to the site identified for epimorphic regeneration or cellular repair.

Embodiment 71. The method according to any one of embodiments 64-66, wherein the site of epimorphic tissue regeneration and/or cellular repair comprises skin, hair, eye, ear, nervous system, bone, limb, organ or vascular tissue.

Embodiment 72. A method of reducing or reversing one or more symptoms of aging, comprising administering to a subject one or more conjugates according to any one of embodiments 38-54 or a composition according to any one of embodiments 55-62, wherein the administration improves the rate or the quality of epimorphic regeneration.

Embodiment 73. The method of embodiment 72, wherein the rate or the quality of epimorphic regeneration is improved for skin, bone, or hair.

Embodiment 74. A method of reducing or reversing one or more symptoms of aging, comprising administering to a subject one or more conjugates according to any one of embodiments 38-54 or a composition according to any one of embodiments 55-62, wherein the administration reduces or slows the rate of tissue or cell degeneration or death.

Embodiment 75. The method of embodiment 74, wherein the tissue or cell comprises skin, hair, bone or cartilage.

Embodiment 76. A method of inducing epimorphic tissue regeneration, comprising administering to a subject one or more conjugates according to any one of embodiments 38-54 or a composition according to any one of embodiments 55-62, wherein the administration results in the healing of a skin wound, a skin ulcer, the growth of bone, the growth of cartilage, the growth of hair and any combination thereof.

Embodiment 77. A method of inducing nerve growth, comprising administering to a subject one or more conjugates according to any one of embodiments 38-54 or a composition according to any one of embodiments 55-62, wherein the administration results in the growth of nerve cells.

Embodiment 78. A method of treating osteoporosis, comprising administering to a subject one or more conjugates according to any one of embodiments 38-54 or a composition according to any one of embodiments 55-62.

Embodiment 79. A method of improving density and quality of the bone, comprising administering to a subject one or more conjugates according to any one of embodiments 38-54 or a composition according to any one of embodiments 55-62, and wherein the administration results in the improvement of the quality or density of bone of the subject as compared to the bone prior to treatment.

Embodiment 80. A method of treating fibrosis, comprising administering to a subject one or more conjugates according to any one of embodiments 38-54 or a composition according to any one of embodiments 55-62.

Embodiment 81. The method of embodiment 80, wherein the fibrosis is kidney fibrosis or liver fibrosis.

Embodiment 82. A method of treating tissue injury, comprising administering to a subject one or more conjugates according to any one of embodiments 38-54 or a composition according to any one of embodiments 55-62, wherein the administration improves the health of the tissue as compared to the tissue prior to treatment.

Embodiment 83. The method of embodiment 82, wherein the tissue is kidney tissue or liver tissue.

Embodiment 84. A method of inducing vasculogenesis, comprising administering to a subject one or more conjugates according to any one of embodiments 38-54 or a composition according to any one of embodiments 55-62, wherein the administration induced the formation of or maturation of mature blood vessels in the subject.

EXAMPLES

The following examples are intended to illustrate but not to limit the invention.

1,4-DPCA Activation

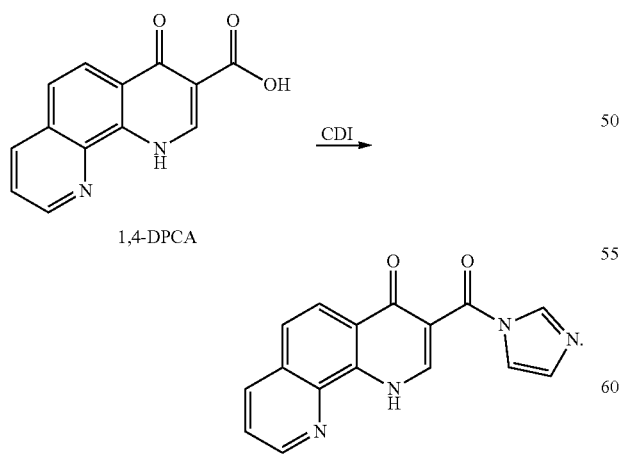

The activated form of 1,4-DPCA is used to conjugate DPCA to an appropriately functionalized biopolymer or synthetic polymer.

Chemical conversion of hydroxyl functional group of a biopolymer or synthetic polymer to an acid

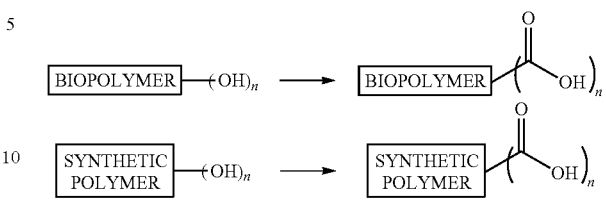

It is understood that any appropriate oxidant (TEMPO, for example) may be used. It is further understood that the alcohol group may be located anywhere in the polymer, for example as a side chain or as a terminal group.

Schematic illustration of a generalized approach to conjugating 1,4-DPCA to a biopolymer or synthetic polymer.

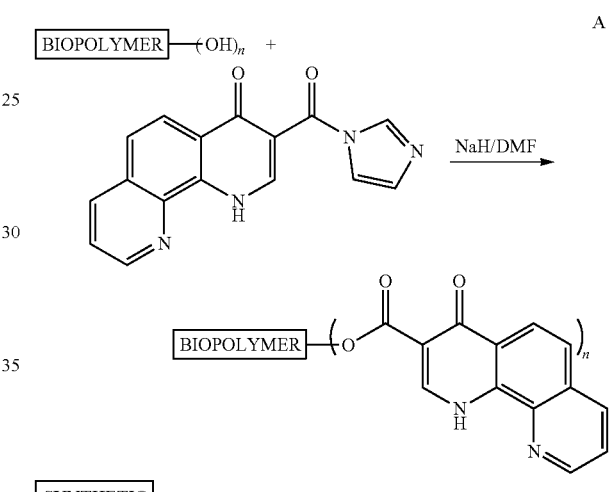

A

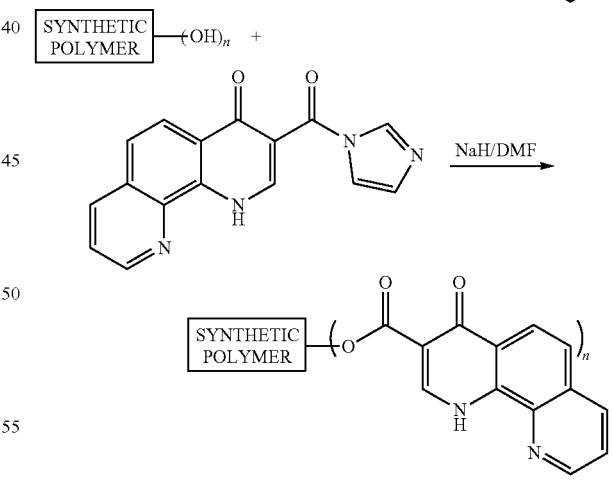

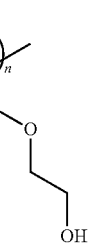

B

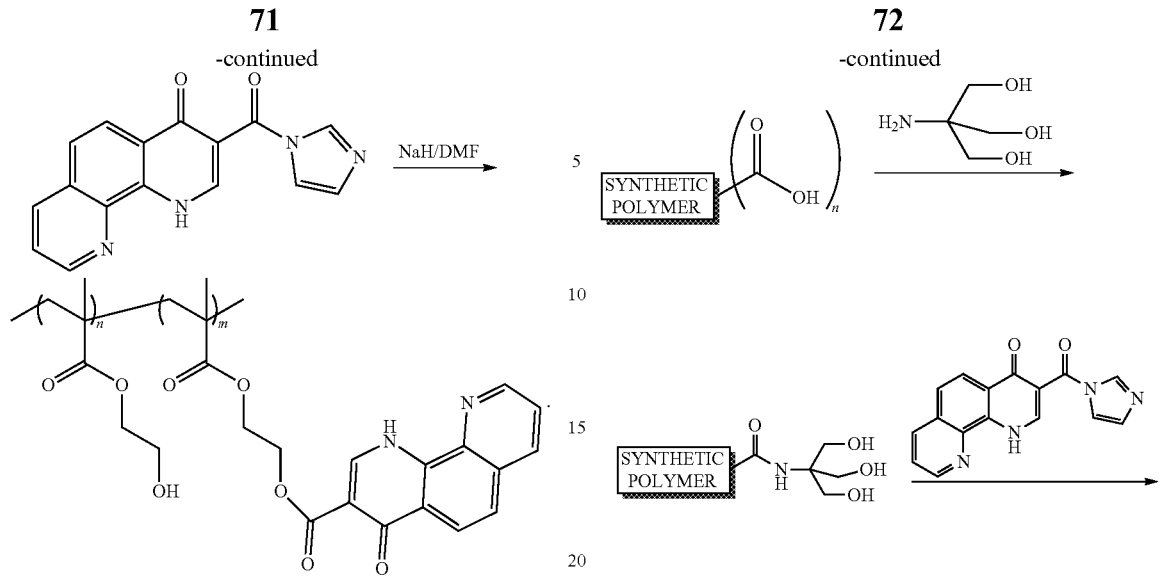
A. Conjugation of DPCA to hydroxyl-containing biopolymer or synthetic polymer.
B. Specific illustrative example of reaction scheme that may be used to conjugate 1,4-DPCA to poly(hydroxyethyl methacrylate).
Schematic illustration of a generalized approach to conjugating 1,4-DPCA to a biopolymer or synthetic polymer via a trivalent linker.
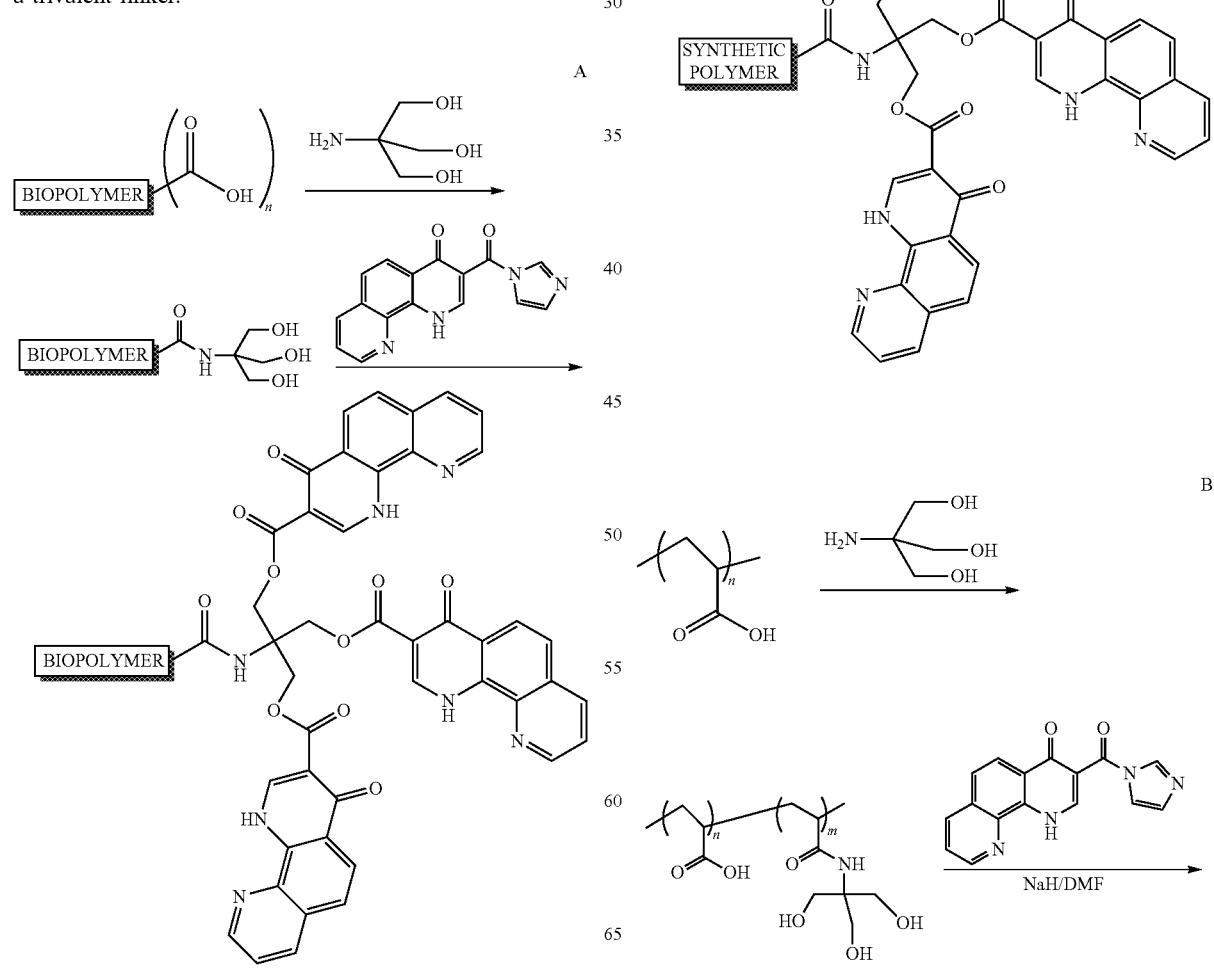

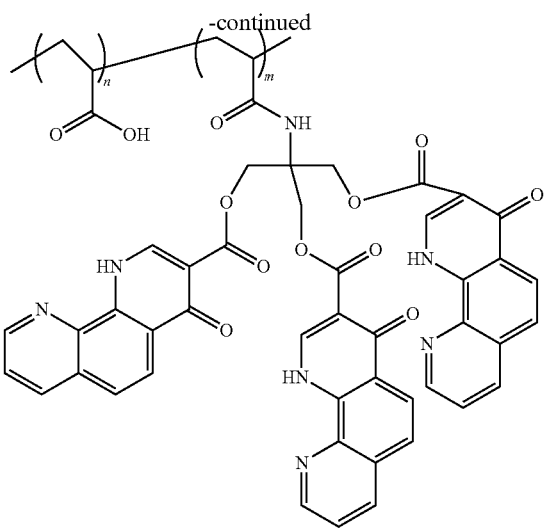

A. Conjugation of trivalent linker to an acid-containing biopolymer or synthetic polymer followed by conjugation of DPCA.
B. Specific illustrative example of reaction scheme that may be used to conjugate 1,4-DPCA to poly(acrylic acid) via a trivalent linker.

Figure 2A:
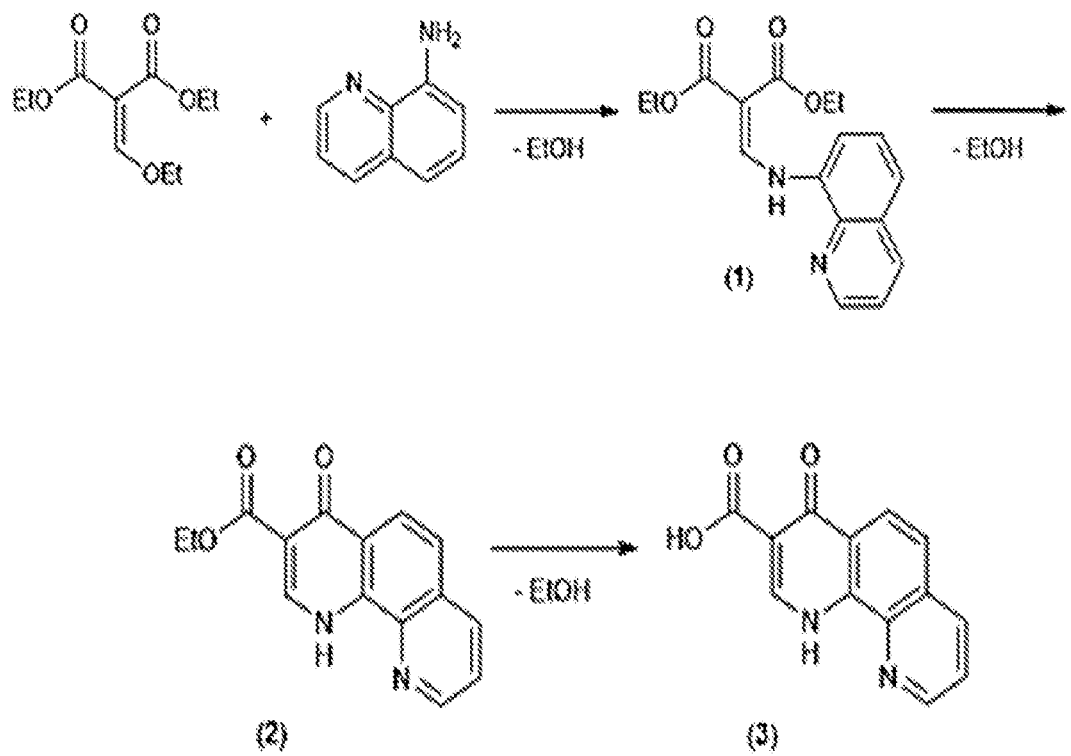
FIGS. 2A-2D: Synthesis of DPCA and PEG-DPCA conjugates (FIGS. 2A-2C). $^1$H NMR and $^{13}$C NMR of DPCA in DMSO-d6 (FIG. 2D).
Figure 2B:
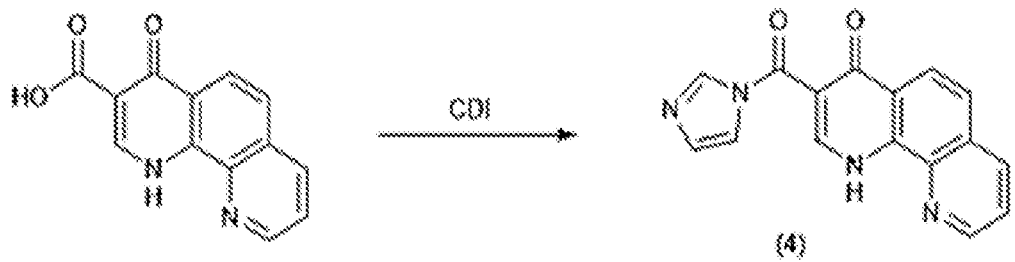
Figure 2C:
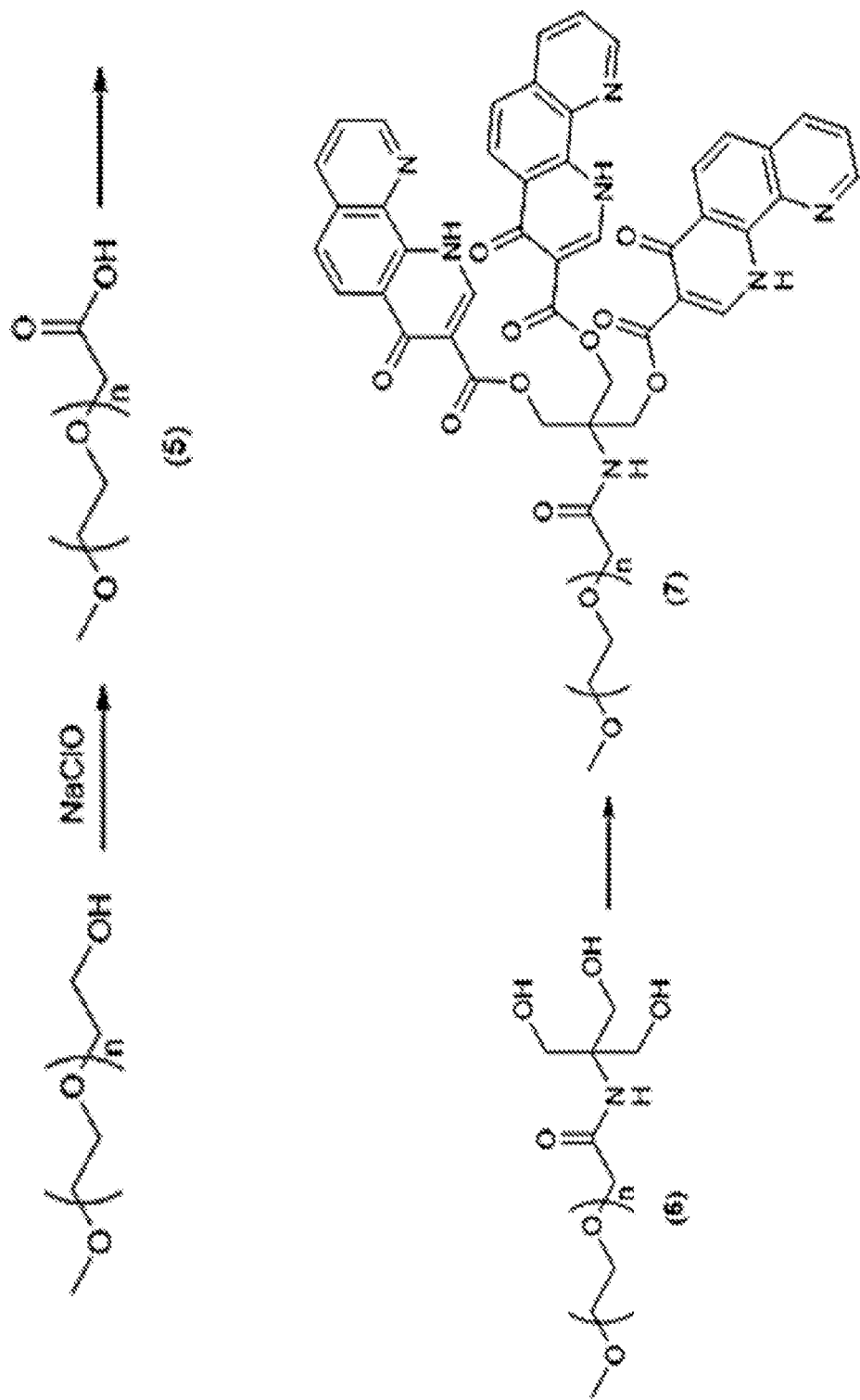
Figure 2D:
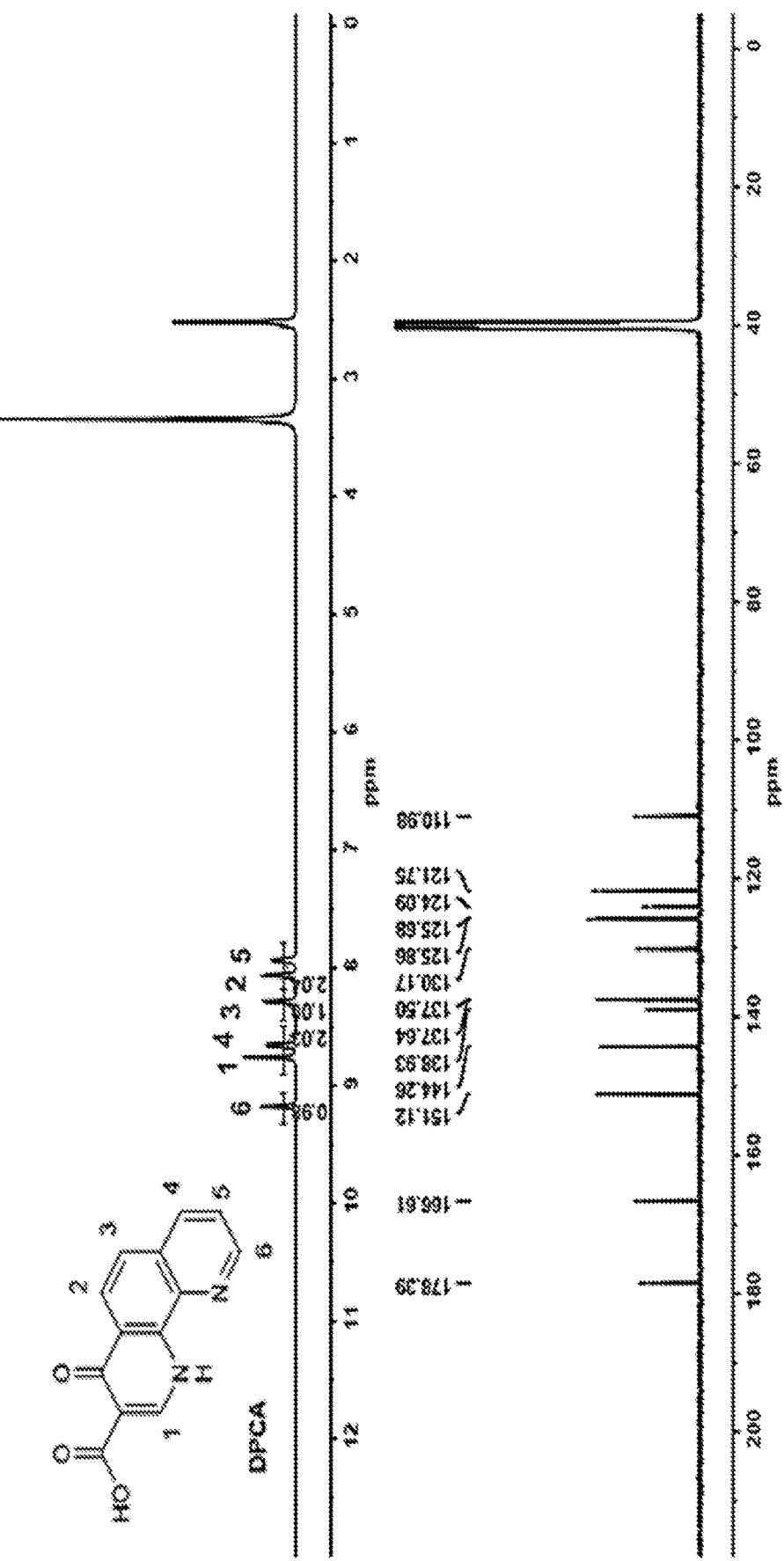

Example 1—Synthesis of PEG-Triol 1,4-dihydrophenonthroline-4-one-3-carboxylic acid (DPCA) (3) and DPCA-Im (4) were synthesized using methods in the art according to the synthesis schemes shown in FIGS. 2A and 2B.

Synthesis of 1,4-dihydrophenonthroline-4-one-3-carboxylic acid (DPCA) (3). 8-aminoquinoline (14.4 g, 100 mmol) and diethyl ethoxymethylenemalonate (22.7 g, 105 mmol) were heated to 100° C. for 2 hours and then added diphenylether (300 mL), refluxed (250° C.) for 5 hours, and cooled to room temperature. The precipitate product (2) was separated by centrifugation, washed with 100 mL hexane twice, and then washed with 50 mL diethyl ether. After drying under vacuum overnight, the brown powder was combined with 500 mL 10% (w/v) KOH and refluxed for 2 hours, cooled to 5° C., precipitated with 120 mL HCl, filtered, washed with DI water, and dried under vacuum overnight to afford crude product (3) as a brown powder (10 g, 41 mmol, 41%). The crude product was recrystallized in DMF before the next step.

Synthesis of DPCA-Im (4). DPCA (8 g, 33 mmol) was combined with DMF (150 mL), then added 1,1'-carbonyldiimidazole (16 g, 100 mmol). The mixture was stirred at 100° C. for 3 hours, and then cooled to room temperature. The product (4) was separated by centrifugation and washed with diethyl ether, then dried under vacuum overnight (9 g, 90%).

Synthesis of PEG-triol (6). PEG (10 mmol), TEMPO (0.5 g), NaBr (0.5 g) was dissolved in DI water (400 mL), and NaClO solution (10-15%, 40 mL) was added. pH was adjusted to 10 by NaOH solution (30%), and then the reaction was stirred at room temperature for 30 minutes. Ethanol (20 mL) was added to quench the reaction. pH was adjusted to 2 by HCl (10%). The solution was extracted by dichloromethane (DCM, 100 mL) 4 times. The combined organic solution was then washed with brine, dried by NaSO$_4$, filtered, and concentrated under vacuum to get product PEG-COOH (5). 5 (2 mmol), tromethamine (4 mmol), HBTU (3 mmol) and DIPEA (4 mmol) were dissolved in DMF (10 mL) and stirred at 37° C. for 12 hours. The product (6) was precipitated in diethyl ether (−20° C.) and dissolved in DCM (100 mL), washed with 5% HCl three times, washed with brine, dried with NaSO$_4$, filtered, concentrated under vacuum, precipitated in diethyl ether (−20° C.), and dried under vacuum overnight.

Example 2 Synthesis of PEG-DPCA Conjugates

Figure 3A:
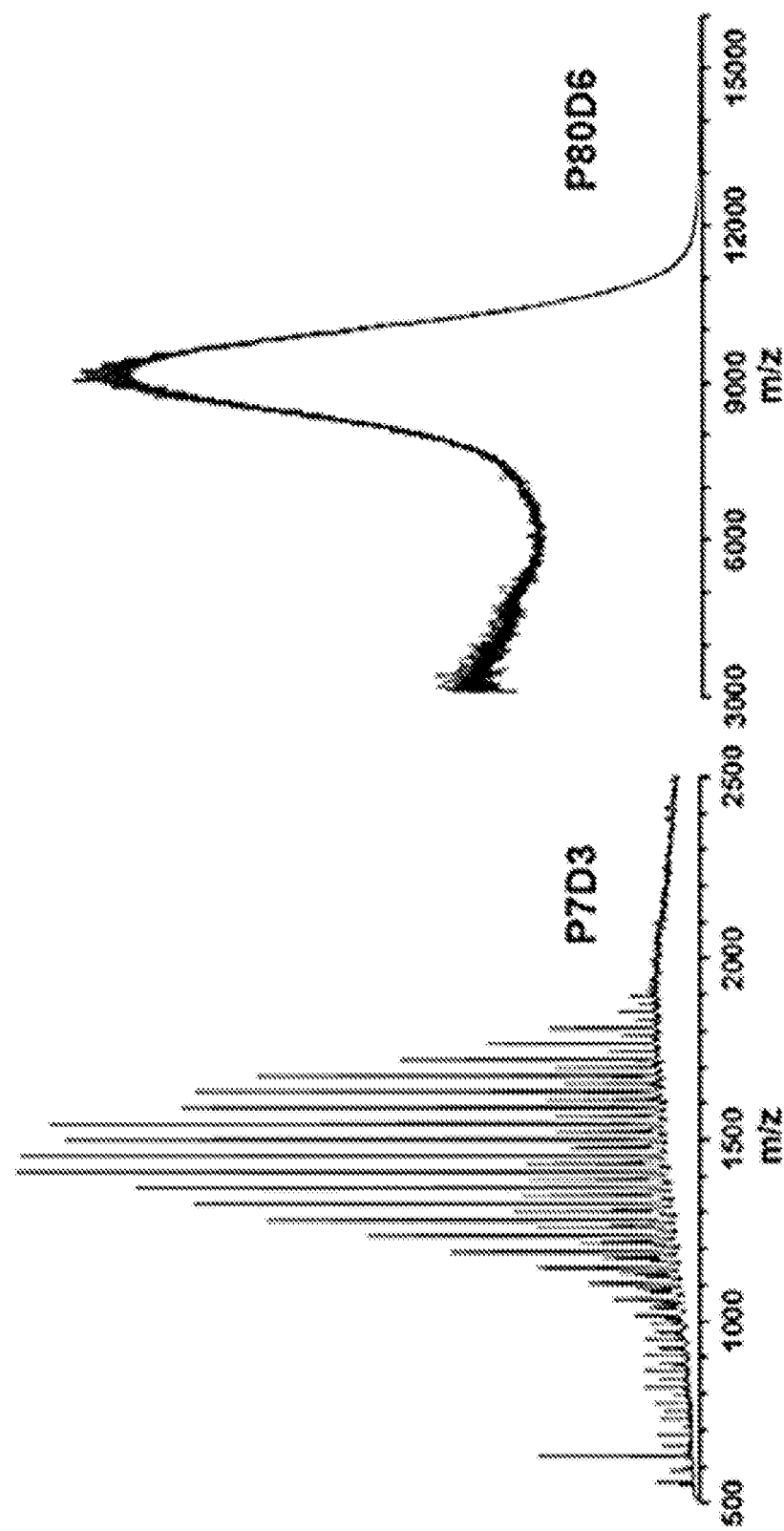
FIGS. 3A and 3B: MALDI (FIG. 3A) and $^1$H NMR spectra (FIG. 3B) of P7D3 and P80D6.
Figure 3B:
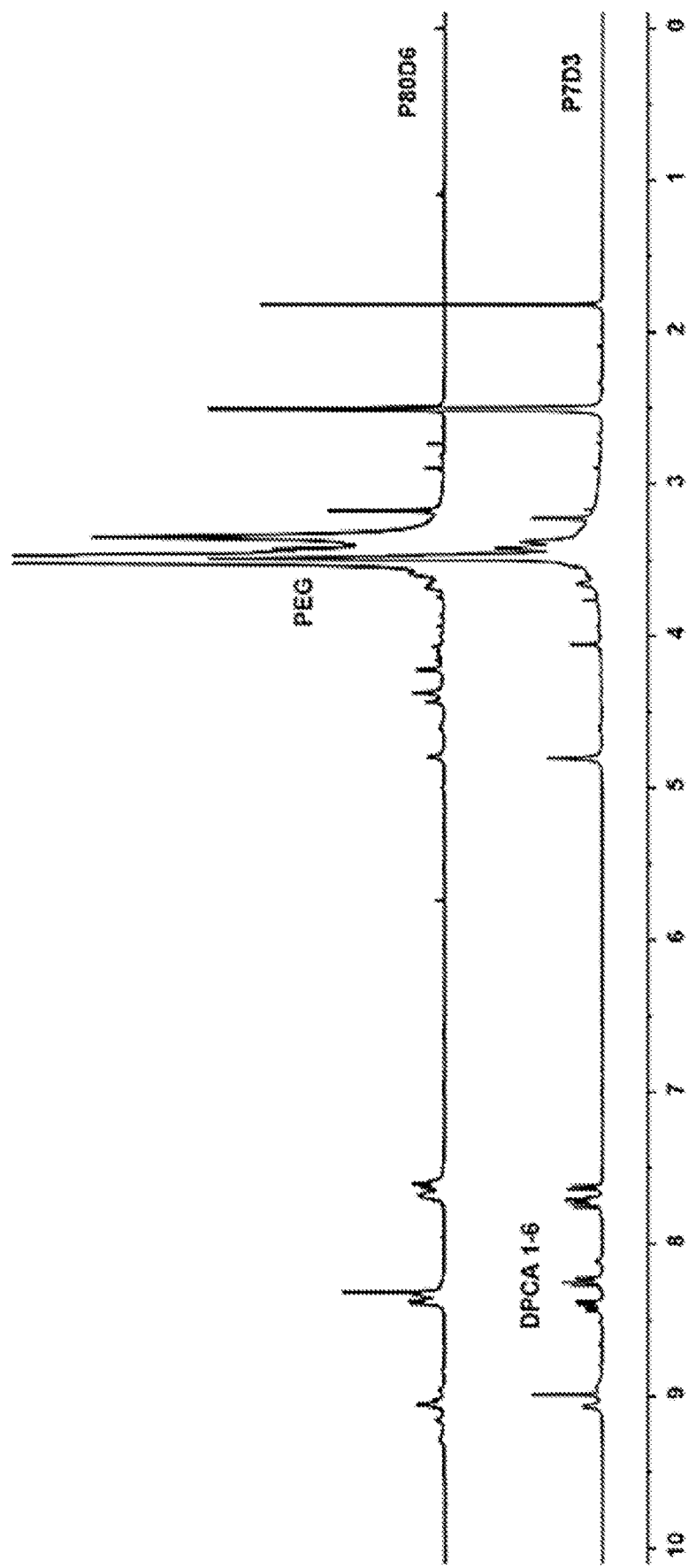

PEG or PEG-triol (6) (1 mmol) was dissolved in 30 mL DMF and NaH (60%, 1.5 eq to hydroxyl group) added. After 10 minutes, DPCA-Im (1 eq to hydroxyl group) was added and the mixture was stirred at 50° C. for 30 minutes to form a clear viscous solution. The product was precipitated in diethyl ether (with 1% acetic acid), washed with methanol/diethyl ether once, then washed with diethyl ether twice, and dried under vacuum overnight (90%, product structures shown in FIG. 1). Structure characterizations of products P7D3 and P80D6 are shown in FIGS. 3A and 3B.

Example 3—Preparation and Composition of PEG-DPCA Hydrogels 100 mg/mL of P7D3 and P80D6 solutions were mixed in different ratios (see Table 1). The mixtures were warmed to 50° C. and mixed well by vortex for 5 minutes, then cooled to room temperature to form a homogeneous hydrogel. Use of a lower molecular weight PEG (PEG4000) for the telechelic bridging polymer resulted in gelation times on the order of hours (data not shown).

Example 4—Rheological Characterization of PEG-DPCA Hydrogels

Figure 6A:
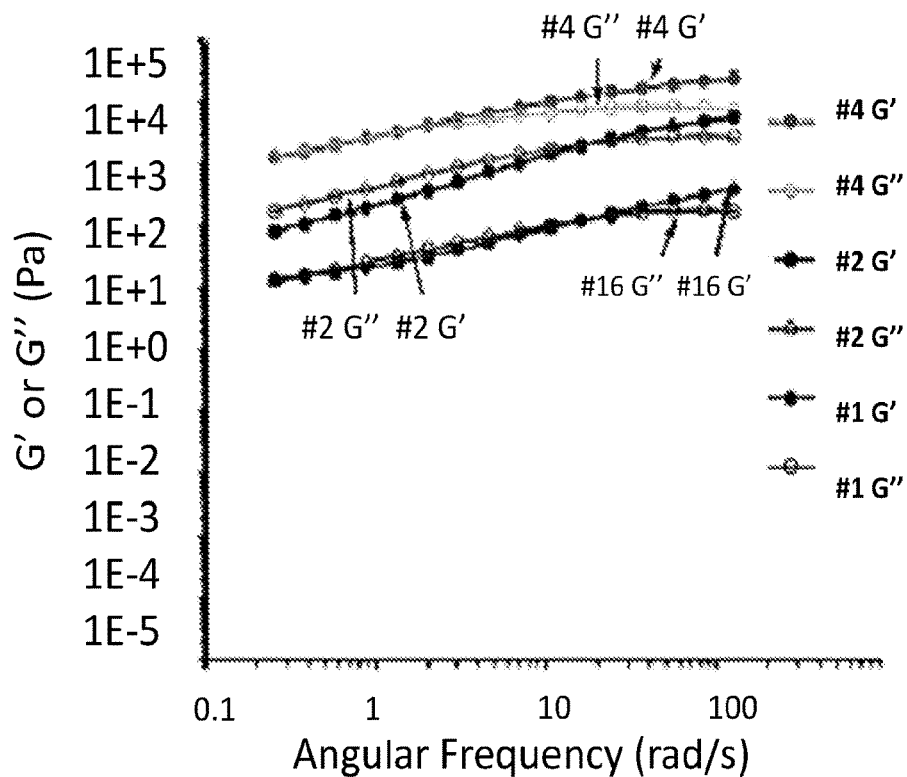
FIGS. 6A-6D: Rheological characterization of P7D3/P80D6 gels. Frequency sweep study of Mixtures #1-#17 shown in FIGS. 6A-6C, at 100 mg/ml total polymer concentration and $\gamma=1\%$, 37° C.
Figure 6B:
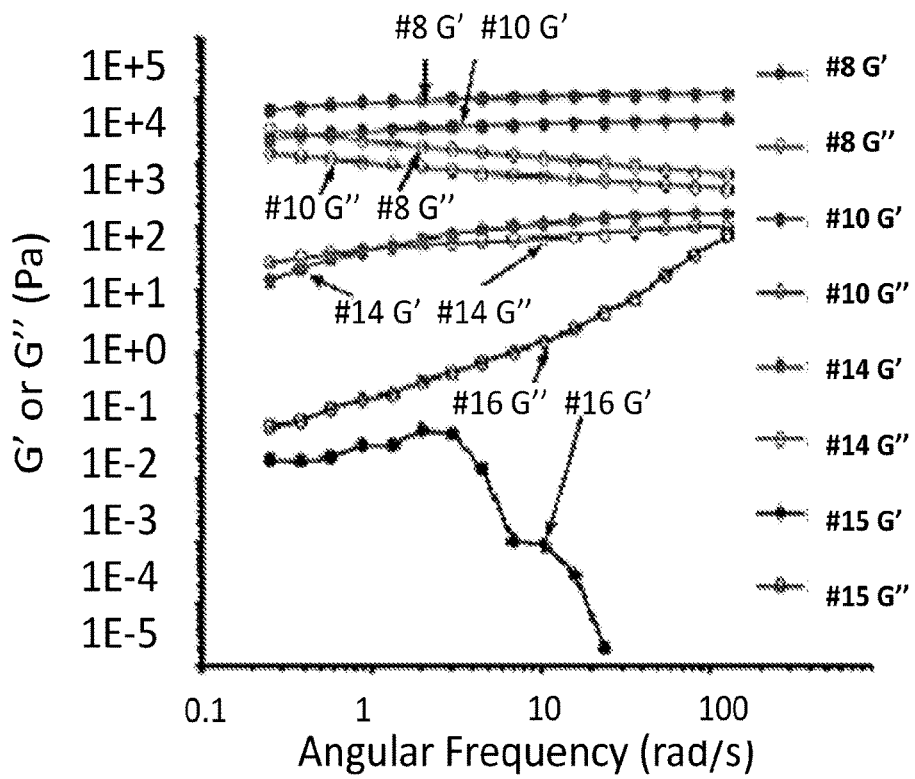
Figure 6C:
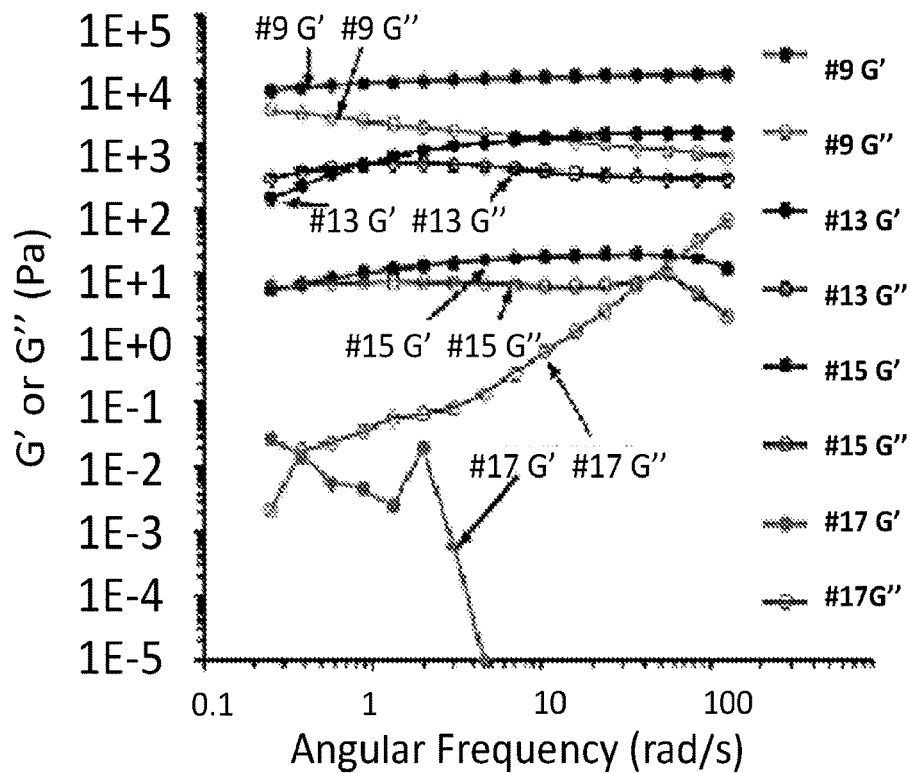
Figure 6D:
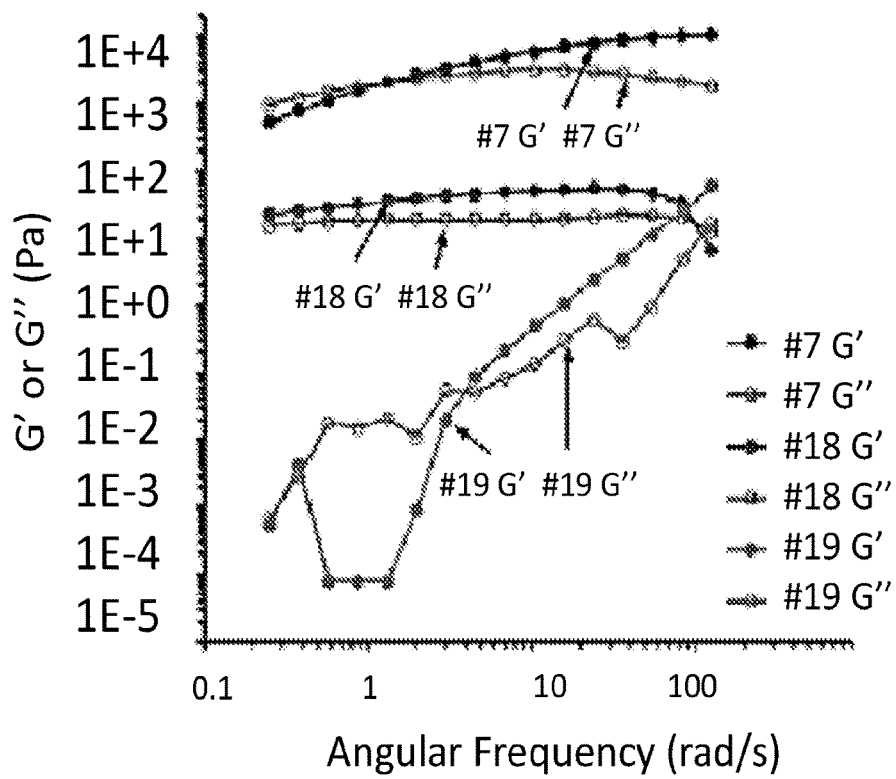

Rheological characterization was performed on an oscillatory rheometer (MCR-302 modular compact rheometer by Anton Paar) with a parallel plate geometry (25 mm diameter). Dynamic oscillatory strain amplitude sweep and step-strain behavior measurements were conducted at a frequency of 6.28 rad/s and 37° C. and 1% or 100% strain applied alternatively. Dynamic oscillatory frequency sweep measurements were conducted at 1% strain amplitude and 37° C. Dynamic temperature-dependent sweep measurements were conducted at a frequency of 6.28 rad/s and 1% strain, with 6° C./min heating and cooling rate. Rheological results of 100 mg/mL mixtures are shown in FIGS. 6A-6D, with sample ID correlating to compositions shown in Table 1. In FIG. 6D, were controls in which P80D6 or P7D3 were replaced by DPCA-free PEG, showing the importance of DPCA domains in the observed rheological behavior. Thus, Mixture #18 was a mixture of 80 mol % P7D3 and 20 mol % PEG8000, and Mixture #19 was a mixture of 80 mol % PEG750 and 20 mol % P80D6.

Example 5—Dynamic Light Scattering Characterization of PEG-DPCA Hydrogels

Figure 9A:
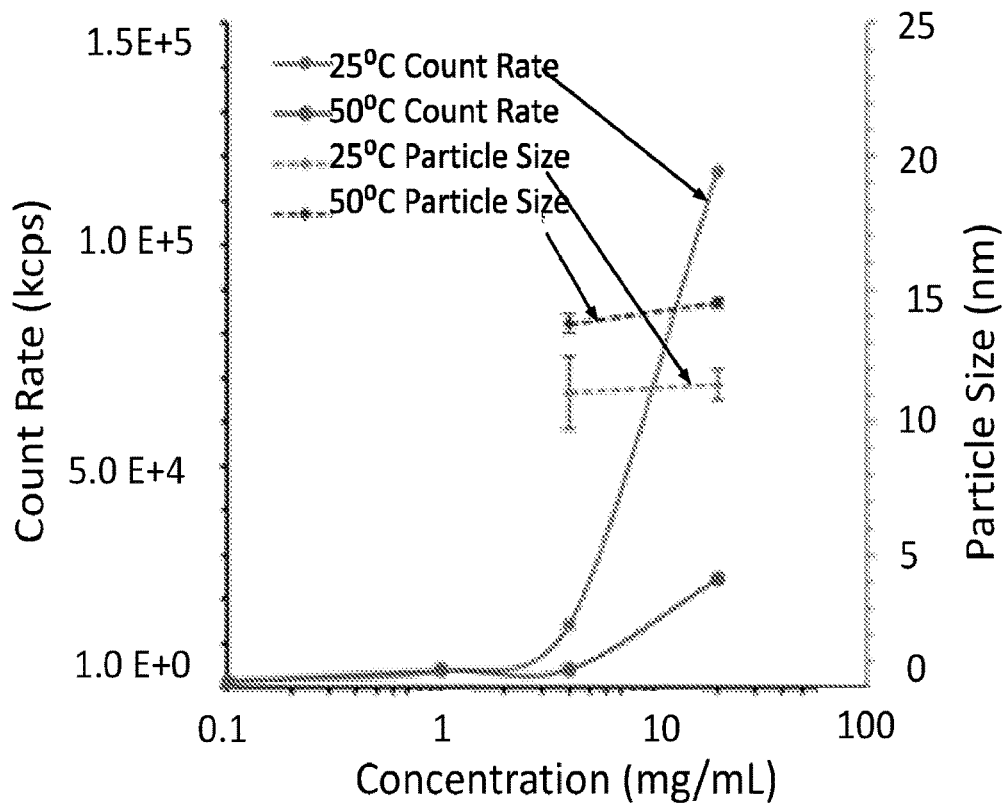
FIGS. 9A and 9B: DLS analysis of P80D6 solution.
Figure 9B:
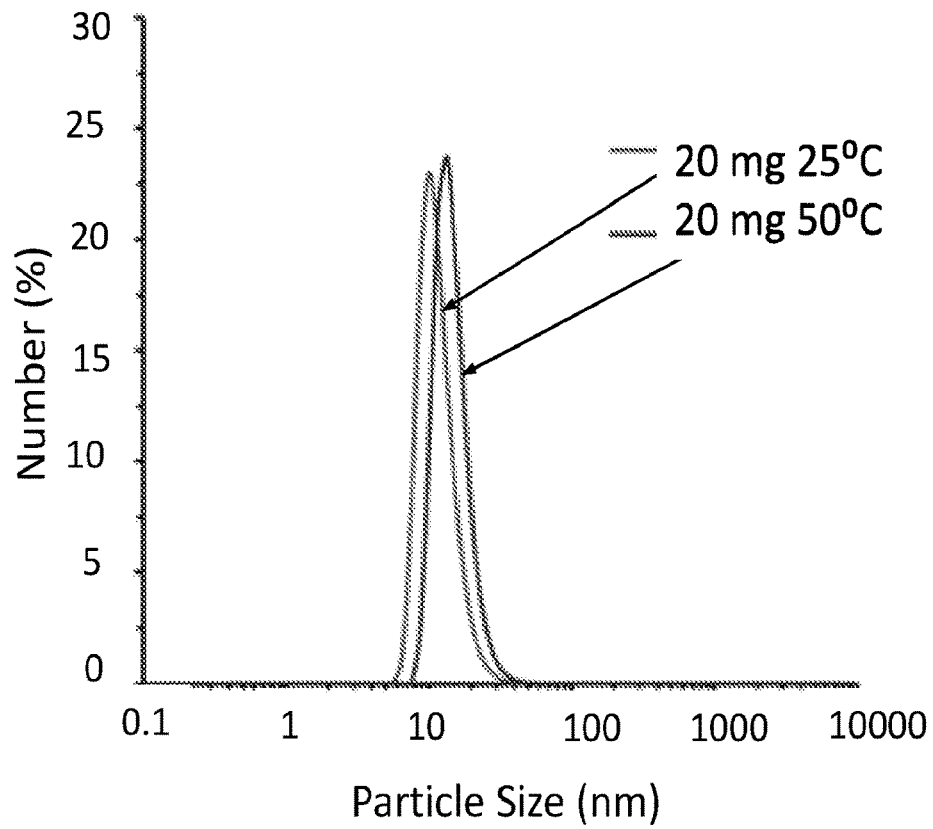

A Malvern Instruments ZetaSizer Nano ZS (zen3600) was used for dynamic light scattering (DLS) studies. Diameter and measured Count Rate were calculated from an average of three measurements. Derived Count Rates were obtained by measured count rate divided by the attenuation factor. The results are shown in FIGS. 9A and 9B.

Example 6—Electron Microscopy Characterization of PEG-DPCA Hydrogels

Figure 10B:
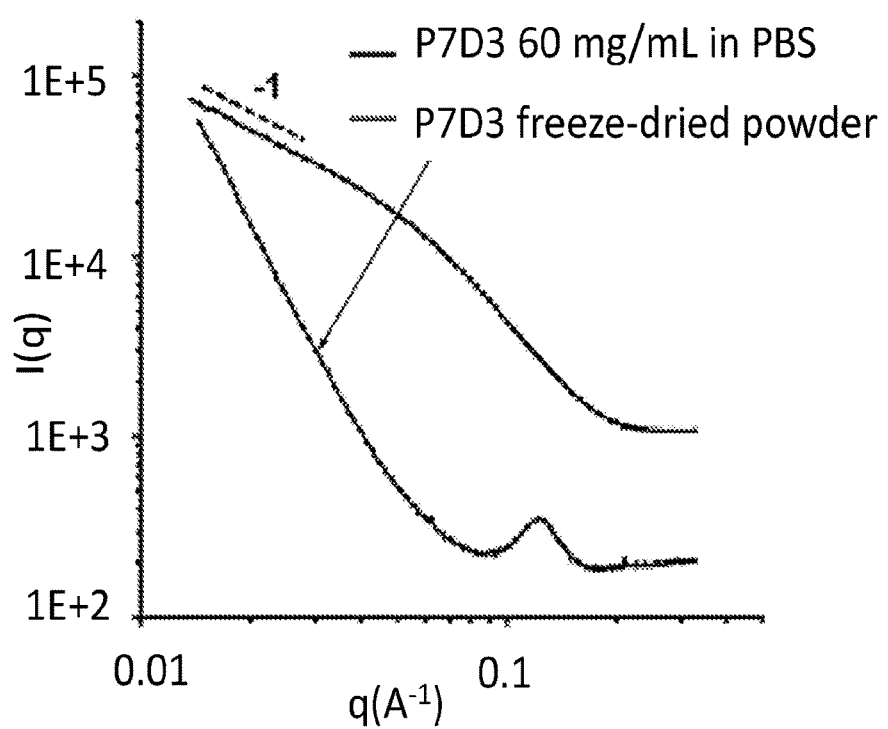
Figure 11:
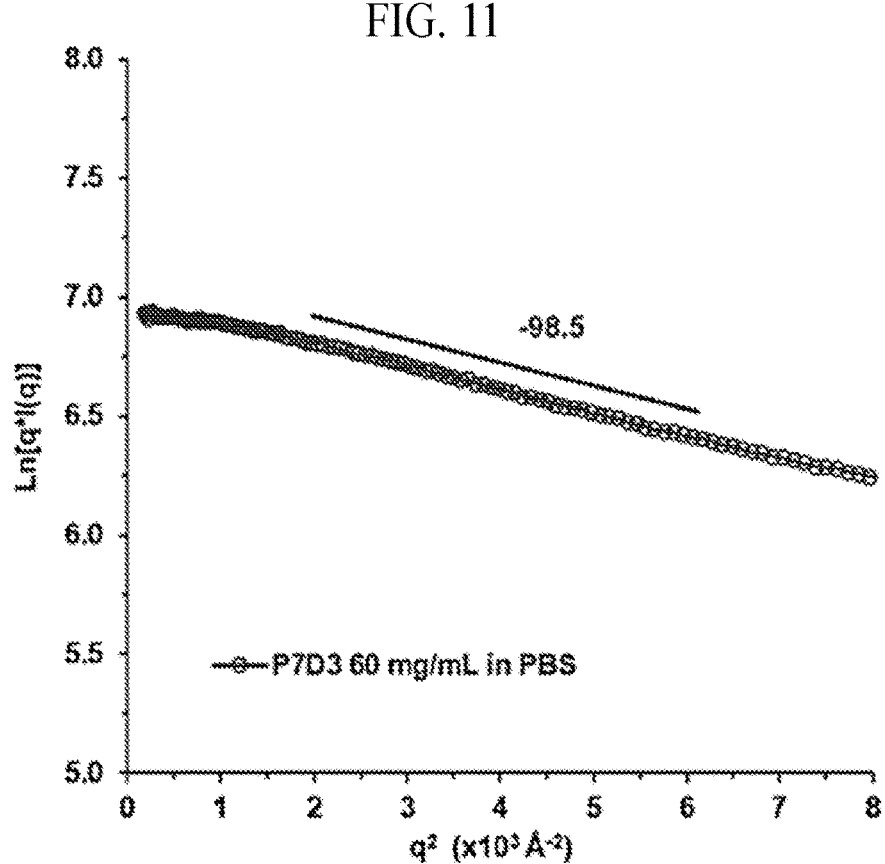
FIG. 11: Modified Guinier plot of P7D3 solution.

P7D3 nanofiber solutions were dropped on carbon coated copper grids for 2 minutes and stained for 1 minute with 0.5% uranyl acetate aqueous solution for conventional TEM. TEM Images were taken on a FEI Tecnai 12 transmission electron microscope. Samples for cryoEM were prepared by vitrifying nanofiber solutions in liquid ethane using a Gatan Cryoplunge system. CryoEM images were taken on a JEOL 3200 TEM. The results are shown in FIGS. 10A and 10B.

Example 7—Small Angle X-Ray Scattering (SAXS) of PEG-DPCA Hydrogels

Small-angle X-ray scattering (SAXS) experiments were performed on Beamline 7.3.3 of the Advanced Light Source at Lawrence Berkeley National Laboratory. The polymer solutions and hydrogels were loaded in 2.0 mm quartz capillaries and placed in a thermo-control device while acquiring data. The sample was probed at multiple locations in the capillary with a 10-keV synchrotron X-ray beam with a Mo/B4C double-multilayer monochromator. Samples were irradiated for 0.5 second. The 1D scattering profiles were obtained by radial integration of 2D-patterns with scattering from PBS buffer in the capillary subtracted as background.

Example 8—In Vitro Drug Release of PEG-DPCA Hydrogels

50 µL of Gel #12 was placed in a semipermeable membrane and suspended in 200 mL PBS buffer (pH 7.4) in a capped glass vial. The vial was placed in a shaking incubator (100 rpm, 37° C.). The buffer was replaced with fresh PBS daily. For polymer solutions, 1 mL of P7D3 or P80D6 solution (from 1 µg/mL to 100 mg/mL) were placed in 15 mL glass vials releasing DPCA in a shaking incubator (100 rpm, 37° C.). At designated time points an aliquot of buffer was removed and analyzed by HPLC with UV detection at 261 nm.

Example 9—Cytotoxicity Characterization of PEG-DPCA Hydrogels

Primary ear dermal fibroblast cells were established from MRL and B6 mice using methods known in the art. Cells from early passages (<P20) were used in the described experiments. Cells were grown at 37° C., 5% $CO_2$, and 21% $O_2$ in high glucose DMEM (with L-glutamine) supplemented with 10% v/v FBS, 20 mM HEPES and 100 IU/mL penicillin/streptomycin.

To determine cytotoxicity, B6 cells were grown overnight in 96 well cell culture plates. The cells were cultured for 24 hours in media conditioned with gel extract as follows. 10-40 µL samples of Gel #12, P7D3 (10 mg/mL), P80D6 (90 mg/mL) or PEG polymers without any DPCA group (PEG750:PEG8000=1:9 w/w, 100 mg/mL) were added directly into wells containing cells and 100 µL fresh media. Cell viability was measured by exposure to live-dead cell stain (ReadyProbes cell viability imaging kit by Life Technologies) for 15 minutes. Photomicrographs were produced using a fluorescent microscope (EVOS FL Color Imaging System) and the cell numbers were averaged from three different images.

Example 10—Immunohistochemistry of Cells Treated with PEG-DPCA Hydrogels

For immunohistochemical staining, MRL and B6 cells were seeded at 5000 cells per well in 96 well plates and grown overnight using methods in the art. Cells were subsequently treated for 24 hours with samples and controls as described above, then rinsed with PBS, fixed in cold methanol (−20° C.) for 10 minutes, rinsed with PBS, treated with 10% goat serum and 0.1% Triton-X100 for 1 hour. Then the cells were rinsed with PBS, incubated with the appropriate primary antibodies (diluted in 10% goat serum) at 5° C. overnight, rinsed with PBS, incubated with secondary antibodies (diluted in PBS) at room temperature for 1 hour (in dark), and rinsed with PBS. Before imaging, 1 drop of antifade mountant with DAPI (Molecular Probes) was added to the wells and sealed with Greiner multiwell plate sealer (Sigma-Aldrich). Photomicrographs were taken using a fluorescent microscope (EVOS FL Color Imaging System).

In FIG. 17, cells stained with stem cell or immature cell markers are shown. Here, the normal regenerative MRL cells display these markers without any induction (halos around cell nuclei). Non-regenerative B6 cells do NOT express these markers (only cell nuclei cana be seen). However, upon in vitro stimulation with DPCA/hydrogel, all of these markers are now expressed indicating a de-differentiation effect by drug (halos now appear around the cell nuclei).

Figure 20:
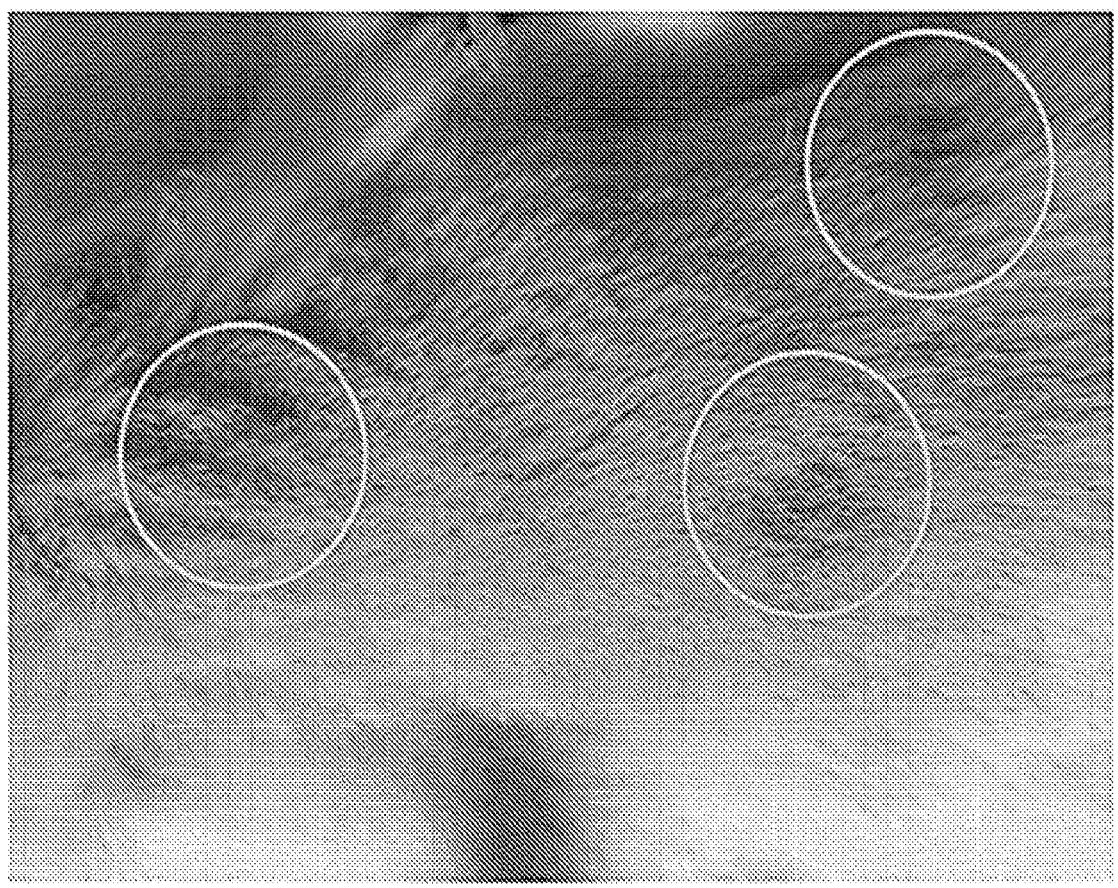
FIG. 20: Discoloration of skin at injection sites of PEG control group, indicating the formation of hematomas as confirmed by histology seen in FIG. 18A.

Example 11—In Vivo Soft Tissue Regeneration 10 weeks old female Swiss Webster mice were obtained from Charles River. On Day 0, 2.1 mm ear hole punch wounds were created in ear pinnae, and then 25 µL of Gel #10 or Gel #12 was injected subcutaneously in the back of the neck using methods in the art. The gel injection was repeated again on Day 8. At various time points, ear hole diameter was measured with calipers to monitor wound closure. Tissue from hole-punched ears and skin with underlying muscle taken from the injection site were fixed with Prefer fixative (the active ingredient is glyoxal) (Anatech) overnight and then washed in $H_2O$. Tissue was embedded in paraffin and cut into 5-µm thick sections. Tissue sections were dewaxed in xylene, rehydrated, and then stained with hematoxylin (Leica Microsystems, #3801562) and eosin (Leica Microsystems, #3801602). The stained slides were washed, rehydrated, cleared with xylene and coverslipped with Permount mounting media (Fisher, SP15-500). Staining was visualized using an Olympus (AX70) microscope in bright field for H&E using a 4× objective and a Spot camera with bounded software. In FIG. 18A, injection of DPCA/hydrogel #12 gel shows normal histology at the injection site, whereas the control PEG shows a hematoma at the injection site and is considered toxic (FIG. 18A, black arrow) (see FIG. 20), where the site of injections of the control PEG in the skin appear black. In FIG. 18B, the response curve where gel #12 shows a more rapid reduction in ear hole diameter compared to the control. In FIG. 19A, HIF-1α expression seen as green fluorescence (grey arrows) is stabilized as early as day 1 and is still expressed on day 7. In FIG. 19B, we now used the DPCA/hydrogel #10 and gave only 2 injections. Here, we see a bigger effect than gel #12 in FIG. 18B. In FIG. 19C, the ears from mice given drug (lower panel) show an ear that is almost closed and an ear that is completely closed (black arrow pointing to where hole was) compared to the ears' holes given the control by day 34. In FIG. 19D, day 34 histological sections of the ears can be seen. Cartilage growth occurs in three months (areas between the black lines) so is not seen here but does occur. New hair follicles are seen in the new growth area (grey arrows).

Example 12—In Vivo Periodontal Bone Regeneration 22-month-old female B6 mice (75% survival rate at this age) were obtained from the National Institute of Health (NIH) and examined by microCT for bone degeneration of the jaws. The bone of 22-month old mice was thin and mottled with a "moth-eaten" appearance. The bone crest margin around teeth had significantly receded and there were deep cracked bone fissures.

The mice were treated with Mixture #10 (or Mixture #12, see Table 1) or PBS (control) on Day 0 and Day 8. The mice were microCT scanned at 1) approximately 20 days after initial drug injection; 2) at 2 months after initial drug injection; and 3) at 4 months after initial injection. A significant healing effect was observed in mice treated with PEG-DPCA hydrogel at 2- and 4-months post-injection and no healing effect was observed in the control animals. All degenerative parameters showed improvement.

Figure 21A:
FIGS. 21A and 21B: Micro-CT images of jaws of control (PBS vehicle; no 1,4-DPCA) mouse.
Figure 21A:
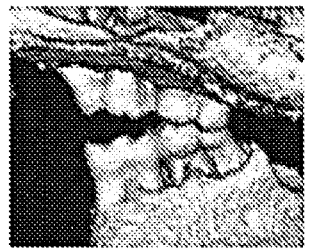
Figure 21B:
Figure 21B:
Figure 22A:
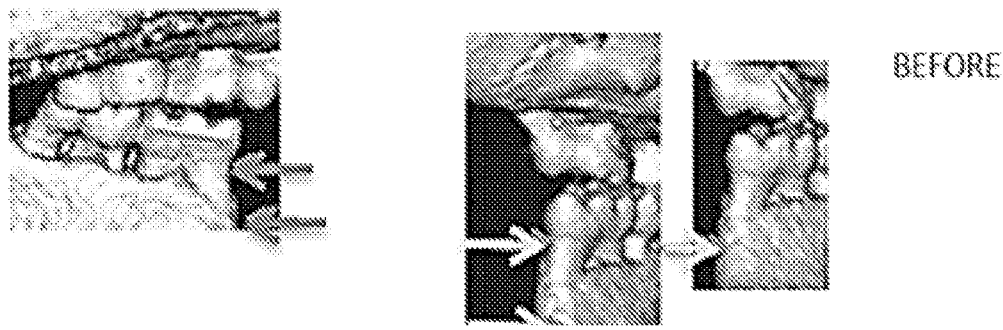
FIGS. 22A and 22B: Micro-CT images of jaws of hydrogel treated mouse.
Figure 22B:
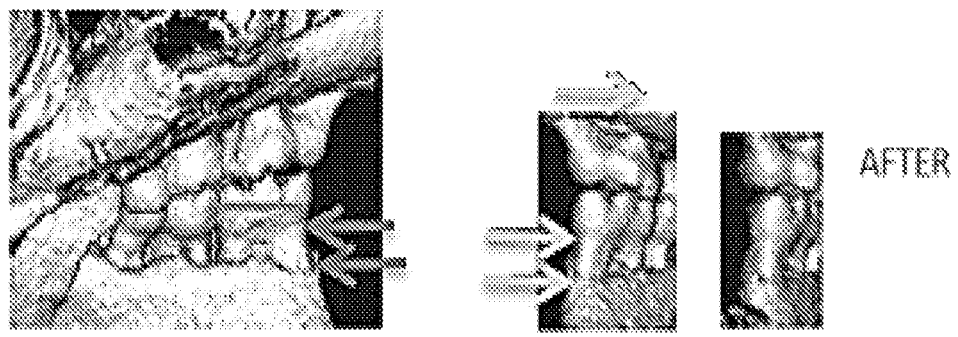

For example, in control mouse C0, we saw a degenerative response with bone loss (from crown to bone margin=0.8 mm) over this time period (FIG. 21B). However, in aged mouse B4, a drug-injected C57BL/6 mouse, two and four months after drug administration we saw bone growth (from crown to bone margin=0.4 mm) which halved the bone loss (FIG. 22B). This degree of bone recovery is significant. Furthermore, there is a general recovery of bone density and definition. From the front view (crown to bone=1.1 mm) before drug and then, 2-4 months after drug (crown to bone=0.5 mm), the treatment more than halved the bone loss. It should also be noted that there initially is a deep bone crevice which completely fills in with bone in response to drug.

Note also that mouse B4 showed ear hole closure (from 2.1 mm to 0.5 and 0.1 mm ear hole diameter) in response to drug, whereas control mouse C0 showed only 1 mm of closure, which is normally seen in non-drug-treated mice. Ear hole closure is considered the gold-standard in mouse regenerative healing.

Figure 23A:
FIGS. 23A and 23B: Periodontal Changes shown by MicroCT analysis of the jaw of an untreated (FIG. 23A) and treated (FIG. 23B) female mouse.
Figure 23A:
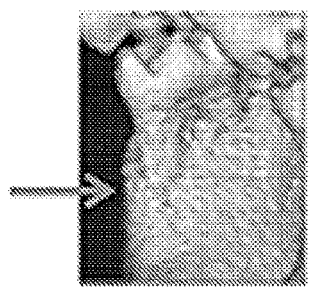
Figure 23B:
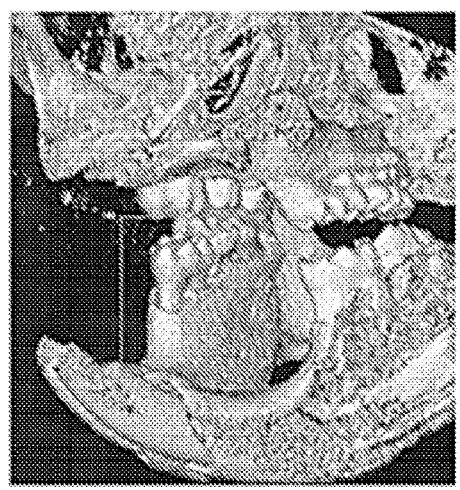
Figure 23B:
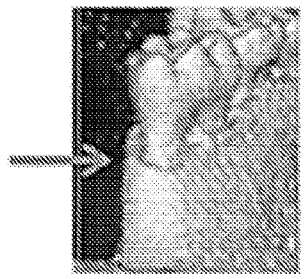

As shown in FIGS. 23A and 23B, microCT analysis revealed the extent of regeneration of the bones in the jaw structure upon treatment. Examination of the jaw of a 24 month old mouse revealed cracked and mottled bone and loss of bone around the teeth. Upon introduction of the PEG-DPCA (25 microliters of mixture #10 (see Table 1), given twice on day 0 and day 8 subcutaneously in upper flank back skin), the jaws regrew bone around the tooth and healed the cracks in the bone.

Figure 24A:
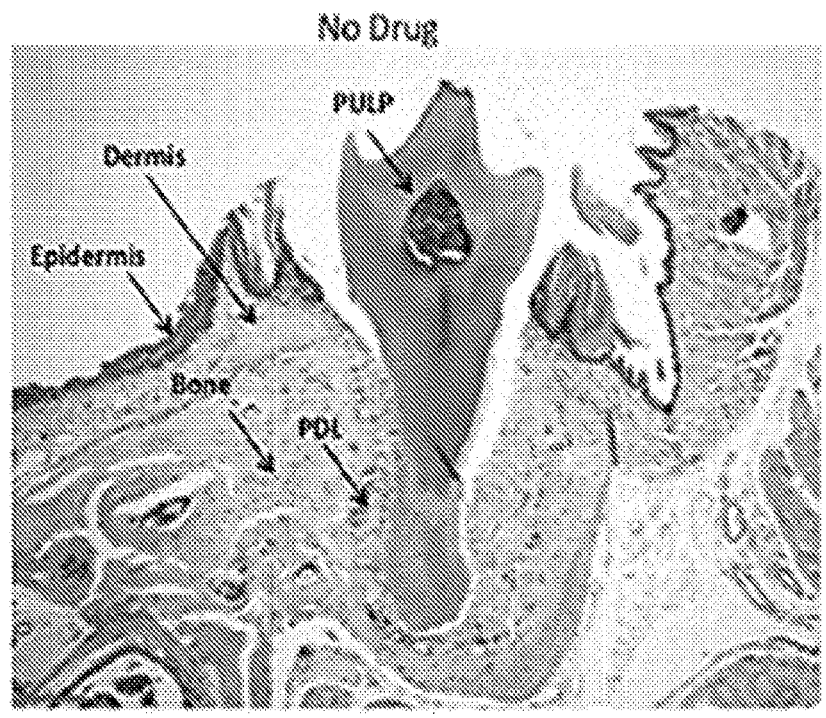
FIGS. 24A-24F: Jaw tissue stained with hematoxylin and eosin control (FIGS. 24A-24C) and given drug (FIGS. 24D and 24F) to examine changes in epidermis, dermis, tooth pulp, and periodontal ligament(PDL) which secures the tooth into the bone cavity.
Figure 24B:
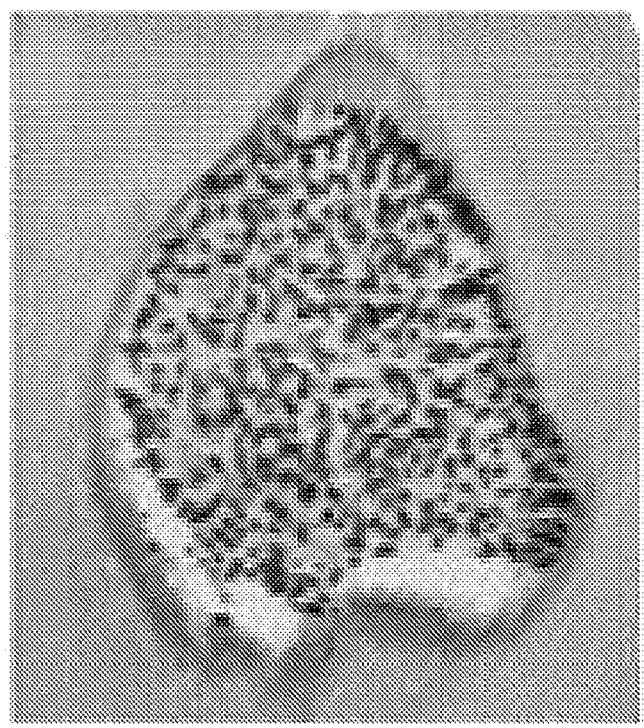
Figure 24C:
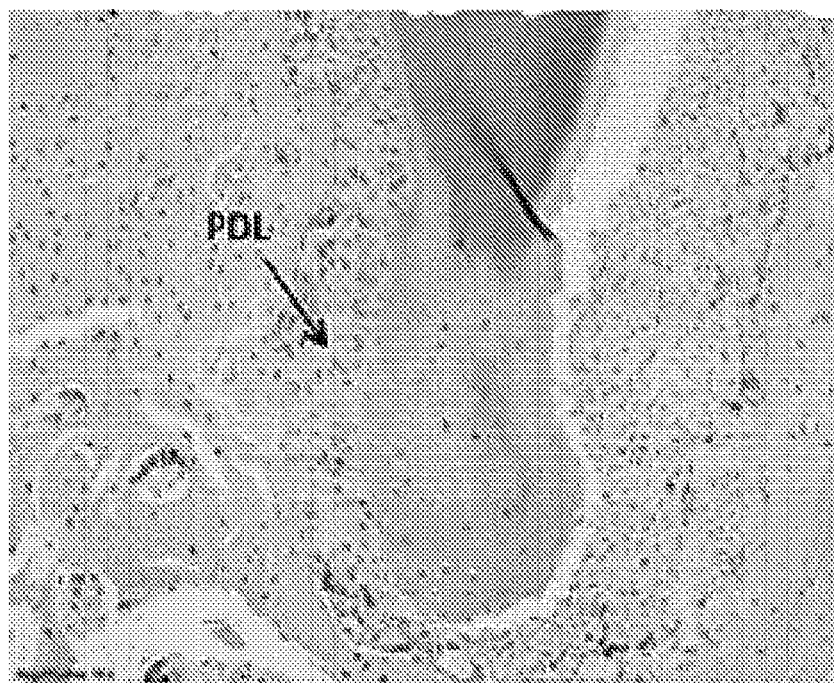
Figure 24D:
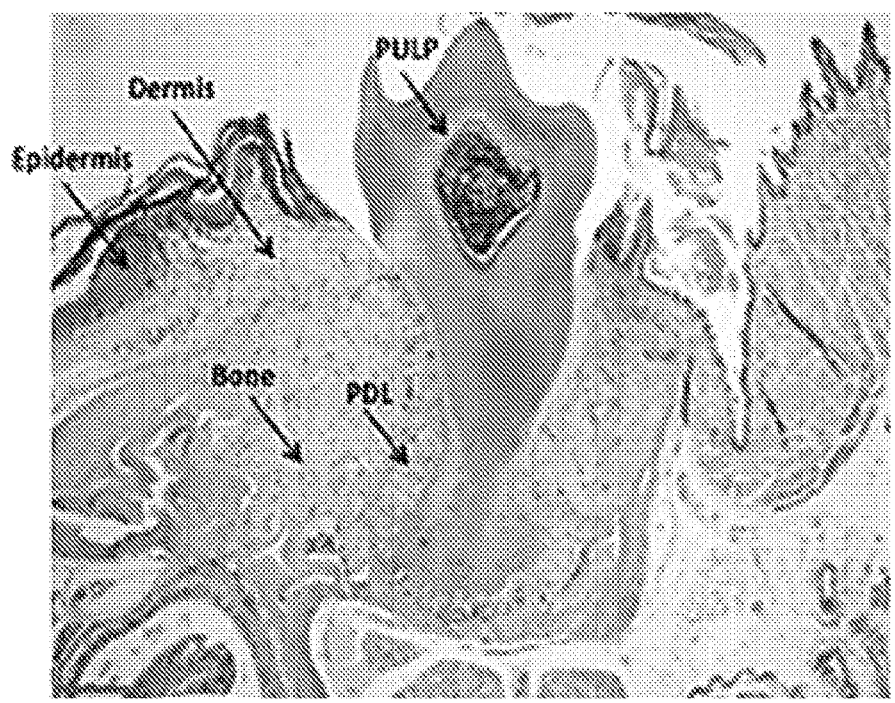
Figure 24E:
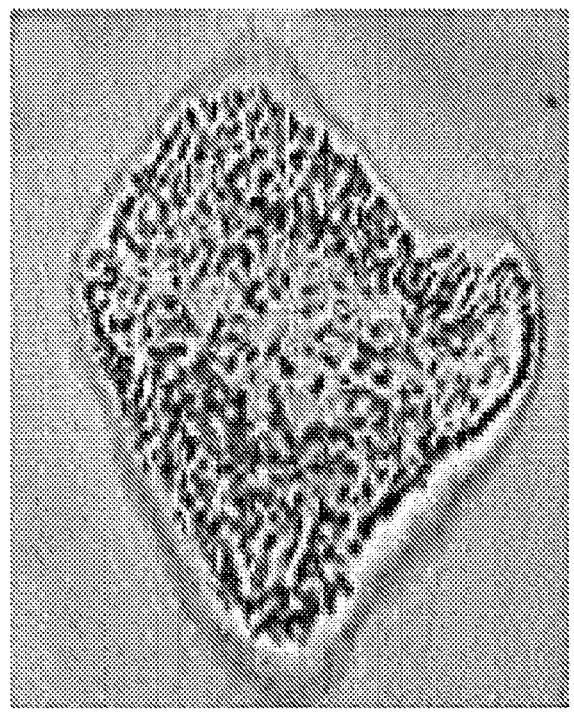
Figure 24F:
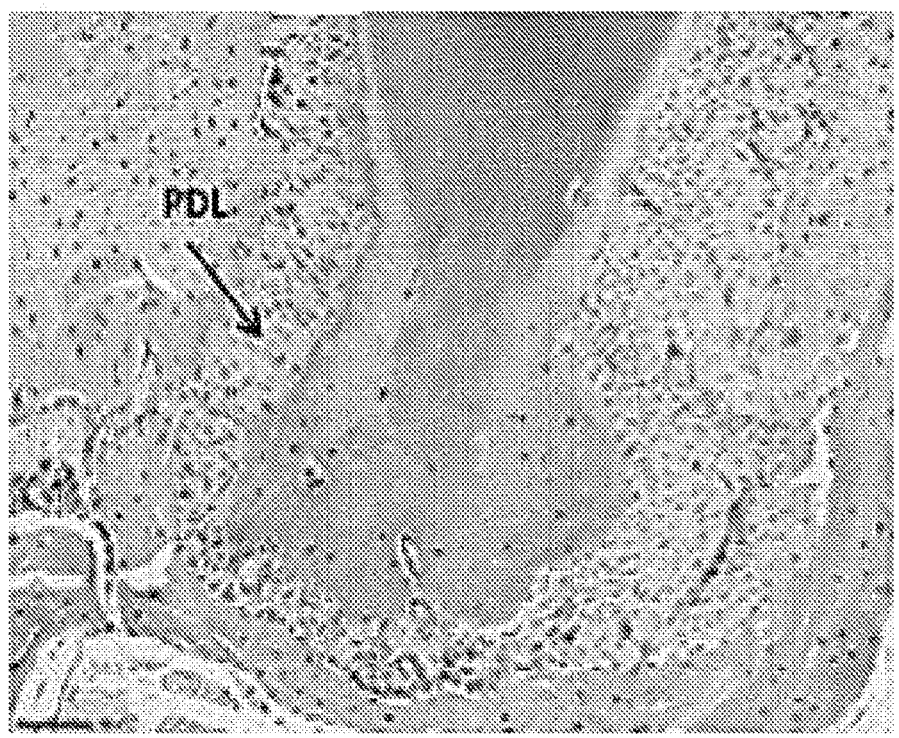

Periodontal disease leads to breakdown not only of jaw bone but also the periodontal ligament (DDL) which hold the tooth attached to the bone. Under normal circumstances, the PDL degenerates from regular chewing. Treatment of non-regenerating Swiss Webster female mice with PEG-DPCA (25 microliters of mixture #10 (see Table 1) administered subcutaneously in the upper flank back skin) for 15 days shows extreme differences between treated and untreated PDL (FIGS. 24A-24F and Table 2). In FIG. 24, a thicker epidermis and dermis, bone growth, PDL thickness, and PULP differences are seen after treatment with the PEG-DPCA (FIG. 24D-24F) compared to untreated jaws (FIG. 24A-24C). An analysis of changes in PDL showed a two fold increase in the treated animals and analysis of the PULP blood vessels showed a 5 fold increase in the treated mice.

TABLE 2

Changes in PDL and PULP after drug treatment

| PDL | Cells/area | Cells/area as normalized to Kpixels |
|---|---|---|
| Control | 0.015126722 | 15.1267216 |
| Treated | 0.028887396 | 28.887396 |

| Pulp | Blood vessels/ pulp area | Vessel/Pulp area as normalized to Kpixels |
|---|---|---|
| Control | 0.025764691 | 25.7649095 |
| Treated | 0.169421429 | 169.4214287 |

Figure 25A:
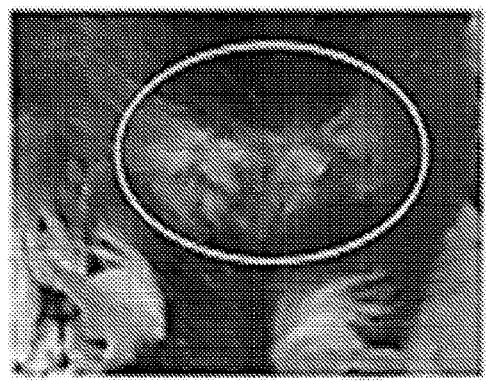
FIGS. 25A-25C. Rapid healing and skin closure (9 days) of a large skin wound after treatment.
Figure 25B:
Figure 25C:
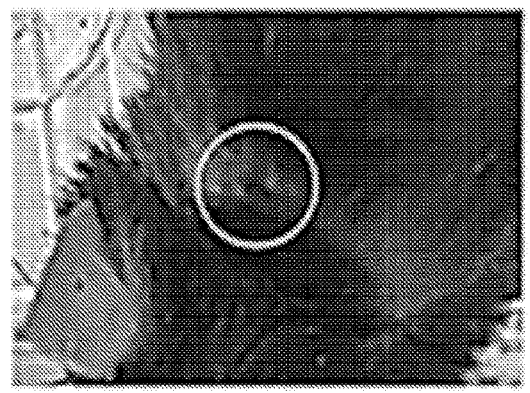

Example 13: In Vivo Wound Healing of Chronic Wounds by Topical Administration of 1,4, DPCA In FIG. 25A, a B6 female mouse, 31.5 months old, developed a large skin wound on the back of the neck. One dose of gel mixture #12 (see Table 1) was applied topically to the surface wound (50 ul) and within 3 days, the wound edges came together and by day 9 near complete healing was seen. About one week later, hair started to fill in. This is in contrast to a small wound in adult mice where the wound closes at about 10 days or more and then further healing of the margins takes about 5-10 days more. These wounds get infected and do not heal and essentially become chronic wounds, leading to the death of the mouse.

Figure 26A:
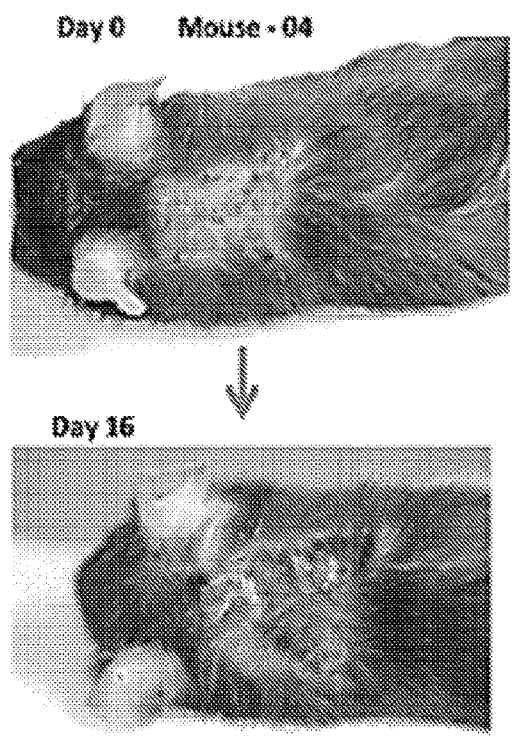
FIGS. 26A and 26B. Chronic skin ulcer healing and hair growth after treatment.
Figure 26B:
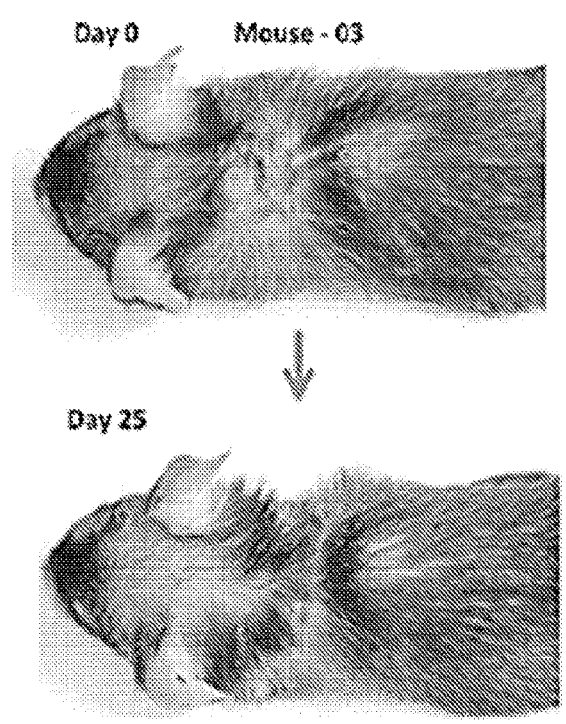

FIGS. 26A and 26B show two other examples in which mice develop very large wounds spontaneously as they age. The mice were given 50 ul of gel mixture #12 (see Table 1) once on day 0 and once on day 8 and applied topically. Hair growth here was seen on a bed of tissue which had healed without skin contraction but with new epidermal and dermal growth and with new hair growth (suggesting a lack of scar tissue) that grew back not as grey hair but as black hair. The results show that the gel mixture #14 (see Table 1), which is in a liquid state, is easier to apply and almost forms a type of liquid bandage and leads to excellent healing.

Example 14: Peripheral Nerve Growth Induced by 1,4-DPCA Hydrogel

Nerve regeneration is a prerequisite for limb regeneration to proceed in the amphibian and in the MRL mouse, it has been shown that denervation of the ear blocks ear hole closure and that the MRL mouse shows increased numbers of nerve fibers compared to B6 at days 15-30 of regenerative healing.

Figure 27A:
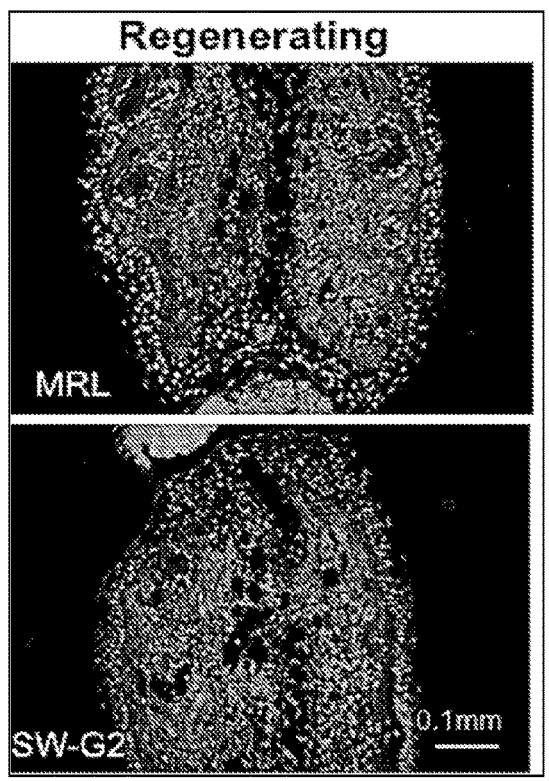
FIGS. 27A and 27B. Peripheral Nerve Growth after ear hole injury induced by PEG-DPCA hydrogel.
Figure 27B:
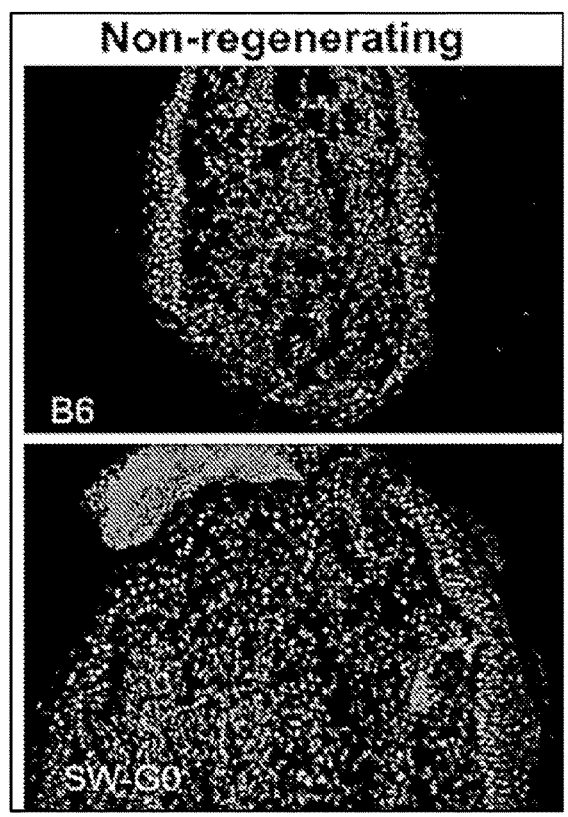

We examined nerve growth in the regenerative MRL mouse ear that was hole punched prior to the accumulation of immature cells but after full re-epithelialization occurred (Day 3 post injury). As seen in FIGS. 27A and 27B, by day 3 post ear punch, nerve growth is significant in the MRL regenerator (white arrows, cloudy area in tissue) but not in the B6 non-regenerator.

We then examined the effect of the drug on a non-regenerator mouse. Mouse ears, 3 days post-ear punch injury, were stained with antibody to neurofilament (white arrows SW-G2, FIGS. 27A and 27B) and nerve fibers (cloudy area) can be seen in the regenerating ear holes as seen in MRL and as seen in SW (G2) that were given PEG-DPCA hydrogel (mixture #12 (see Table 1) 25 ul). New fibers were not observed in non-regenerating ear holes (FIGS. 27A and 27B) of B6 and SW(G0) that were given only PEG (no DPCA). Staining is also seen in epithelial cells at the edge of the tissue and may be a cross-reaction between intermediate filaments neurofilaments vs keratin. The white dots staining shown in FIGS. 27A and 27B is DAPI, a nuclear stain.

Swiss Webster (SW) non-regenerator ears were either untreated (G0) or treated with PEG-DPCA hydrogel (mixture 12) (G2) on day 3 post ear punch injury. Following administration of the PEG-DPCA hydrogel, the SW ears (G2) show significant MRL-like nerve growth (cloudy white) not seen in control-treated SWs (G0).

Example 15: Osteoporosis

Figure 28:
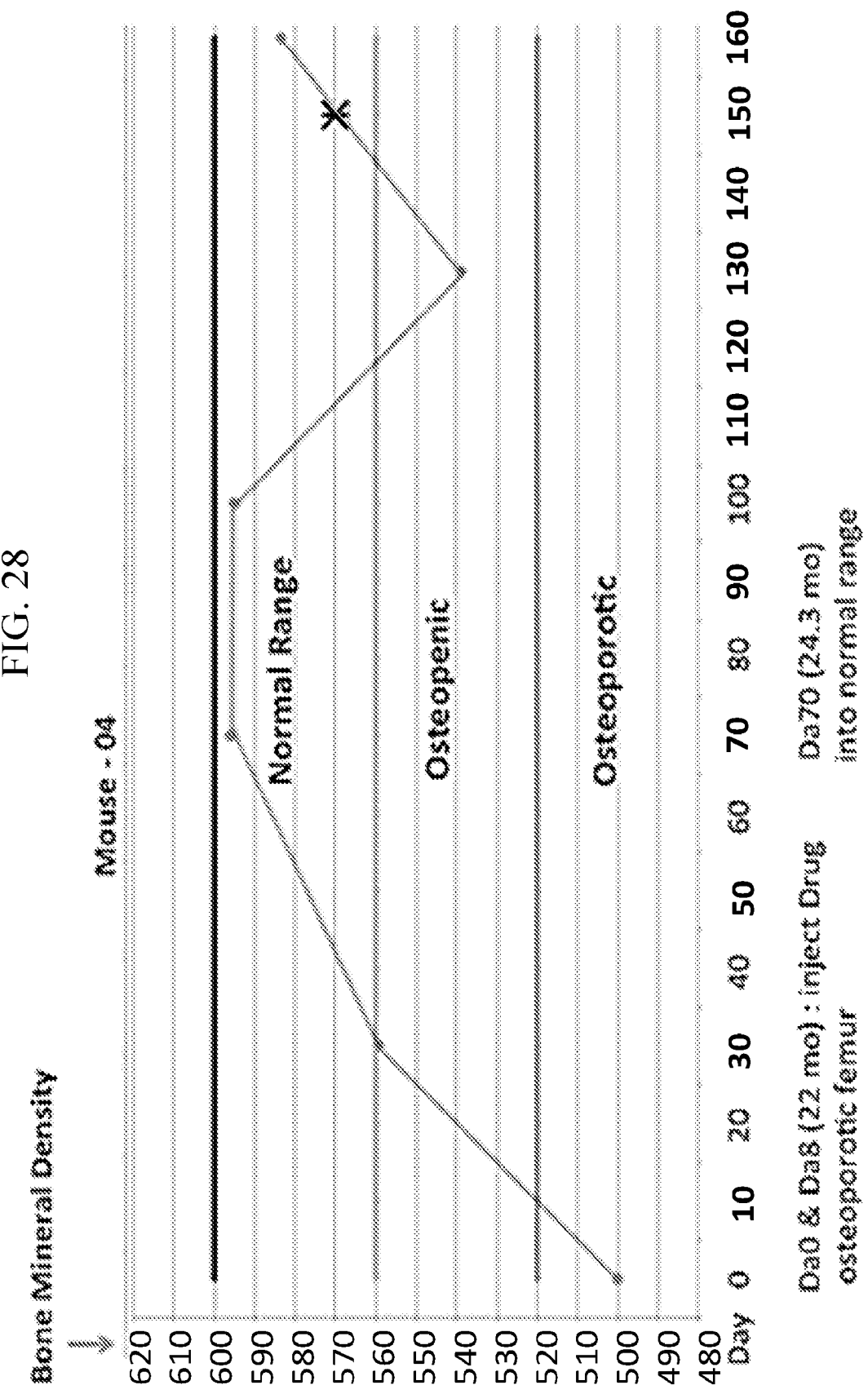
FIG. 28. Reversal of Osteoporosis by treatment with PEG-DPCA hydrogel on day 0 and day 8.

Osteoporosis is a disease in which the density and quality of the bone are reduced. This happens when bone becomes porous and fragile. We examined the effect of our drug on bone density. Female C57BL/6 mice from the National Institutes of Aging were obtained at 22 months of age. MicroCT analysis was carried out on their femurs and examined for bone density (how). There was one animal that was osteoporotic and this animal was injected with 50 ul of mixture #10 (see Table 1) subcutaneously in the upper flank back skin once on day 0 and once on day 8. As shown in FIG. 28, by day 30, bone density increased and was at the normal/osteopenic border. By day 70, this mouse was at a high normal level. By day 100, the bone density level started to go down again.

This mouse subsequently developed a skin lesion and was treated with 2 doses of mixture #10 topically, and the bone density level quickly came back to normal and has stayed there until the present time, from 25 to 34 months without any further treatment.

Example 16: Kidney Fibrosis

Using a CCL4 (carbon tetrachloride) model of fibrosis and tissue injury, we examined the effect of the drug on the elimination of preformed fibrosis. Mice were treated for two weeks with CCL4 intraperitoneally. At that time, the mice were either treated with Peg-DPCA #10 or PBS subcutaneously. Mice were euthanized and their tissue was analyzed histologically.

Figure 29:
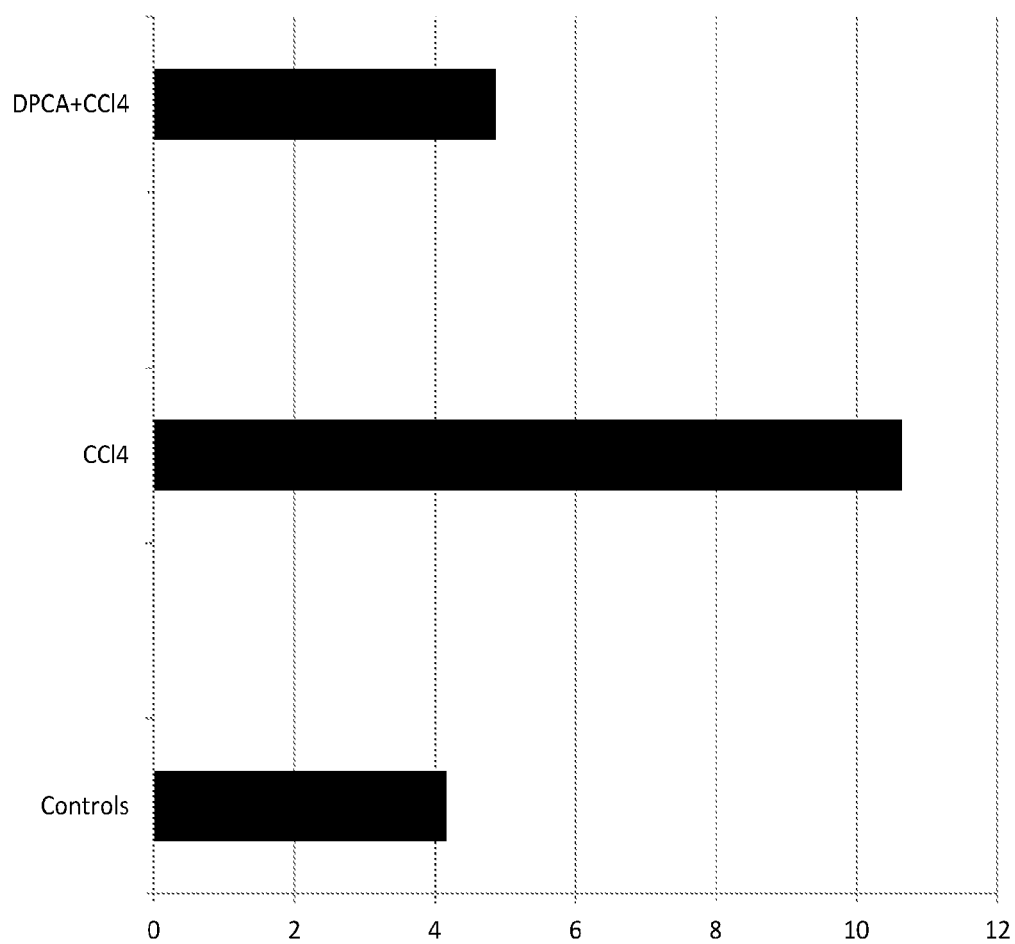
FIG. 29 Elimination of preformed fibrosis by treatment with PEG-DPCA hydrogel.

As seen in FIG. 29, in the controls, the liver did not show fibrosis and require longer CCL4 treatment. However, the kidney in the control animals did show significant fibrosis. Treatment with 25 ul of mixture #10 (see Table 1) in 2 doses, day 0 and day 8 administered subcutaneously in the upper flank back skin, showed that the level of fibrosis was at nearly the level of the normal kidney in this strain of mice, Swiss Webster female mice 12 weeks of age (2-3 mice/group). Fibrosis was measured as % fibrosis (horizontal axis) in any given area of kidney tissue.

Example 17: Vascular Response

Previous ear punch studies in regenerative MRL mice showed that endothelial precursors (CD31-positive cells) filled the ear pinna 4-7 days post injury not seen in non-regenerative C57Bl/6 mouse ears (FIG. 30A).

Furthermore, chimeric MRL mice with labeled bone marrow proved that these CD31 positive cells were derived from the bone marrow and in the MRL ear became mature blood vessels. This is known as vasculogenesis where new blood vessels are made in the regenerative mouse from a different source of cells. This is unlike the non-regenerative mice where blood vessels are made from sprouting of pre-existing vessels at the injury site (FIG. 30B).

Using the PEG-DPCA hydrogels provided herein, we demonstrated that vasculogenesis occurs when PEG-DPCA hydrogel is administered to a non-regenerative Swiss Webster mouse.

Figure 30C:
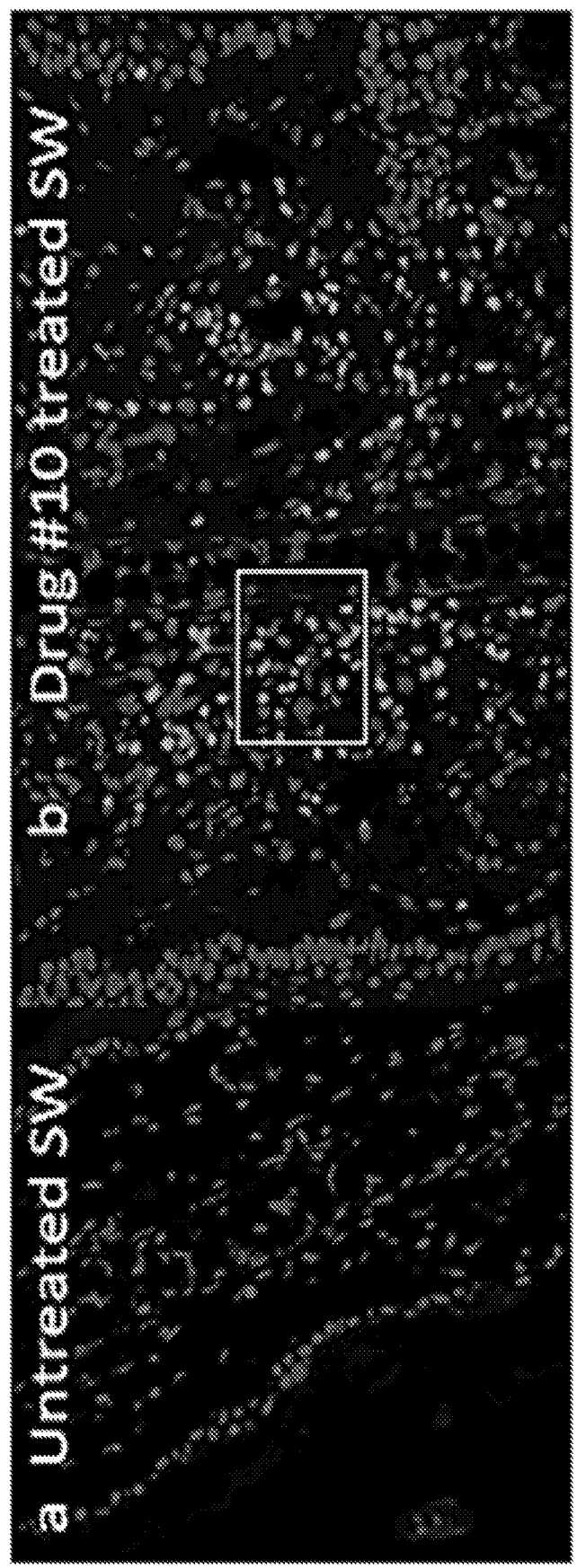

FIG. 30C shows enhanced neovascularization and vasculogenesis in regenerating ear holes in animals treated with 25 ul mixture #10 subcutaneously in the upper flank back skin. Non-regenerative female Swiss Webster (SW) mice were treated with PEG-DPCA #10 mixture and ear punch inquiries were made. At 7 days post drug and injury, untreated SW ears (FIG. 30CA showed no CD31+ infiltrating cells (endothelial or blood vessel precursors; white dots), whereas ears of treated SW mice (FIG. 30CB) showed an abundance of white CD31+ infiltrating cells (white dots) indicating the presence of endothelial or blood vessels precursors Swiss Webster female bone marrow chimeras were generated where the donor bone marrow was stained with CFSE and the recipient SW females were x-irradiated and injected with bone marrow. Examination of the ears 7 days after ear punching and administration of mixture #10 showed that there were blood vessels of bone marrow origin with endothelial precursors present indicating that from the bone marrow there are both mature blood vessels as well as nascent CD31+ blood vessels (data not shown). These results indicate that vasculogenesis is occurring whereas this is not seen in the animals not given the drug.

REFERENCES

1. Aida T, Meijer E W, Stupp S I. Functional Supramolecular Polymers. Science 2012, 335(6070): 813-817.
2. Liu K, Kang Y T, Wang Z Q, Zhang X. 25th Anniversary Article: Reversible and Adaptive Functional Supramolecular Materials: "Noncovalent Interaction" Matters. Advanced Materials 2013, 25(39): 5530-5548.
3. Boekhoven J, Stupp S I. 25th Anniversary Article: Supramolecular Materials for Regenerative Medicine. Advanced Materials 2014, 26(11): 1642-1659.
4. Goor O J G M, Hendrikse S I S, Dankers P Y W, Meijer E W. From supramolecular polymers to multi-component biomaterials. Chemical Society Reviews 2017, 46(21): 6621-6637.
5. Slaughter B V, Khurshid S S, Fisher O Z, Khademhosseini A, Peppas N A. Hydrogels in Regenerative Medicine. Advanced Materials 2009, 21(32-33): 3307-3329.
6. Cheetham A G, Chakroun R W, Ma W, Cui H. Self-assembling prodrugs. Chemical Society Reviews 2017, 46(21): 6638-6663.
7. Vemula P K, Wiradharma N, Ankrum J A, Miranda O R, John G, Karp J M. Prodrugs as self-assembled hydrogels: a new paradigm for biomaterials. Current Opinion in Biotechnology 2013, 24(6): 1174-1182.
8. Webber M J, Langer R. Drug delivery by supramolecular design. Chemical Society Reviews 2017, 46(21): 6600-6620.
9. Zhang Y, Strehin I, Bedelbaeva K, Gourevitch D, Clark L, Leferovich J, et al. Drug-induced regeneration in adult mice. Science Translational Medicine 2015, 7(290).
10. Fan F, He Z, Kong L L, Chen Q, Yuan Q, Zhang S, et al. Pharmacological targeting of kinases MST1 and MST2 augments tissue repair and regeneration. Sci Transl Med 2016, 8(352): 352ra108.

11. Clark L D, Clark R K, Heber-Katz E. A new murine model for mammalian wound repair and regeneration. Clinical immunology and immunopathology 1998, 88(1): 35-45.
12. McBrearty B A, Clark L D, Zhang X M, Blankenhorn E P, Heber-Katze E. Genetic analysis of a mammalian wound-healing trait. Proceedings of the National Academy of Sciences of the United States of America 1998, 95(20): 11792-11797.
13. Leferovich J M, Bedelbaeva K, Samulewicz S, Zhang X M, Zwas D, Lankford E B, et al. Heart regeneration in adult MRL mice. Proceedings of the National Academy of Sciences of the United States of America 2001, 98(17): 9830-9835.
14. Bedelbaeva K, Snyder A, Gourevitch D, Clark L, Zhang X M, Leferovich J, et al. Lack of p21 expression links cell cycle control and appendage regeneration in mice. Proceedings of the National Academy of Sciences of the U.S. Pat. No. 2,010,107(13): 5845-5850.
15. Latona J, Shah A, Cheng J, Messersmith P, Heber-Katz E. Enhanced Liver Regeneration After Partial Hepatectomy in Mice Treated with a Prolyl Hydroxylase Inhibitor. American Journal of Transplantation 2017, 17: 462-462.
16. Semenza G L. HIF-1 and mechanisms of hypoxia sensing. Current Opinion in Cell Biology 2001, 13(2): 167-171.
17. Banerji B, Conejo-Garcia A, McNeill L A, McDonough M A, Buck M R G, Hewitson K S, et al. The inhibition of factor inhibiting hypoxia-inducible factor (FIH) by [small beta]-oxocarboxylic acids. Chemical Communications 2005(43): 5438-5440.
18. Liao D, Johnson R S. Hypoxia: A key regulator of angiogenesis in cancer. Cancer and Metastasis Reviews 2007, 26(2): 281-290.
19. Bruick R K, McKnight S L. A Conserved Family of Prolyl-4-Hydroxylases That Modify HIF. Science 2001.
20. Kim I, Mogford J E, Witschi C, Nafissi M, Mustoe T A. Inhibition of prolyl 4-hydroxylase reduces scar hypertrophy in a rabbit model of cutaneous scarring. Wound Repair and Regeneration 2003, 11(5): 368-372.
21. Hill P, Shukla D, Tran M G B, Aragones J, Cook H T, Carmeliet P, et al. Inhibition of hypoxia inducible factor hydroxylases protects against renal ischemia-reperfusion injury. Journal of the American Society of Nephrology 2008, 19(1): 39-46.
22. Love R J, Jones K S. Transient inhibition of connective tissue infiltration and collagen deposition into porous poly(lactic-co-glycolic acid) discs. Journal of Biomedical Materials Research Part A 2013, 101(12): 3599-3606.
23. Alejandro P, Constantinescu F. A Review of Osteoporosis in the Older Adult. Clinics in geriatric medicine 2017, 33(1): 27-40.
24. Jilka R L, O'Brien C A. The Role of Osteocytes in Age-Related Bone Loss. Current Osteoporosis Reports 2016, 14(1): 16-25.
25. Chan G K, Duque G. Age-related bone loss: Old bone, new facts. Gerontology 2002, 48(2): 62-71.
26. Eke P I, Dye B A, Wei L, Slade G D, Thornton-Evans G O, Borgnakke W S, et al. Update on Prevalence of Periodontitis in Adults in the United States: NHANES 2009 to 2012. J Periodontol 2015, 86(5): 611-622.
27. Graziani F, Karapetsa D, Alonso B, Herrera D. Nonsurgical and surgical treatment of periodontitis: how many options for one disease? Periodontology 2000 2017, 75(1): 152-188.
28. del Barrio J, Oriol L, Sanchez C, Serrano J L, Di Cicco A, Keller P, et al. Self-Assembly of Linear-Dendritic Diblock Copolymers: From Nanofibers to Polymersomes. Journal of the American Chemical Society 2010, 132(11): 3762-3769.
29. Tan X, Li B B, Lu X, Jia F, Santori C, Menon P, et al. Light-Triggered, Self-Immolative Nucleic Acid-Drug Nanostructures. Journal of the American Chemical Society 2015, 137(19): 6112-6115.
30. Allen C, Dos Santos N, Gallagher R, Chiu G N C, Shu Y, Li W M, et al. Controlling the physical behavior and biological performance of liposome formulations through use of surface grafted poly(ethylene glycol). Bioscience Reports 2002, 22(2): 225-250.
31. Kienberger F, Pastushenko V P, Kada G, Gruber H J, Riener C, Schindler H, et al. Static and Dynamical Properties of Single Poly(Ethylene Glycol) Molecules Investigated by Force Spectroscopy. Single Molecules 2000, 1(2): 123-128.
32. Lee H, Venable R M, MacKerell A D, Jr., Pastor R W. Molecular dynamics studies of polyethylene oxide and polyethylene glycol: Hydrodynamic radius and shape anisotropy. Biophysical Journal 2008, 95(4): 1590-1599.
33. Appel E A, Tibbitt M W, Webber M J, Mattix B A, Veiseh O, Langer R. Self-assembled hydrogels utilizing polymer-nanoparticle interactions. Nat Commun 2015, 6.
34. Guvendiren M, Lu H D, Burdick J A. Shear-thinning hydrogels for biomedical applications. Soft Matter 2012, 8(2): 260-272.
35. Yan C, Altunbas A, Yucel T, Nagarkar R P, Schneider J P, Pochan D J. Injectable solid hydrogel: mechanism of shear-thinning and immediate recovery of injectable [small beta]-hairpin peptide hydrogels. Soft Matter 2010, 6(20): 5143-5156.
36. Bakota E L, Wang Y, Danesh F R, Hartgerink J D. Injectable Multidomain Peptide Nanofiber Hydrogel as a Delivery Agent for Stem Cell Secretome. Biomacromolecules 2011, 12(5): 1651-1657.
37. Wong Po Foo C T S, Lee J S, Mulyasasmita W, Parisi-Amon A, Heilshorn S C. Two-component protein-engineered physical hydrogels for cell encapsulation. Proceedings of the National Academy of Sciences 2009, 106(52): 22067-22072.
38. Fleming S, Ulijn R V. Design of nanostructures based on aromatic peptide amphiphiles. Chemical Society Reviews 2014, 43(23): 8150-8177.
39. Schmidt P W. SMALL-ANGLE SCATTERING STUDIES OF DISORDERED, POROUS AND FRACTAL SYSTEMS. Journal of Applied Crystallography 1991, 24: 414-435.
40. Van Ommen J R, Valverde J M, Pfeffer R. Fluidization of nanopowders: a review. Journal of Nanoparticle Research 2012, 14(3).
41. Naviaux R K, Le T P, Bedelbaeva K, Leferovich J, Gourevitch D, Sachadyn P, et al. Retained features of embryonic metabolism in the adult MRL mouse. Molecular Genetics and Metabolism 2009, 96(3): 133-144.
42. Chu C R, Szczodry M, Bruno S. Animal Models for Cartilage Regeneration and Repair. Tissue Engineering Part B-Reviews 2010, 16(1): 105-115.
43. Philip Neil Edwards M S L, Neil James Hales, George R. Martin, Xinfan Huang Phenanthroline derivatives. WO Application 1999: International Publication No. WO9921860A9921861.

To the extent necessary to understand or complete the disclosure of the present invention, all publications, patents, and patent applications mentioned herein are expressly incorporated by reference therein to the same extent as though each were individually so incorporated.

Having thus described exemplary embodiments of the present invention, it should be noted by those skilled in the art that the within disclosures are exemplary only and that various other alternatives, adaptations, and modifications may be made within the scope of the present invention. Accordingly, the present invention is not limited to the specific embodiments as illustrated herein, but is only limited by the following claims.

What is claimed is:

1. A PEG-DPCA conjugate comprising two or more DPCA groups at one terminal end of a PEG compound or at each terminal end of the PEG compound, wherein said PEG-DPCA conjugate has structural Formula I or structural Formula II:

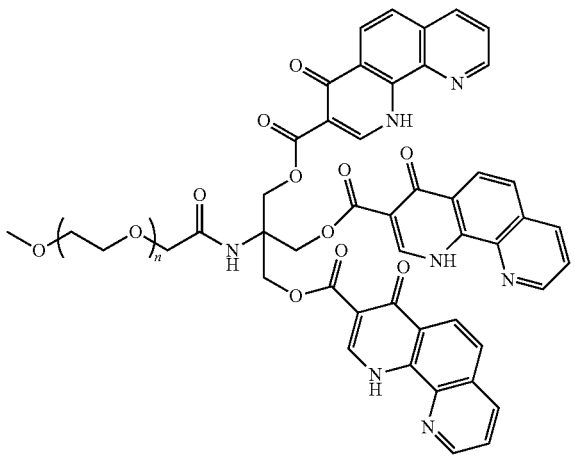

(I)

or

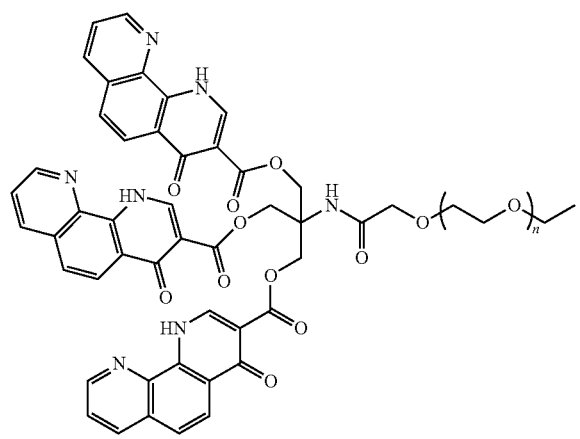

(II)

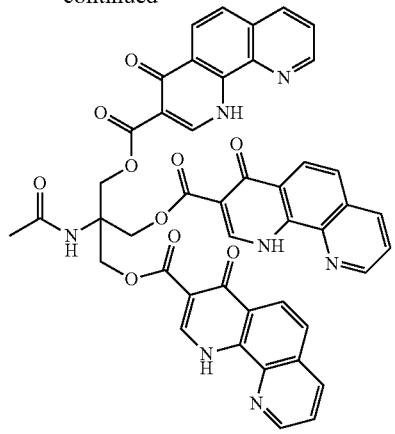

wherein n>1.

2. A composition comprising at least one PEG-DPCA conjugate according to claim 1.

3. The PEG-DPCA conjugate according to claim 1, wherein the PEG compound has an average molecular weight of about 250-20,000 Da, about 300-10,000 Da, about 400-9,000 Da, or about 500-8,000 Da.

4. A composition comprising two or more PEG-DPCA conjugates according to claim 1.

5. The composition of claim 2, wherein the composition comprises at least about 1 mg/mL, at least about 3 mg/mL, at least about 5 mg/mL, at least about 8 mg/mL, at least about 10 mg/mL, at least about 11 mg/mL, at least about 15 mg/mL, at least about 20 mg/mL, at least about 32 mg/mL, at least about 39 mg/mL, at least about 48 mg/mL, at least about 59 mg/mL, at least about 66 mg/mL, at least about 76 mg/mL, at least about 88 mg/mL, or at least about 100 mg/mL of the PEG-DPCA conjugate.

6. The composition of claim 5, wherein the conjugate comprises P7D3.

7. The composition of claim 2, wherein the composition comprises at least about 12 mg/mL, at least about 24 mg/mL, at least about 34 mg/mL, at least about 41 mg/mL, at least about 52 mg/mL, at least about 62 mg/mL, at least about 68 mg/mL, at least about 80 mg/mL, at least about 85 mg/mL, at least about 89 mg/mL, at least about 90 mg/mL, at least about 92 mg/mL, at least about 95 mg/mL, at least about 97 mg/mL, at least about 99 mg/mL, or at least about 100 mg/mL of the PEG-DPCA conjugate.

8. The composition of claim 7, wherein the conjugate comprises P80D6.

9. The composition of claim 4, wherein the composition is selected from the group consisting of:
  a) about 100 mg/mL of the PEG-DPCA conjugate having Structural Formula I and about 0 mg/mL of the PEG-DPCA conjugate having Structural Formula II;
  b) about 88 mg/mL of the PEG-DPCA conjugate having Structural Formula I and about 12 mg/mL of the PEG-DPCA conjugate having Structural Formula II;
  c) about 76 mg/mL of the PEG-DPCA conjugate having Structural Formula I and about 24 mg/mL of the PEG-DPCA conjugate having Structural Formula II;
  d) about 66 mg/mL of the PEG-DPCA conjugate having Structural Formula I and about 34 mg/mL of the PEG-DPCA conjugate having Structural Formula II;
  e) about 59 mg/mL of the PEG-DPCA conjugate having Structural Formula I and about 41 mg/mL of the PEG-DPCA conjugate having Structural Formula II;

f) about 48 mg/mL of the PEG-DPCA conjugate having Structural Formula I and about 52 mg/mL of the PEG-DPCA conjugate having Structural Formula II;
g) about 39 mg/mL of the PEG-DPCA conjugate having Structural Formula I and about 61 mg/mL of the PEG-DPCA conjugate having Structural Formula II;
h) about 32 mg/mL of the PEG-DPCA conjugate having Structural Formula I and about 68 mg/mL of the PEG-DPCA conjugate having Structural Formula II;
i) about 20 mg/mL of the PEG-DPCA conjugate having Structural Formula I and about 80 mg/mL of the PEG-DPCA conjugate having Structural Formula II;
j) about 15 mg/mL of the PEG-DPCA conjugate having Structural Formula I and about 85 mg/mL of the PEG-DPCA conjugate having Structural Formula II;
k) about 11 mg/mL of the PEG-DPCA conjugate having Structural Formula I and about 89 mg/mL of the PEG-DPCA conjugate having Structural Formula II;
l) About 10 mg/mL of the PEG-DPCA conjugate having Structural Formula I and about 90 mg/mL of the PEG-DPCA conjugate having Structural Formula II;
m) about 8 mg/mL of the PEG-DPCA conjugate having Structural Formula I and about 92 mg/mL of the PEG-DPCA conjugate having Structural Formula II;
n) about 5 mg/mL of the PEG-DPCA conjugate having Structural Formula I and about 95 mg/mL of the PEG-DPCA conjugate having Structural Formula II;
o) about 3 mg/mL of the PEG-DPCA conjugate having Structural Formula I and about 97 mg/mL of the PEG-DPCA conjugate having Structural Formula II;
p) about 1 mg/mL of the PEG-DPCA conjugate having Structural Formula I and about 99 mg/mL of the PEG-DPCA conjugate having Structural Formula II; and
q) about 0 mg/mL of the PEG-DPCA conjugate having Structural Formula I and about 100 mg/mL of the PEG-DPCA conjugate having Structural Formula II.

10. The composition of claim 9, wherein the PEG-DPCA conjugate having Structural Formula I is P7D3 and/or the PEG-DPCA conjugate having Structural Formula II is P80D6.

* * * * *